(12) United States Patent
Chang et al.

(10) Patent No.: US 7,910,658 B2
(45) Date of Patent: *Mar. 22, 2011

(54) COMPOSITIONS OF ETHYLENE/α-OLEFIN MULTI-BLOCK INTERPOLYMER FOR ELASTIC FILMS AND LAMINATES

(75) Inventors: Andy C. Chang, Houston, TX (US); Stephen M. Hoenig, Lake Jackson, TX (US); Yunwa W. Cheung, Monroe, NY (US); Daniel G. Moldovan, Danbury, TX (US); Wenbin Liang, Sugar Land, TX (US); Charles F. Diehl, Lake Jackson, TX (US)

(73) Assignee: Dow Global Technologies LLC, Midland, MI (US)

( * ) Notice: Subject to any disclaimer, the term of this patent is extended or adjusted under 35 U.S.C. 154(b) by 910 days.

This patent is subject to a terminal disclaimer.

(21) Appl. No.: 11/703,927

(22) Filed: Jan. 12, 2007

(65) Prior Publication Data

US 2007/0155900 A1    Jul. 5, 2007

Related U.S. Application Data

(63) Continuation-in-part of application No. 11/524,121, filed on Sep. 20, 2006, now Pat. No. 7,737,215, which is a continuation-in-part of application No. 11/376,956, filed on Mar. 15, 2006, now Pat. No. 7,714,071, and a continuation-in-part of application No. 11/377,333, filed on Mar. 15, 2006, now Pat. No. 7,355,089, application No. 11/703,927, which is a continuation-in-part of application No. 11/376,835, filed on Mar. 15, 2006, now Pat. No. 7,608,668.

(51) Int. Cl.
C08L 23/00 (2006.01)
C08L 23/04 (2006.01)
C08L 23/10 (2006.01)

(52) U.S. Cl. .................. 525/191; 525/232; 525/240

(58) Field of Classification Search .................. 525/191, 525/232, 240
See application file for complete search history.

(56) References Cited

U.S. PATENT DOCUMENTS

| | | |
|---|---|---|
| 3,873,642 A | 3/1975 | Jezl |
| 4,668,752 A | 5/1987 | Tominari et al. |
| 4,720,415 A | 1/1988 | Vander Wielen et al. |
| 4,789,699 A | 12/1988 | Kieffer et al. |
| 5,093,422 A | 3/1992 | Himes |
| 5,226,992 A | 7/1993 | Morman |
| 5,332,613 A | 7/1994 | Taylor et al. |
| 5,336,545 A | 8/1994 | Morman |
| 5,336,554 A | 8/1994 | Knight |
| 5,344,691 A | 9/1994 | Hanschen et al. |
| 5,354,597 A | 10/1994 | Capik et al. |
| 5,376,430 A | 12/1994 | Swenson et al. |
| 5,422,178 A | 6/1995 | Swenson et al. |
| 5,429,856 A | 7/1995 | Krueger et al. |
| 5,462,708 A | 10/1995 | Swenson et al. |
| 5,468,428 A | 11/1995 | Hanschen et al. |
| 5,468,810 A | 11/1995 | Hayakawa et al. |
| 5,501,679 A | 3/1996 | Krueger et al. |
| 5,514,470 A | 5/1996 | Haffner et al. |
| 5,594,080 A | 1/1997 | Waymouth et al. |
| 5,610,253 A | 3/1997 | Hatke et al. |
| 5,620,780 A | 4/1997 | Krueger et al. |
| 5,635,275 A | 6/1997 | Biagioli et al. |
| 5,635,276 A | 6/1997 | Biagioli et al. |
| 5,691,034 A | 11/1997 | Krueger et al. |
| 5,698,054 A | 12/1997 | Biagioli et al. |
| 5,733,628 A | 3/1998 | Pelkie |
| 5,733,980 A | 3/1998 | Cozewith et al. |
| 5,783,014 A | 7/1998 | Biagioli et al. |
| 5,798,420 A | 8/1998 | Cozewith et al. |
| 5,800,903 A | 9/1998 | Wood et al. |
| 5,840,412 A | 11/1998 | Wood et al. |
| 5,945,196 A | 8/1999 | Rieker et al. |
| 5,969,070 A | 10/1999 | Waymouth et al. |
| 6,015,764 A | 1/2000 | McCormack et al. |
| 6,114,457 A | 9/2000 | Markel et al. |
| 6,147,180 A | 11/2000 | Markel et al. |
| 6,159,584 A | 12/2000 | Eaton et al. |
| 6,218,470 B1 | 4/2001 | Betso et al. |
| 6,255,236 B1 | 7/2001 | Cree et al. |
| 6,262,203 B1 | 7/2001 | Chien et al. |
| 6,303,208 B1 | 10/2001 | Pelkie |
| 6,323,389 B1 | 11/2001 | Thomas et al. |
| 6,369,161 B1 | 4/2002 | Betso et al. |
| 6,388,040 B1 | 5/2002 | Fujita et al. |
| 6,472,084 B1 | 10/2002 | Middlesworth et al. |
| 6,566,544 B1 | 5/2003 | Waymouth et al. |

(Continued)

FOREIGN PATENT DOCUMENTS

| | | |
|---|---|---|
| EP | 0500590 | 9/1992 |
| EP | 0274906 B1 | 2/1993 |
| EP | 0712892 | 5/1996 |
| EP | 1013732 | 6/2000 |
| EP | 1375585 A1 | 3/2002 |
| EP | 0958313 B1 | 9/2002 |
| EP | 1262498 A2 | 12/2002 |
| EP | 1637320 | 3/2006 |
| JP | 2000135762 | 5/2000 |
| JP | 2000159944 | 6/2000 |
| JP | 2002-206007 | 7/2002 |
| JP | 2003011142 | 1/2003 |
| JP | 2003019778 | 1/2003 |
| JP | 2004154228 | 6/2004 |
| JP | 2004-204058 | 7/2004 |
| WO | WO-95/27745 A1 | 10/1995 |
| WO | WO-95/27746 A1 | 10/1995 |

(Continued)

OTHER PUBLICATIONS

"Styrene Block Copolymer Modified Food Wrap Film", Annual Technical Conference—Society of Plastics Engineers (2002), 60th(vol. 2), 2440-2442.

*Primary Examiner* — Nathan M Nutter

(57) ABSTRACT

This invention relates to polyolefin compositions. In particular, the invention pertains to elastic polymer compositions that can be more easily processed on cast film lines, extrusion lamination or coating lines. The compositions of the present invention preferably comprise an elastomeric polyolefin resin and a high pressure low density type resin.

10 Claims, 15 Drawing Sheets

U.S. PATENT DOCUMENTS

| | | |
|---|---|---|
| 6,582,829 B1 | 6/2003 | Quinn et al. |
| 6,808,789 B2 | 10/2004 | Pelkie et al. |
| 6,849,319 B2 | 2/2005 | Cree et al. |
| 7,355,089 B2 * | 4/2008 | Chang et al. .................. 604/358 |
| 2003/0022582 A1 | 1/2003 | Cree et al. |
| 2003/0195308 A1 | 10/2003 | Waymouth et al. |
| 2004/0082750 A1 | 4/2004 | Tau et al. |
| 2004/0087235 A1 | 5/2004 | Morman et al. |
| 2004/0121922 A1 | 6/2004 | Okada et al. |
| 2004/0122408 A1 | 6/2004 | Potnis et al. |
| 2004/0122409 A1 | 6/2004 | Thomas et al. |
| 2005/0003152 A1 | 1/2005 | Thomas et al. |
| 2005/0043460 A1 | 2/2005 | McCormack et al. |
| 2005/0158513 A1 | 7/2005 | Peacock et al. |
| 2007/0078222 A1* | 4/2007 | Chang et al. .................... 525/88 |
| 2008/0177242 A1* | 7/2008 | Chang et al. ............. 604/385.01 |
| 2008/0234435 A1* | 9/2008 | Chang et al. .................. 525/240 |

FOREIGN PATENT DOCUMENTS

| | | |
|---|---|---|
| WO | WO-9815399 | 4/1998 |
| WO | WO-9829479 | 7/1998 |
| WO | WO-98/34970 A1 | 8/1998 |
| WO | WO-9917926 | 4/1999 |
| WO | WO-99/35171 A1 | 7/1999 |
| WO | WO-00/37514 A1 | 6/2000 |
| WO | WO-02/066540 A2 | 8/2002 |
| WO | WO-03/014046 A1 | 2/2003 |
| WO | WO-2004041538 | 5/2004 |
| WO | WO-2005/021262 | 3/2005 |
| WO | WO-2005/023544 | 3/2005 |
| WO | WO-2005/090425 A1 | 9/2005 |
| WO | WO-2005/090426 A1 | 9/2005 |
| WO | WO-2005/090427 A1 | 9/2005 |

* cited by examiner

COMPOSITIONS OF ETHYLENE/α-OLEFIN MULTI-BLOCK INTERPOLYMER FOR ELASTIC FILMS AND LAMINATES

CROSS-REFERENCE TO RELATED APPLICATIONS

This application is a continuation-in-part of U.S. application Ser. No. 11/524,121, filed Sep. 20, 2006, and now U.S. Pat. No. 7,737,215, which is a continuation-in-part of U.S. application Ser. No. 11/376,956, filed Mar. 15, 2006, and now U.S. Pat. No. 7,714,071, and said Ser. No. 11/524,121 is a continuation-in-part of U.S. application Ser. No. 11/377,333, filed Mar. 15, 2006, and now U.S. Pat. No. 7,355,089. This application is also a continuation-in-part of U.S. application Ser. No. 11/376,835, filed Mar. 15, 2006, and now U.S. Pat. No. 7,608,668. For purposes of United States patent practice, the contents of the above referenced applications are herein incorporated by reference in their entirety.

FIELD OF THE INVENTION

This invention relates to ethylene/α-olefin multi-block interpolymer compositions and blends of ethylene/α-olefin multi-block interpolymer compositions and styrenic block copolymers having suitability for elastic compositions with improved processability. In one aspect, this invention relates to breathable films in which at least one component is made from ethylene/α-olefin multi-block interpolymer compositions and blends of ethylene/α-olefin multi-block interpolymer compositions and styrenic block copolymers. In yet another aspect, this invention relates to breathable laminates comprising filaments, fibers, films, or combinations thereof made from ethylene/α-olefin multi-block interpolymer compositions and blends of ethylene/α-olefin multi-block interpolymer compositions and styrenic block copolymers. In still yet another aspect, this invention relates to articles fabricated using films, fibers, filaments, laminates, or combinations thereof made using ethylene/α-olefin multi-block interpolymer compositions and blends of ethylene/α-olefin multi-block interpolymer compositions and styrenic block copolymers. The compositions have elastic performance, improved heat resistance, and other desirable characteristics.

BACKGROUND AND SUMMARY OF THE INVENTION

Styrenic block copolymers, such as SEBS (polystyrene-saturated polybutadiene-polystyrene), SBS (polystyrene-polybutadiene-polystyrene), SEPS (polystyrene-saturated polyisoprene-polystyrene), SIS (polystyrene-polyisoprene-polystyrene), and SEPSEP are known in the art. They exhibit excellent physical properties, such as elasticity and flexibility. However, they often cannot be readily processed on typical polyolefin processing equipment, without the need for flow enhancers and other processing aids. Upon formulation with such materials, end-use properties such as tensile strength and heat resistance can suffer. Furthermore, they can suffer from thermal instability phenomenon such as cross-linking (i.e. SBS) and scission (i.e. SIS).

Ethylene/α-olefin multi-block interpolymer compositions are readily processable using typical polyolefin processing equipment. They exhibit desirable end-use properties such as high heat resistance and high tensile strength. However, ethylene/α-olefin multi-block interpolymer compositions are typically are not as flexible and elastic as the most elastic styrenic block copolymers when used at high strains (i.e. >100%).

It would be desirable to have a thermoplastic elastomer composition which exhibits excellent physical properties, such as elasticity and flexibility, while at the same time being readily processable using typical polyolefin processing equipment.

Elastomeric compositions have found particular use in elastic films and fibers. They can be used by themselves, but are more commonly used in laminated structure wherein the substrate is a nonwoven fabric. The elastic film or fiber imparts elasticity to the nonwoven laminates. Such elastic nonwoven laminate materials have found use in the hygiene and medical market particularly in such applications as elastic diaper tabs, side panels of training pants, leg gathers, feminine hygiene articles, swim pants, incontinent wear, veterinary products, protective clothing, bandages, items of health care such as surgeon's gowns, surgical drapes, sterilization wrap, wipes, and the like.

These materials may also find use in other nonwoven applications including but are not limited to filters (gas and liquid), automotive and marine protective covers, home furnishing such as bedding, carpet underpaddings, wall coverings, floor coverings, window shades, scrims etc.

Elastomeric films can be made in a number of ways known to those of ordinary skill in the art. Single or multi-layer elastic films are possible. Such processes can include bubble extrusion and biaxial orientation processes, as well as tenter frame techniques. In order to facilitate elasticity, the elastic film is usually employed singly or as a layer, in the case of multi-layer films. As many elastic compositions tend to be sticky and hence difficult to process or poor in hand feel, at least one non-sticky/non-tacky material may be used to comprise at least a portion of the film surface to mitigate this effect. Alternatively, non-blocking skin layers, and various additives and modifiers (i.e. slip agents, anti-block etc.) may also be employed.

Elastomeric fibers or filaments can be made in a number of ways known to those of ordinary skill in the art. Monofilament, conjugate, bicomponent, multicomponent, islands-in-the-sea, crescent, side-by-side and other configurations known to those of ordinary skill in the art are suitable for use with the inventive composition. Like films, elastic fibers also tend to be sticky and hence difficult to process or poor in hand feel. At least one non-sticky/non-tacky material may be used to comprise at least a portion of the film or fiber surface to mitigate this effect. Alternatively, non-blocking components (i.e. higher crystalline polymer comprising at least a portion of the surface of the fiber or filament), and various additives and modifiers (i.e. slip agents, anti-block etc.) as mentioned above may also be employed.

Elastomeric compositions are often used for their retractive force. They are commonly used in various forms including fibers, film, laminates and fabric. When used in an article, the retractive force of the elastomer provides the "holding force" of the structure. For example, in health and hygiene articles such as infant diapers, training pants, and adult incontinence articles, the elastomers are commonly used in laminate structures. These laminate structures help to maintain fit of the article to the body. Body heat can result in the decrease of the holding force of the elastomer over time (measured as stress-relaxation) which can translate to loosening and eventual sagging of the article resulting in a decrease in fit. Styrenic block copolymers and their formulations used in these structures can suffer from excessive stress-relaxation and consequently articles fabricated using these materials can sag unacceptably in end-use. Accordingly, it is a goal to reduce the amount of stress-relaxation (increase in heat resistance) of the elastomer. This phenomenon is a known problem and has been described previously in the art. Such art includes but is not limited to WO9829248A1, WO0058541A1, US20020052585A1, US20040127128A1, U.S. Pat. No. 6,916,750B2, U.S. Pat. No. 6,547,915B2, U.S. Pat. No. 6,323,389B1, U.S. Pat. No. 6,207,237B1, U.S. Pat. No. 6,187,425B1, U.S. Pat. No. 5,332,613A, U.S. Pat. No. 5,288,791A, U.S. Pat. No. 5,260,126A, U.S. Pat. No. 5,169,706A, GB2335427A, and WO2004037141A1.

In addition to stretch and elasticity considerations, in the personal care area in particular, there has been an emphasis on the development of film laminates which have good barrier properties, especially with respect to liquids, as well as a necessary level of vapor permeability, or breathability, to maintain the skin health of a product user, such as described in WO2005/021262. It would be desirable to provide an elastic film that exhibits good processability as well as these desirable characteristics.

The invention provides an elastic breathable film and laminates and articles comprising the film wherein the film comprises an elastomer comprising at least one ethylene/α-olefin interpolymer elastomer, wherein the ethylene/α-olefin interpolymer elastomer:

(a) has a Mw/Mn (Mw denotes weight averaged molecular weight; Mn denotes number averaged molecular weight) from about 1.7 to about 3.5, at least one melting point, Tm, in degrees Celsius, and a density, d, in grams/cubic centimeter, wherein the numerical values of Tm and d correspond to the relationship:

$$Tm > -2002.9 + 4538.5(d) - 2422.2(d)^2; \text{ or}$$

(b) has a Mw/Mn from about 1.7 to about 3.5, and is characterized by a heat of fusion, ΔH in J/g, and a delta quantity, ΔT, in degrees Celsius defined as the temperature difference between the tallest DSC peak and the tallest CRYSTAF peak, wherein the numerical values of ΔT and ΔH have the following relationships:

$$\Delta T > -0.1299(\Delta H) + 62.81 \text{ for } \Delta H \text{ greater than zero and up to 130 J/g,}$$

$$\Delta T \geq 48° \text{ C. for } \Delta H \text{ greater than 130 J/g,}$$

wherein the CRYSTAF peak is determined using at least 5 percent of the cumulative polymer, and if less than 5 percent of the polymer has an identifiable CRYSTAF peak, then the CRYSTAF temperature is 30° C.; or (c) is characterized by an elastic recovery, Re, in percent at 300 percent strain and 1 cycle measured with a compression-molded film of the ethylene/α-olefin interpolymer, and has a density, d, in grams/cubic centimeter, wherein the numerical values of Re and d satisfy the following relationship when ethylene/α-olefin interpolymer is substantially free of a cross-linked phase:

Re>1481-1629(d); or (d) has a molecular fraction which elutes between 40° C. and 130° C. when fractionated using TREF, characterized in that the fraction has a molar comonomer content of at least 5 percent higher than that of a comparable random ethylene interpolymer fraction eluting between the same temperatures, wherein said comparable random ethylene interpolymer has the same comonomer(s) and has a melt index, density, and molar comonomer content (based on the whole polymer) within 10 percent of that of the ethylene/α-olefin interpolymer;

(e) has a storage modulus at 25° C., G'(25° C.), and a storage modulus at 100° C., G'(100° C.), wherein the ratio of G'(25° C.) to G'(100° C.) is in the range of about 1:1 to about 9:1; or (f) has a molecular fraction which elutes between 40° C. and 130° C. when fractionated using TREF, characterized in that the fraction has a block index of at least 0.5 and up to about 1 and a molecular weight distribution, Mw/Mn, greater than about 1.3; or (g) has an average block index greater than zero and up to about 1.0 and a molecular weight distribution, Mw/Mn, greater than about 1.3; and optionally, at least one styrenic block copolymer;

wherein the ethylene/α-olefin interpolymer has a density of from about 0.855 to about 0.878 g/cc (grams per cubic centimeter).

The invention also provides a method for forming an elastic, breathable film comprising aperturing the film, wherein the film comprises:

at least one ethylene/α-olefin interpolymer, wherein the ethylene/α-olefin interpolymer (a) has a Mw/Mn from about 1.7 to about 3.5, at least one melting point, Tm, in degrees Celsius, and a density, d, in grams/cubic centimeter, wherein the numerical values of Tm and d correspond to the relationship:

$$Tm > -2002.9 + 4538.5(d) - 2422.2(d)^2; \text{ or}$$

(b) has a Mw/Mn from about 1.7 to about 3.5, and is characterized by a heat of fusion, ΔH in J/g, and a delta quantity, ΔT, in degrees Celsius defined as the temperature difference between the tallest DSC peak and the tallest CRYSTAF peak, wherein the numerical values of ΔT and ΔH have the following relationships:

$$\Delta T > -0.1299(\Delta H) + 62.81 \text{ for } \Delta H \text{ greater than zero and up to 130 J/g,}$$

$$\Delta T \geq 48° \text{ C. for } \Delta H \text{ greater than 130 J/g,}$$

wherein the CRYSTAF peak is determined using at least 5 percent of the cumulative polymer, and if less than 5 percent of the polymer has an identifiable CRYSTAF peak, then the CRYSTAF temperature is 30° C.; or (c) is characterized by an elastic recovery, Re, in percent at 300 percent strain and 1 cycle measured with a compression-molded film of the ethylene/α-olefin interpolymer, and has a density, d, in grams/cubic centimeter, wherein the numerical values of Re and d satisfy the following relationship when ethylene/α-olefin interpolymer is substantially free of a cross-linked phase:

Re>1481-1629(d); or (d) has a molecular fraction which elutes between 40° C. and 130° C. when fractionated using TREF, characterized in that the fraction has a molar comonomer content of at least 5 percent higher than that of a comparable random ethylene interpolymer fraction eluting between the same temperatures, wherein said comparable random ethylene interpolymer has the same comonomer(s) and has a melt index, density, and molar comonomer content (based on the whole polymer) within 10 percent of that of the ethylene/α-olefin interpolymer;

(e) has a storage modulus at 25° C., G'(25° C.), and a storage modulus at 100° C., G'(100° C.), wherein the ratio of G'(25° C.) to G'(100° C.) is in the range of about 1:1 to about 9:1; or (f) has a molecular fraction which elutes between 40° C. and 130° C. when fractionated using TREF, characterized in that the fraction has a block index of at least 0.5 and up to about 1 and a molecular weight distribution, Mw/Mn, greater than about 1.3; or (g) has an average block index greater than zero and up to about 1.0 and a molecular weight distribution, Mw/Mn, greater than about 1.3; and optionally, a styrenic block copolymer, or a combination thereof wherein the ethylene/α-olefin interpolymer has a density of from about 0.85 to about 0.885 g/cc.

The invention additionally provides a method for forming an elastic, breathable film/nonwoven layer laminate comprising:

filling a higher crystalline, predominantly linear polymer with a filler to form a filled polymer such that the filled polymer contains at least 60 percent by weight filler;

dry-blending a thermoplastic elastomer with the filled polymer to form a blended elastomeric composition, such that the blended elastomeric composition includes between about 25 and 70 percent filler by weight, between about 5 and 30 percent higher crystalline polymer by weight, and between about 15 and 60 percent by weight elastomer;

extruding the blended elastomeric composition into a film; and, bonding the film to a nonwoven layer to produce a film/nonwoven layer laminate wherein the elastomer comprises at least one ethylene/α-olefin interpolymer, wherein the ethylene/α-olefin interpolymer (a) has a Mw/Mn from about 1.7 to about 3.5, at least one melting point, Tm, in degrees Celsius, and a density, d, in grams/cubic centimeter, wherein the numerical values of Tm and d correspond to the relationship:

$$Tm > -2002.9 + 4538.5(d) - 2422.2(d)^2; \text{ or}$$

(b) has a Mw/Mn from about 1.7 to about 3.5, and is characterized by a heat of fusion, ΔH in J/g, and a delta quantity, ΔT, in degrees Celsius defined as the temperature difference between the tallest DSC peak and the tallest CRYSTAF peak, wherein the numerical values of ΔT and ΔH have the following relationships:

$$\Delta T > -0.1299(\Delta H) + 62.81 \text{ for } \Delta H \text{ greater than zero and up to 130 J/g,}$$

$$\Delta T \geq 48° \text{ C. for } \Delta H \text{ greater than 130 J/g,}$$

wherein the CRYSTAF peak is determined using at least 5 percent of the cumulative polymer, and if less than 5 percent of the polymer has an identifiable CRYSTAF peak, then the CRYSTAF temperature is 30° C.; or (c) is characterized by an elastic recovery, Re, in percent at 300 percent strain and 1 cycle measured with a compression-molded film of the ethylene/α-olefin interpolymer, and has a density, d, in grams/cubic centimeter, wherein the numerical values of Re and d satisfy the following relationship when ethylene/α-olefin interpolymer is substantially free of a cross-linked phase:

Re>1481−1629(d); or (d) has a molecular fraction which elutes between 40° C. and 130° C. when fractionated using TREF, characterized in that the fraction has a molar comonomer content of at least 5 percent higher than that of a comparable random ethylene interpolymer fraction eluting between the same temperatures, wherein said comparable random ethylene interpolymer has the same comonomer(s) and has a melt index, density, and molar comonomer content (based on the whole polymer) within 10 percent of that of the ethylene/α-olefin interpolymer;

(e) has a storage modulus at 25° C., G'(25° C.), and a storage modulus at 100° C., G'(100° C.), wherein the ratio of G'(25° C.) to G'(100° C.) is in the range of about 1:1 to about 9:1; or (f) has a molecular fraction which elutes between 40° C. and 130° C. when fractionated using TREF, characterized in that the fraction has a block index of at least 0.5 and up to about 1 and a molecular weight distribution, Mw/Mn, greater than about 1.3; or (g) has an average block index greater than zero and up to about 1.0 and a molecular weight distribution, Mw/Mn, greater than about 1.3; and optionally, a styrenic block copolymer, or a combination thereof wherein the ethylene/α-olefin interpolymer has a density of from about 0.85 to about 0.885 g/cc.

DETAILED DESCRIPTION OF THE INVENTION

General Definitions

Figure 1:
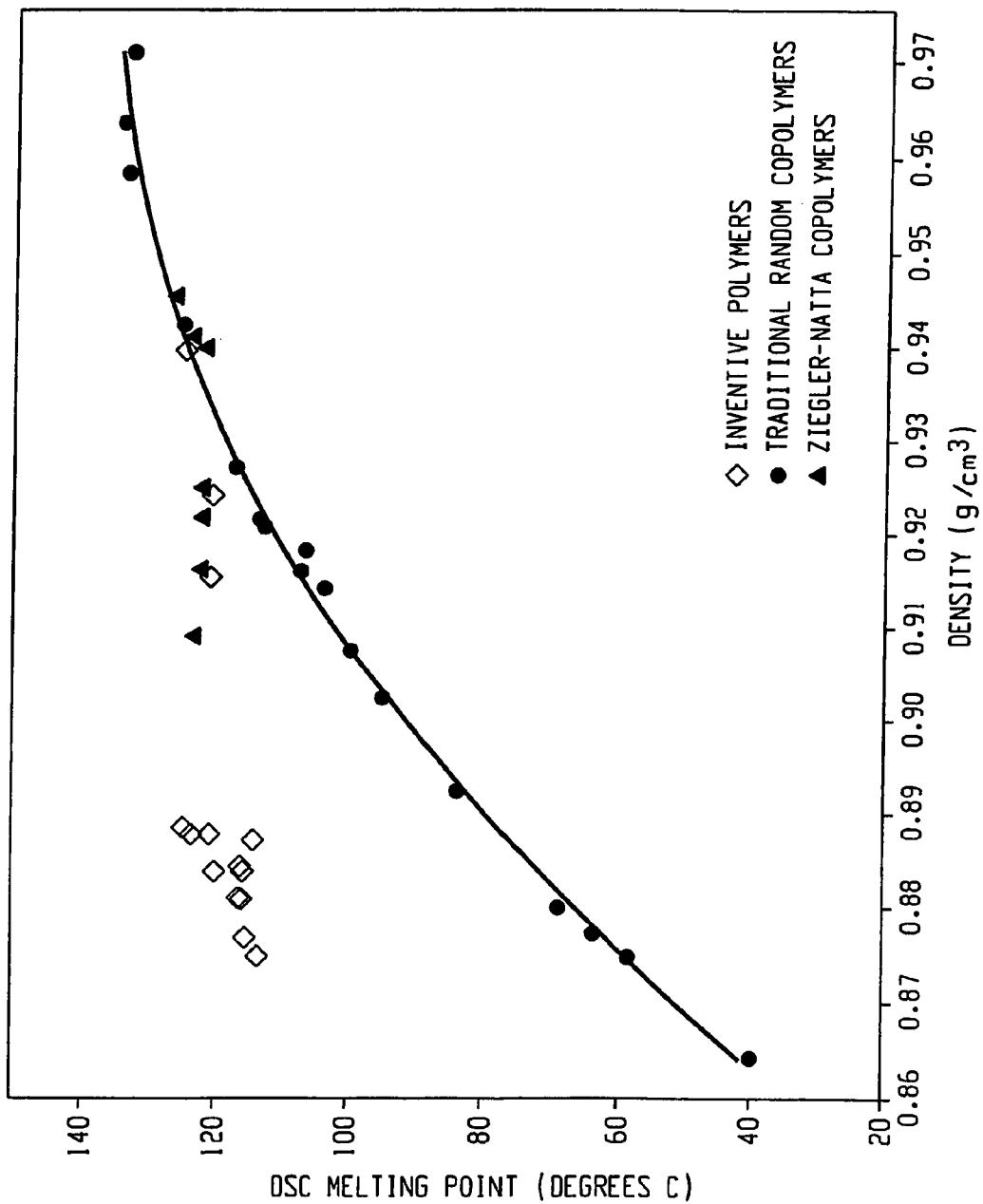
FIG. 1 shows the melting point/density relationship for the inventive polymers (represented by diamonds) as compared to traditional random copolymers (represented by circles) and Ziegler-Natta copolymers (represented by triangles).

The following terms shall have the given meaning for the purposes of this invention:

By "neck-in" is meant the reduction in a film web width as it is extruded from a die and which will be caused by a combination of swelling and surface tension effects as the material leaves the die. Neck-in is measured as the distance between the extrudate web as it emerges from the die minus the width of the extrudate web as it is taken up.

"Polymer" means a polymeric compound prepared by polymerizing monomers, whether of the same or a different type. The generic term "polymer" embraces the terms "homopolymer," "copolymer," "terpolymer" as well as "interpolymer."

"Interpolymer" means a polymer prepared by the polymerization of at least two different types of monomers. The generic term "interpolymer" includes the term "copolymer" (which is usually employed to refer to a polymer prepared from two different monomers) as well as the term "terpolymer" (which is usually employed to refer to a polymer prepared from three different types of monomers). It also encompasses polymers made by polymerizing four or more types of monomers.

The term "ethylene/α-olefin interpolymer" generally refers to polymers comprising ethylene and an α-olefin having 3 or more carbon atoms. Preferably, ethylene comprises the majority mole fraction of the whole polymer, i.e., ethylene comprises at least about 50 mole percent of the whole polymer. More preferably ethylene comprises at least about 60 mole percent, at least about 70 mole percent, or at least about 80 mole percent, with the substantial remainder of the whole polymer comprising at least one other comonomer that is preferably an α-olefin having 3 or more carbon atoms. For many ethylene/octene copolymers, the preferred composition comprises an ethylene content greater than about 80 mole percent of the whole polymer and an octene content of from about 10 to about 15, preferably from about 15 to about 20 mole percent of the whole polymer. In some embodiments, the ethylene/α-olefin interpolymers do not include those produced in low yields or in a minor amount or as a by-product of a chemical process. While the ethylene/α-olefin interpolymers can be blended with one or more polymers, the as-produced ethylene/α-olefin interpolymers are substantially pure and often comprise a major component of the reaction product of a polymerization process.

The ethylene/α-olefin interpolymers comprise ethylene and one or more copolymerizable α-olefin comonomers in polymerized form, characterized by multiple blocks or segments of two or more polymerized monomer units differing in chemical or physical properties. That is, the ethylene/α-olefin interpolymers are block interpolymers, or "olefin block copolymers", preferably multi-block interpolymers or copolymers. The terms "interpolymer" and copolymer" are used interchangeably herein. In some embodiments, the multi-block copolymer can be represented by the following formula:

(AB)$_n$ where n is at least 1, preferably an integer greater than 1, such as 2, 3, 4, 5, 10, 15, 20, 30, 40, 50, 60, 70, 80, 90, 100, or higher, "A" represents a hard block or segment and "B" represents a soft block or segment. Preferably, As and Bs are linked in a substantially linear fashion, as opposed to a substantially branched or substantially star-shaped fashion. In other embodiments, A blocks and B blocks are randomly distributed along the polymer chain. In other words, the block copolymers usually do not have a structure as follows.

AAA-AA-BBB-BB

In still other embodiments, the block copolymers do not usually have a third type of block, which comprises different comonomer(s). In yet other embodiments, each of block A and block B has monomers or comonomers substantially randomly distributed within the block. In other words, neither block A nor block B comprises two or more sub-segments (or sub-blocks) of distinct composition, such as a tip segment, which has a substantially different composition than the rest of the block.

The multi-block polymers typically comprise various amounts of "hard" and "soft" segments. "Hard" segments refer to blocks of polymerized units in which ethylene is present in an amount greater than about 95 weight percent, and preferably greater than about 98 weight percent based on the weight of the polymer. In other words, the comonomer content (content of monomers other than ethylene) in the hard segments is less than about 5 weight percent, and preferably less than about 2 weight percent based on the weight of the polymer. In some embodiments, the hard segments comprise all or substantially all ethylene. "Soft" segments, on the other hand, refer to blocks of polymerized units in which the comonomer content (content of monomers other than ethylene) is greater than about 5 weight percent, preferably greater than about 8 weight percent, greater than about 10 weight percent, or greater than about 15 weight percent based on the weight of the polymer. In some embodiments, the comonomer content in the soft segments can be greater than about 20 weight percent, greater than about 25 weight percent, greater than about 30 weight percent, greater than about 35 weight percent, greater than about 40 weight percent, greater than about 45 weight percent, greater than about 50 weight percent, or greater than about 60 weight percent.

The soft segments can often be present in a block interpolymer from about 1 weight percent to about 99 weight percent of the total weight of the block interpolymer, preferably from about 5 weight percent to about 95 weight percent, from about 10 weight percent to about 90 weight percent, from about 15 weight percent to about 85 weight percent, from about 20 weight percent to about 80 weight percent, from about 25 weight percent to about 75 weight percent, from about 30 weight percent to about 70 weight percent, from about 35 weight percent to about 65 weight percent, from about 40 weight percent to about 60 weight percent, or from about 45 weight percent to about 55 weight percent of the total weight of the block interpolymer. Conversely, the hard segments can be present in similar ranges. The soft segment weight percentage and the hard segment weight percentage can be calculated based on data obtained from DSC or NMR. Such methods and calculations are disclosed in U.S. Patent Application Publication No. 2006-0199930A1, entitled "Ethylene/α-Olefin Block Interpolymers", filed on Mar. 15, 2006, in the name of Colin L. P. Shan, Lonnie Hazlitt, et. al. and assigned to Dow Global Technologies Inc., the disclosure of which is herein incorporated by reference in its entirety.

The term "crystalline" if employed, refers to a polymer that possesses a first order transition or crystalline melting point (Tm) as determined by differential scanning calorimetry (DSC) or equivalent technique. The term may be used interchangeably with the term "semicrystalline". The term "amorphous" refers to a polymer lacking a crystalline melting point as determined by differential scanning calorimetry (DSC) or equivalent technique.

"Elastomeric" means that the material will substantially resume its original shape after being stretched. To qualify a material as elastomeric and thus suitable for the first component, a 1-cycle hysteresis test to 80% strain was used. For this test, the specimens (6 inches long by 1 inch wide) were then loaded lengthwise into a Sintech type mechanical testing device fitted with pneumatically activated line-contact grips with an initial separation of 4 inches. Then the sample was stretched to 80% strain at 500 mm/min, and returned to 0% strain at the same speed. The strain at 10 g load upon retraction was taken as the set. Upon immediate and subsequent extension, the onset of positive tensile force was taken as the set strain. The hysteresis loss is defined as the energy difference between the extension and retraction cycle. The load down was the retractive force at 50% strain. In all cases, the samples were measured green or unaged. Strain is defined as the percent change in sample length divided by the original sample length (22.25 mm) equal to the original grip separation. Stress is defined as the force divided by the initial cross sectional area.

The term "multi-block copolymer" or "segmented copolymer" refers to a polymer comprising two or more chemically distinct regions or segments (referred to as "blocks") preferably joined in a linear manner, that is, a polymer comprising chemically differentiated units which are joined end-to-end with respect to polymerized ethylenic functionality, rather than in pendent or grafted fashion. In a preferred embodiment, the blocks differ in the amount or type of comonomer incorporated therein, the density, the amount of crystallinity, the crystallite size attributable to a polymer of such composition, the type or degree of tacticity (isotactic or syndiotactic), regio-regularity or regio-irregularity, the amount of branching, including long chain branching or hyper-branching, the homogeneity, or any other chemical or physical property. The multi-block copolymers are characterized by unique distributions of both polydispersity index (PDI or Mw/Mn), block length distribution, and/or block number distribution due to the unique process making of the copolymers. More specifically, when produced in a continuous process, the polymers desirably possess PDI from 1.7 to 2.9, preferably from 1.8 to 2.5, more preferably from 1.8 to 2.2, and most preferably from 1.8 to 2.1. When produced in a batch or semi-batch process, the polymers possess PDI from 1.0 to 2.9, preferably from 1.3 to 2.5, more preferably from 1.4 to 2.0, and most preferably from 1.4 to 1.8.

In the following description, all numbers disclosed herein are approximate values, regardless whether the word "about" or "approximate" is used in connection therewith. Depending upon the context in which such values are described herein, and unless specifically stated otherwise, such values may vary by 1 percent, 2 percent, 5 percent, or, sometimes, 10 to 20 percent. Whenever a numerical range with a lower limit, RL and an upper limit, RU, is disclosed, any number falling within the range is specifically disclosed. In particular, the following numbers within the range are specifically disclosed: $R=RL+k*(RU-RL)$, wherein k is a variable ranging from 1 percent to 100 percent with a 1 percent increment, i.e., k is 1 percent, 2 percent, 3 percent, 4 percent, 5 percent, . . . , 50 percent, 51 percent, 52 percent, . . . , 95 percent, 96 percent, 97 percent, 98 percent, 99 percent, or 100 percent. Moreover, any numerical range defined by two R numbers as defined in the above is also specifically disclosed.

For purposes of this invention, a polymer is generally considered to be "elastic" if when fabricated into a film, the film has a permanent set of less than 40% as determined according to the following procedure: a 1 inch wide by 6 inch long sample is loaded lengthwise into a Sintech mechanical testing device fitted with pneumatically activated line-contact grips with an initial separation of 4 inches. Then, the sample is stretched to 80% strain at 500 mm/min and returned to 0% strain at the same speed. The strain at 0.05 MPa (megapascals) upon retraction is taken as the permanent set.

"Density" is tested in accordance with ASTM D792.

"Melt Index ($I_2$)" is determined according to ASTM D1238 using a weight of 2.16 kg at 190° C. for polymers comprising ethylene as the major component in the polymer.

"Melt Flow Rate (MFR)" is determined according to ASTM D1238 using a weight of 2.16 kg at 230° C. for polymers comprising propylene as the major component in the polymer.

"Molecular weight distribution" or MWD is measured by conventional GPC per the procedure described by Williams, T.; Ward, I. M. *Journal of Polymer Science, Polymer Letters Edition* (1968), 6(9), 621-624. Coefficient B is 1. Coefficient A is 0.4316.

The term high pressure low density type resin is defined to mean that the polymer is partly or entirely homopolymerized or copolymerized in autoclave or tubular reactors at pressures above 14,500 psi (100 MPa) with the use of free-radical initiators, such as peroxides (see for example U.S. Pat. No. 4,599,392, herein incorporated by reference) and includes "LDPE" which may also be referred to as "high pressure ethylene polymer" or "highly branched polyethylene". The cumulative detector fraction (CDF) of these materials is greater than about 0.02 for molecular weight greater than 1000000 g/mol as measured using light scattering. CDF may be determined as described in WO2005/023912 A2, which is herein incorporated by reference for its teachings regarding CDF.

The term "high pressure low density type resin" also includes branched polypropylene materials (both homopolymer and copolymer). For the purposes of the present invention, "branched polypropylene materials" means the type of branched polypropylene materials disclosed in WO2003/082971, hereby incorporated by reference in its entirety.

As used herein, the term "personal care product" means diapers, training pants, swimwear, absorbent underpants, adult incontinence products, and feminine hygiene products, such as feminine care pads, napkins and pantiliners.

As used herein the term "protective outer wear" means garments used for protection in the workplace, such as surgical gowns, hospital gowns, masks, and protective coveralls.

As used herein, the term "protective cover" means covers that are used to protect objects such as for example car, boat and barbeque grill covers, as well as agricultural fabrics.

As used herein the terms "polymer" and "polymeric" generally include but are not limited to, homopolymers, copolymers, such as for example, block, graft, random and alternating copolymers, terpolymers, etc. and blends and modifications thereof.

Furthermore, unless otherwise specifically limited, the term "polymer" includes all possible spatial configurations of the molecule. These configurations include, but are not limited to isotactic, syndiotactic and random symmetries.

As used herein, the terms "machine direction" or MD means the length of a fabric, film, fiber, or laminate in the direction in which it is produced. The terms "cross machine direction," "cross directional," or CD mean the width of fabric, film, fiber, or laminate, i.e. a direction generally perpendicular to the MD.

As used herein, the term "nonwoven web" means a polymeric web having a structure of individual fibers or threads which are interlaid, but not in an identifiable, repeating manner. Nonwoven webs have been, in the past, formed by a variety of processes such as, for example, meltblowing processes, spunbonding processes, hydroentangling, air-laid and bonded carded web processes.

As used herein, the term "bonded carded webs" refers to webs that are made from staple fibers which are usually purchased in bales. The bales are placed in a fiberizing unit/picker which opens the bale from the compact state and separates the fibers. Next, the fibers are sent through a combining or carding unit which further breaks apart and aligns the staple fibers in the machine direction so as to form a machine direction-oriented fibrous non-woven web. Once the web has been formed, it is then bonded by one or more of several bonding methods. One bonding method is powder bonding wherein a powdered adhesive is distributed throughout the web and then activated, usually by heating the web and adhesive with hot air. Another bonding method is pattern bonding wherein heated calendar rolls or ultrasonic bonding equipment is used to bond the fibers together, usually in a localized bond pattern through the web and or alternatively the web may be bonded across its entire surface if so desired. When using bicomponent staple fibers, through-air bonding equipment is, for many applications, especially advantageous.

As used herein the term "spunbond" refers to small diameter fibers which are formed by extruding molten thermoplastic material as filaments from a plurality of fine, usually circular capillaries of a spinneret with the diameter of the extruded filaments being rapidly reduced as by for example in U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,542,615 to Dobo et al., which are each incorporated by reference in their entirety herein.

As used herein the term "meltblown" means fibers formed by extruding a molten thermoplastic material through a plurality of fine, usually circular die capillaries as molten threads or filaments into converging high velocity gas (e.g. air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly dispersed meltdown fibers. Such a process is disclosed, in various patents and publications, including NRL Report 4364, "Manufacture of Super-Fine Organic Fibers" by B. A. Wendt, E. L. Boone and D. D. Fluharty; NRL Report 5265, "An Improved Device For The Formation of Super-Fine Thermoplastic Fibers" by K. D. Lawrence, R. T. Lukas, J. A. Young; and U.S. Pat. No. 3,849,241, issued Nov. 19, 1974, to Butin, et al. As used herein the term "sheet" or "sheet material" refers to woven materials, nonwoven webs, polymeric films, polymeric scrim-like materials, and polymeric foam sheeting.

The basis weight of nonwoven fabrics is usually expressed in ounces of material per square yard (osy) or grams per square meter ($g/m^2$ or gsm) and the fiber diameters useful are usually expressed in microns. (Note that to convert from osy to gsm, multiply osy by 33.91). Film thicknesses may also be expressed in microns.

As used herein the term "laminate" refers to a composite structure of two or more sheet material layers that have been adhered through a bonding step, such as through adhesive bonding, thermal bonding, point bonding, pressure bonding, extrusion coating or ultrasonic bonding.

As used herein, the term "elastomeric" shall be interchangeable with the term "elastic" and refers to sheet material which, upon application of a stretching force, is stretchable in at least one direction (such as the CD direction), and which upon release of the stretching force contracts/returns to approximately its original dimension. For example, a stretched material having a stretched length which is at least 50 percent greater than its relaxed unstretched length, and which will recover to within at least 50 percent of its stretched length upon release of the stretching force. A hypothetical example would be a one (1) inch sample of a material which is stretchable to at least 1.50 inches and which, upon release of the stretching force, will recover to a length of not more than 1.25 inches.

Desirably, such elastomeric sheet contracts or recovers up to 50 percent of the stretch length in the cross machine direction using a cycle test as described herein to determine percent set. Even more desirably, such elastomeric sheet material recovers up to 80 percent of the stretch length in the cross machine direction using a cycle test as described. Even more desirably, such elastomeric sheet material recovers greater than percent of the stretch length in the cross direction using a cycle test as described.

Desirably, such elastomeric sheet is stretchable and recoverable in both the MD and CD directions. For the purposes of this application, values of load loss and other "elastomeric functionality testing" have been generally measured in the CD direction, unless otherwise noted. Unless otherwise noted, such test values have been measured at 50 percent elongation on a 70 percent total elongation cycle (as described further in the test method section).

As used herein, the term "elastomer" shall refer to a polymeric composition which is elastomeric.

As used herein, the term "thermoplastic" shall refer to a polymer which is capable of being melt processed.

As used herein, the term "inelastic" or "nonelastic" refers to any material which does not fall within the definition of "elastic" above.

As used herein, the term "breathable" refers to a material which is permeable to water vapor. The water vapor transmission rate (WVTR) or moisture vapor transfer rate (MVTR) is measured in grams per square meter per 24 hours, and shall be considered equivalent indicators of breathability. The term "breathable" desirably refers to a material which is permeable to water vapor having a minimum WVTR (water vapor transmission rate) of desirably about 100 $g/m^2/24$ hours. Even more desirably, such material demonstrates breathability greater than about 300 $g/m^2/24$ hours. Still even more desirably, such material demonstrates breathability greater than about 1000 $g/m^2/24$ hours.

The WVTR of a fabric, in one aspect, gives an indication of how comfortable a fabric would be to wear. WVTR is measured as indicated below. Often, personal care product applications of breathable barriers desirably have higher WVTRs and breathable barriers of the present invention can have WVTRs exceeding about 1,200 $g/m^2/24$ hours, 1,500 $g/m^2/24$ hours, 1,800 $g/m^2/24$ hours or even exceeding 2,000 $g/m^2/24$ hours.

Air flow through the apertured film or laminate may be measured by ASTM D-737. Porosity is desired as this allows transport of gases, liquids, and particles through the film or laminate for a variety of purposes (i.e. water vapor transmission prevents moisture build-up against the skin in a health and hygiene article, hence promoting skin health). The amount of air flow through the film or laminate may be controlled by the aperture size and density. Adjusting the porosity to a given air flow rate for a variety of applications is therefore obvious. In general, porosity measured is >1, preferably >5, more preferably >10, even more preferably >100 CFM/sq. ft. for typical health and hygiene applications.

As used herein, the term "multilayer laminate" means a laminate including a variety of different sheet materials. For instance, a multi-layered laminate may include some layers of spunbond and some meltblown such as a spunbond/meltblown/spunbond (SMS) laminate and others as disclosed in U.S. Pat. No. 4,041,203 to Brock et al., U.S. Pat. No. 5,169,706 to Collier, et al., U.S. Pat. No. 5,145,727 to Potts et al., U.S. Pat. No. 5,178,931 to Perkins et al., and U.S. Pat. No. 5,188,885 to Timmons et al., each incorporated by reference in their entirety. Such a laminate may be made by sequentially depositing onto a moving forming belt first a spunbond fabric layer, then a meltblown fabric layer and last another spunbond layer and then bonding the laminate. Alternatively, the fabric layers may be made individually, collected in rolls, and combined in a separate bonding step or steps. Multilayer laminates may also have various numbers of meltblown layers or multiple spunbond layers in many different configurations and may include other materials like films or coform materials, e.g. SMMS, SM and SFS. As used herein, the term "coform" means a process in which at least one meltblown diehead is arranged near a chute through which other materials are added to the web while it is forming. Such other materials may be pulp, superabsorbent particles, cellulosic fibers or staple fibers, for example. Coform processes are shown in commonly assigned U.S. Pat. No. 4,818,464 to Lau and U.S. Pat. No. 4,100,324 to Anderson et al., each incorporated by reference in their entirety.

As used herein, the term "conjugate fibers" refers to fibers which have been formed from at least two polymers extruded from separate extruders but spun together to form one fiber. Conjugate fibers are also sometimes referred to as multicomponent or bicomponent fibers. The polymers are usually different from each other though conjugate fibers may be monocomponent fibers. The polymers are arranged in substantially constantly positioned distinct zones across the cross-section of the conjugate fibers and extend continuously along the length of the conjugate fibers. The configuration of such conjugate fiber may be, for example, a sheath/core arrangement wherein one polymer is surrounded by another or may be a side by side arrangement, a pie arrangement or an "islands-in-the-sea" arrangement. Conjugate fibers are taught in U.S. Pat. No. 5,108,820 to Kaneko et al., U.S. Pat. No. 4,795,668 to Krueger et al., and U.S. Pat. No. 5,336,552 to Strack et al. Conjugate fibers are also taught in U.S. Pat. No. 5,382,400 to Pike et al., and may be used to produce crimp in the fibers by using the differential rates of expansion and contraction of the two or more polymers. For two component fibers, the polymers may be present in varying desired ratios. The fibers may also have shapes such as those described in U.S. Pat. No. 5,277,976 to Hogle et al., U.S. Pat. No. 5,466,410 to Hills and U.S. Pat. Nos. 5,069,970 and 5,057,368 to Largman et al., which describe fibers with unconventional shapes.

As used herein the term "thermal point bonding" involves passing a fabric or web of fibers to be bonded between a heated calender roll and an anvil roll. The calender roll is usually, though not always, patterned in some way so that the entire fabric is not bonded across its entire surface, and the anvil roll is usually flat. As a result, various patterns for calender rolls have been developed for functional as well as aesthetic reasons. One example of a pattern has points and is the Hansen Pennings or "H&P" pattern with about a 30% bond area with about 200 bonds/square inch as taught in U.S. Pat. No. 3,855,046 to Hansen and Pennings, incorporated herein by reference in its entirety. The H&P pattern has square point or pin bonding areas wherein each pin has a side dimension of 0.038 inches (0.965 mm), a spacing of 0.070 inches (1.778 mm) between pins, and a depth of bonding of 0.023 inches (0.584 mm). The resulting pattern has a bonded area of about 29.5%. Another typical point bonding pattern is the expanded Hansen Pennings or "EHP" bond pattern which produces a 15% bond area with a square pin having a side dimension of 0.037 inches (0.94 mm), a pin spacing of 0.097 inches (2.464 mm) and a depth of 0.039 inches (0.991 mm). Another typical point bonding pattern designated "714" has square pin bonding areas wherein each pin has a side dimension of 0.023 inches, a spacing of 0.062 inches (1.575 mm) between pins, and a depth of bonding of 0.033 inches (0.838 mm). The resulting pattern has a bonded area of about 15%. Yet another common pattern is the C-Star pattern which has a bond area of about 16.9%. The C-Star pattern has a cross-directional bar or "corduroy" design interrupted by shooting stars. Other common patterns include a diamond pattern with repeating and slightly offset diamonds with about a 16% bond area and a wire weave pattern looking as the name suggests, e.g. like a window screen pattern having a bond area in the range of from about 15% to about 21% and about 302 bonds per square inch. Typically, the percent bonding area varies from around 10% to around 30% of the area of the fabric laminate web. As is well known in the art, the spot bonding holds the laminate layers together as well as imparts integrity to each individual layer by bonding filaments and/or fibers within each layer.

As used herein, the term "ultrasonic bonding" means a process performed, for example, by passing the fabric between a sonic horn and anvil roll as illustrated in U.S. Pat. No. 4,374,888 to Bornslaeger, incorporated by reference herein in its entirety.

As used herein, the term "adhesive bonding" means a bonding process which forms a bond by application of an adhesive. Such application of adhesive may be by various processes such as slot coating, spray coating and other topical applications. Further, such adhesive may be applied within a product component and then exposed to pressure such that contact of a second product component with the adhesive containing product component forms an adhesive bond between the two components.

As used herein and in the claims, the term "comprising" is inclusive or open-ended and does not exclude additional unrecited elements, compositional components, or method steps. Accordingly, such terms are intended to be synonymous with the words "has", "have", "having", "includes", "including", and any derivatives of these words.

As used herein the terms "recover", "recovery" and "recovered" shall be used interchangeably and shall refer to a contraction of a stretched material upon termination of a stretching force following stretching of the material by application of the stretching force.

For example, if a material having a relaxed, unstretched length of 1 inch (2.5 cm) is elongated fifty percent by stretching to a length of 1.5 inches (3.75 cm), the material would be elongated 50 percent and would have a stretched length that is 150 percent of its relaxed length or stretched 1.5×. If this exemplary stretched material contracted, that is recovered to a length of 1.1 inches (2.75 cm) after release of the stretching force, the material would have recovered 80 percent of its 0.5 inch (1.25 cm) elongation. Percent recovery may be expressed as [(maximum stretch length-final sample length)/(maximum stretch length-initial sample length)]×100.

As used herein the term "extensible" means elongatable in at least one direction, but not necessarily recoverable.

As used herein the term "percent stretch" refers to the ratio determined by measuring the increase in the stretched dimension and dividing that value by the original dimension. i.e. (increase in stretched dimension/original dimension)×100.

As used herein the term "set" refers to retained elongation in a material sample following the elongation and recovery, i.e. after the material has been stretched and allowed to relax during a cycle test.

As used herein the term "percent set" is the measure of the amount of the material stretched from its original length after being cycled (the immediate deformation following the cycle test). The percent set is where the retraction curve of a cycle crosses the elongation axis. The remaining strain after the removal of the applied stress is measured as the percent set.

The "load loss" value is determined by first elongating a sample to a defined elongation in a particular direction (such as the CD) of a given percentage (such as 70 or percent as indicated) and then allowing the sample to retract to an amount where the amount of resistance is zero. The cycle is repeated a second time and the load loss is calculated at a given elongation, such as at the 50 percent elongation. Unless otherwise indicated, the value was read at the 50% elongation level (on a 70 percent elongation test) and then used in the calculation. For the purposes of this application, the load loss was calculated as follows:

$$\frac{\text{cycle 1 extension (at 50\% elongation)} - \text{cycle 2 retraction tension (at 50\% elongation)}}{\text{cycle 1 extension (at 50\% elongation)}} \times 100$$

For the test results reflected in this application, the defined elongation was 70 percent unless otherwise noted. The actual test method for determining load loss values is described below in the section entitled Cycle Testing.

As used herein, "filler" is meant to include particulates and/or other forms of materials which can be added to a film polymer extrusion material which will not chemically interfere with or adversely affect the extruded film and further which are capable of being dispersed throughout the film. Generally the fillers will be in particulate form with average particle sizes in the range of about 0.1 to about 10 microns, desirably from about 0.1 to about 4 microns. As used herein, the term "particle size" describes the largest dimension or length of the filler particle.

As used herein the terms "higher crystalline", "predominantly linear polymer and higher crystalline" polymer shall refer to polyethylene, polypropylene, blends of such polymers and copolymers of such polymers. For such polyethylene-based polymers, such term shall be defined to mean polymers having a melt index of greater than about 5 g/10 min but desirably greater than 10 g/10 min (Condition E at 190° C., 2.16 kg) and a density of greater than about 0.910 g/cc, but desirably greater than about 0.915 g/cc. In one embodiment, the density is between about 0.915 g/cc and 0.960 g/cc. In a further alternative embodiment, the density is about 0.917 g/cc. In a further alternative embodiment, the density is between about 0.917 g/cc and 0.960 g/cc. In still a further alternative embodiment, the density is between about 0.917 g/cc and 0.923 g/cc. In still a further alternative embodiment, the density is between about 0.923 g/cc and 0.960 g/cc. For such polypropylene based polymers, such term shall be defined to mean polymers having a melt flow rate greater than about 10 g/10 min. but desirably greater than about 20 g/10 min. (230° C., 2.16 kg) and having a density between about 0.89 g/cc and 0.90 g/cc.

Unless otherwise indicated, percentages of components in formulations are by weight.

Ethylene/α-Olefin Interpolymers

The ethylene/α-olefin interpolymers used in embodiments of the invention (also referred to as "inventive interpolymer", "inventive polymer" or "olefin block copolymer") comprise ethylene and one or more copolymerizable α-olefin comonomers in polymerized form, characterized by multiple blocks or segments of two or more polymerized monomer units differing in chemical or physical properties (block interpolymer), preferably a multi-block copolymer. The ethylene/α-olefin interpolymers are characterized by one or more of the aspects described as follows.

In one aspect, the ethylene/α-olefin interpolymers used in embodiments of the invention have a $M_w/M_n$ from about 1.7 to about 3.5 and at least one melting point, $T_m$, in degrees Celsius and density, d, in grams/cubic centimeter, wherein the numerical values of the variables correspond to the relationship:

$$T_m > -2002.9 + 4538.5(d) - 2422.2(d)^2,\text{ and preferably}$$

$$T_m \geq -6288.1 + 13141(d) - 6720.3(d)^2,\text{ and more preferably}$$

$$T_m \geq 858.91 - 1825.3(d) + 1112.8(d)^2.$$

Such melting point/density relationship is illustrated in FIG. 1. Unlike the traditional random copolymers of ethylene/α-olefins whose melting points decrease with decreasing densities, the inventive interpolymers (represented by diamonds) exhibit melting points substantially independent of the density, particularly when density is between about 0.87 g/cc to about 0.95 g/cc. For example, the melting point of such polymers are in the range of about 110° C. to about 130° C. when density ranges from 0.875 g/cc to about 0.945 g/cc. In some embodiments, the melting point of such polymers are in the range of about 115° C. to about 125° C. when density ranges from 0.875 g/cc to about 0.945 g/cc.

Figure 2:
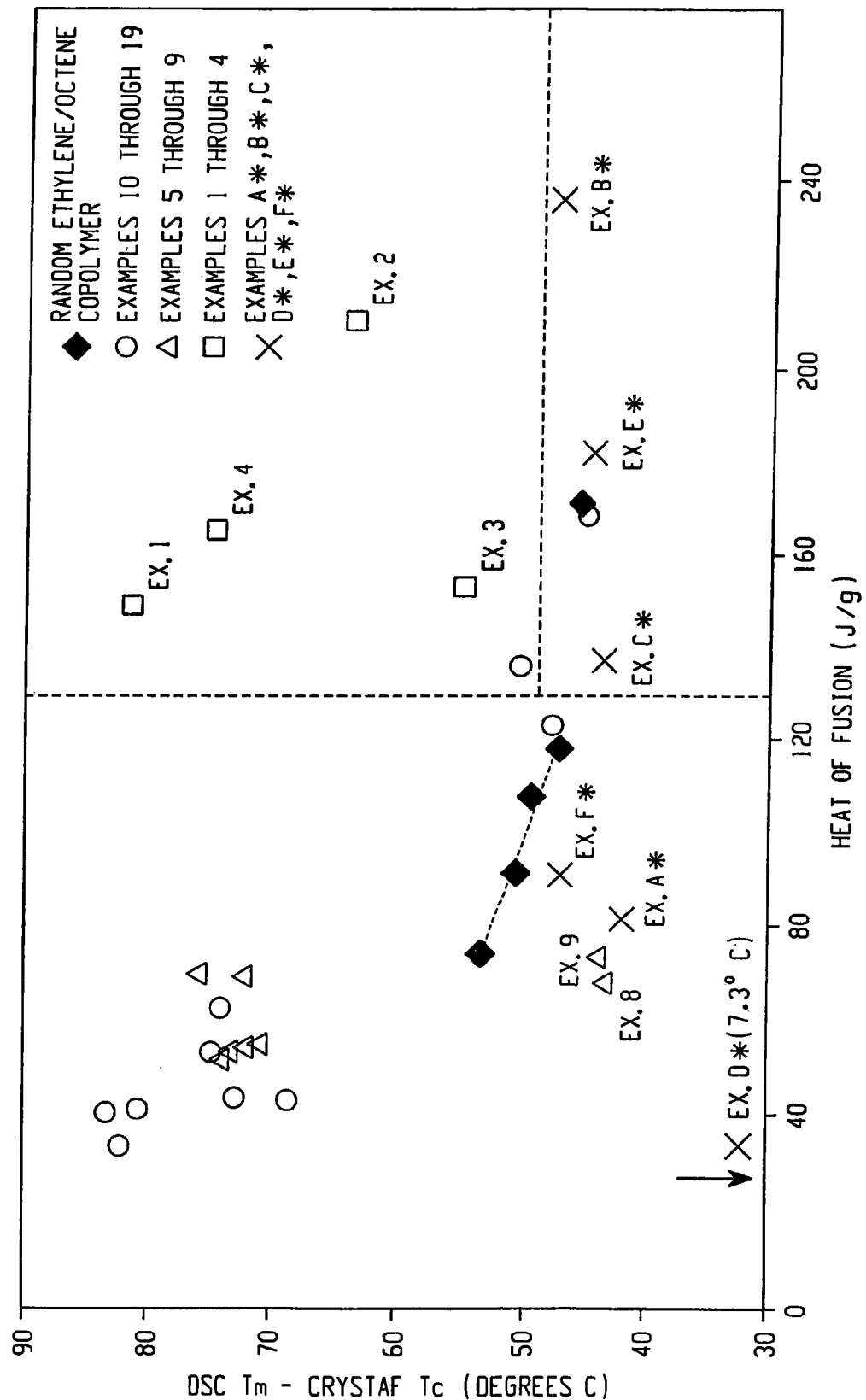
FIG. 2 shows plots of delta DSC-CRYSTAF as a function of DSC Melt Enthalpy for various polymers. The diamonds represent random ethylene/octene copolymers; the squares represent polymer examples 1-4; the triangles represent polymer examples 5-9; and the circles represent polymer Examples 10-19. The "X" symbols represent polymer Comparative Examples A*-F*.

In another aspect, the ethylene/α-olefin interpolymers comprise, in polymerized form, ethylene and one or more α-olefins and are characterized by a ΔT, in degrees Celsius, defined as the temperature for the tallest Differential Scanning Calorimetry ("DSC") peak minus the temperature for the tallest Crystallization Analysis Fractionation ("CRYSTAF") peak and a heat of fusion in J/g, ΔH, and ΔT and ΔH satisfy the following relationships:

$$\Delta T > -0.1299(\Delta H) + 62.81,\text{ and preferably}$$

$$\Delta T \geq -0.1299(\Delta H) + 64.38,\text{ and more preferably}$$

$$\Delta T \geq -0.1299(\Delta H) + 65.95,$$

for ΔH up to 130 J/g. Moreover, ΔT is equal to or greater than 48° C. for ΔH greater than 130 J/g. The CRYSTAF peak is determined using at least 5 percent of the cumulative polymer (that is, the peak must represent at least 5 percent of the cumulative polymer), and if less than 5 percent of the polymer has an identifiable CRYSTAF peak, then the CRYSTAF temperature is 30° C., and ΔH is the numerical value of the heat of fusion in J/g. More preferably, the highest CRYSTAF peak contains at least 10 percent of the cumulative polymer. FIG. 2 shows plotted data for inventive polymers as well as comparative examples. Integrated peak areas and peak temperatures are calculated by the computerized drawing program supplied by the instrument maker. The diagonal line shown for the random ethylene octene comparative polymers corresponds to the equation ΔT=−0.1299 (ΔH)+62.81.

In yet another aspect, the ethylene/α-olefin interpolymers have a molecular fraction which elutes between 40° C. and 130° C. when fractionated using Temperature Rising Elution Fractionation ("TREF"), characterized in that said fraction has a molar comonomer content higher, preferably at least 5 percent higher, more preferably at least 10 percent higher, than that of a comparable random ethylene interpolymer fraction eluting between the same temperatures, wherein the comparable random ethylene interpolymer contains the same comonomer(s), and has a melt index, density, and molar comonomer content (based on the whole polymer) within 10 percent of that of the block interpolymer. Preferably, the Mw/Mn of the comparable interpolymer is also within 10 percent of that of the block interpolymer and/or the comparable interpolymer has a total comonomer content within 10 weight percent of that of the block interpolymer.

In still another aspect, the ethylene/α-olefin interpolymers are characterized by an elastic recovery, Re, in percent at 300 percent strain and 1 cycle measured on a compression-molded film of an ethylene/α-olefin interpolymer, and has a density, d, in grams/cubic centimeter, wherein the numerical values of Re and d satisfy the following relationship when ethylene/α-olefin interpolymer is substantially free of a cross-linked phase:

Re>1481−1629(d); and preferably

Re≧1491−1629(d); and more preferably

Re≧1501−1629(d); and even more preferably

Re≧1511−1629(d).

Figure 3:
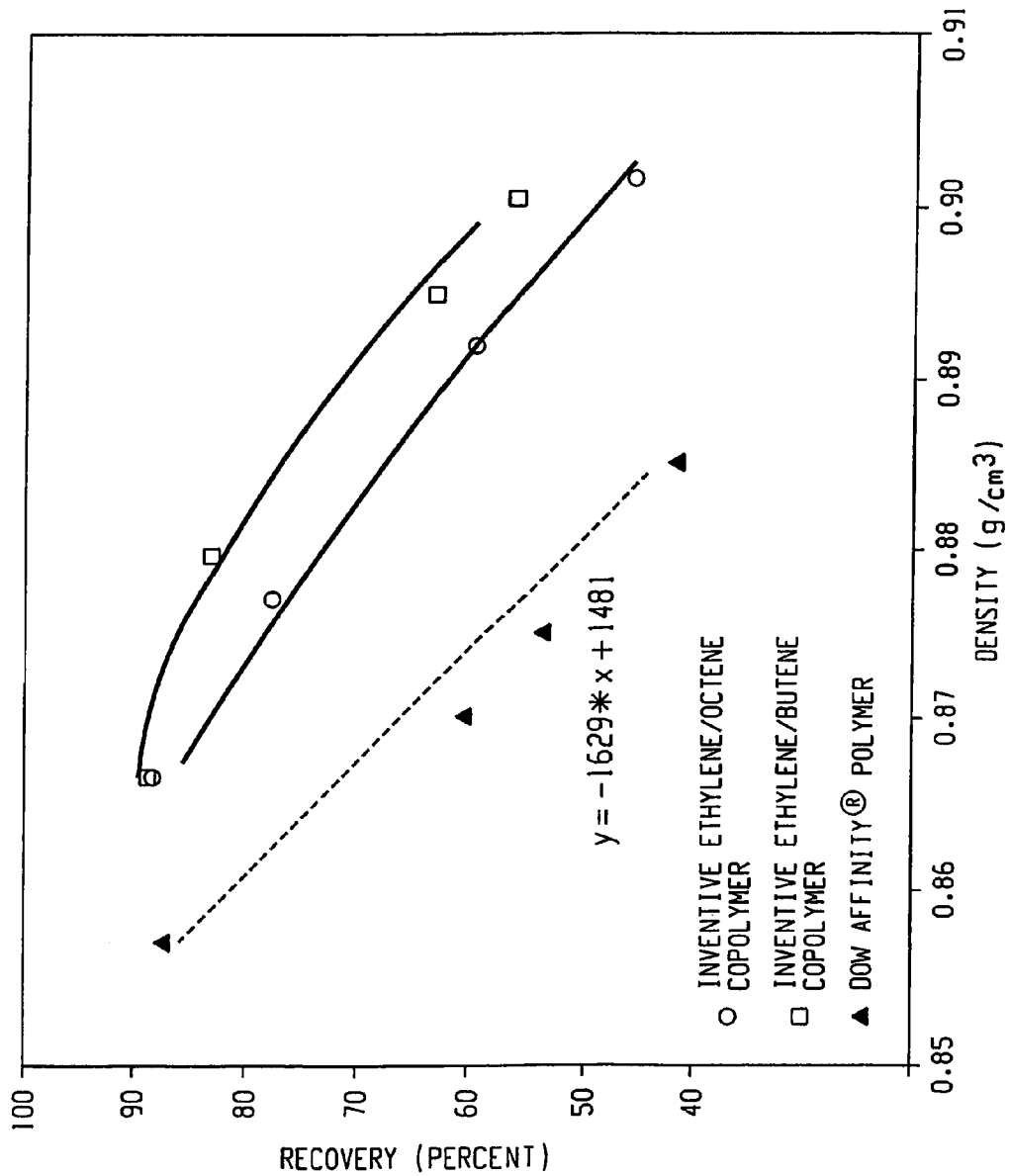
FIG. 3 shows the effect of density on elastic recovery for unoriented films made from inventive interpolymers (represented by the squares and circles) and traditional copolymers (represented by the triangles which are various AFFINITY® polymers). The squares represent inventive ethylene/butene copolymers; and the circles represent inventive ethylene/octene copolymers.

FIG. 3 shows the effect of density on elastic recovery for unoriented films made from certain inventive interpolymers and traditional random copolymers. For the same density, the inventive interpolymers have substantially higher elastic recoveries.

In some embodiments, the ethylene/α-olefin interpolymers have a tensile strength above 1 MPa, preferably a tensile strength ≧2 MPa, more preferably a tensile strength ≧3 MPa and/or an elongation at break of at least 100 percent, more preferably at least 250 percent, highly preferably at least 500 percent, and most highly preferably at least 750 percent at a crosshead separation rate of 11 cm/minute using microtensile ASTM-1708 geometry.

In still other embodiments, the ethylene/α-olefin interpolymers have a 70° C. compression set (ASTM D-3574) of less than 98 percent, preferably less than 95 percent, and more preferably less than 93 percent.

In some embodiments, the ethylene/α-olefin interpolymers have a heat of fusion of less than 85 J/g and/or a pellet blocking strength of equal to or less than 100 pounds/foot$^2$ (4800 Pa), preferably equal to or less than 50 lbs/ft$^2$ (2400 Pa), especially equal to or less than 5 lbs/ft$^2$ (240 Pa), and as low as 0 lbs/ft$^2$ (0 Pa).

In other embodiments, the ethylene/α-olefin interpolymers comprise, in polymerized form, at least 50 mole percent ethylene and have a 70° C. compression set of less than 80 percent, preferably less than 70 percent or less than 60 percent, most preferably less than 40 to 50 percent and down to close to zero percent.

In some embodiments, the multi-block copolymers possess a PDI fitting a Schultz-Flory distribution rather than a Poisson distribution. The copolymers are further characterized as having both a polydisperse block distribution and a polydisperse distribution of block sizes and possessing a most probable distribution of block lengths. Preferred multi-block copolymers are those containing 4 or more blocks or segments including terminal blocks. More preferably, the copolymers include at least 5, 10 or 20 blocks or segments including terminal blocks.

Comonomer content may be measured using any suitable technique, with techniques based on nuclear magnetic resonance ("NMR") spectroscopy preferred. Moreover, for polymers or blends of polymers having relatively broad TREF curves, the polymer desirably is first fractionated using TREF into fractions each having an eluted temperature range of 10° C. or less. That is, each eluted fraction has a collection temperature window of 10° C. or less. Using this technique, said block interpolymers have at least one such fraction having a higher molar comonomer content than a corresponding fraction of the comparable interpolymer.

In another aspect, the inventive polymer is an olefin interpolymer, preferably comprising ethylene and one or more copolymerizable comonomers in polymerized form, characterized by multiple blocks (i.e., at least two blocks) or segments of two or more polymerized monomer units differing in chemical or physical properties (blocked interpolymer), most preferably a multi-block copolymer, said block interpolymer having a peak (but not just a molecular fraction) which elutes between 40° C. and 130° C. (but without collecting and/or isolating individual fractions), characterized in that said peak, has a comonomer content estimated by infra-red spectroscopy when expanded using a full width/half maximum (FWHM) area calculation, has an average molar comonomer content higher, preferably at least 5 percent higher, more preferably at least 10 percent higher, than that of a comparable random ethylene interpolymer peak at the same elution temperature and expanded using a full width/half maximum (FWHM) area calculation, wherein said comparable random ethylene interpolymer has the same comonomer(s) and has a melt index, density, and molar comonomer content (based on the whole polymer) within 10 percent of that of the blocked interpolymer. Preferably, the Mw/Mn of the comparable interpolymer is also within 10 percent of that of the blocked interpolymer and/or the comparable interpolymer has a total comonomer content within 10 weight percent of that of the blocked interpolymer. The full width/half maximum (FWHM) calculation is based on the ratio of methyl to methylene response area [$CH_3/CH_2$] from the ATREF infra-red detector, wherein the tallest (highest) peak is identified from the base line, and then the FWHM area is determined. For a distribution measured using an ATREF peak, the FWHM area is defined as the area under the curve between $T_1$ and $T_2$, where $T_1$ and $T_2$ are points determined, to the left and right of the ATREF peak, by dividing the peak height by two, and then drawing a line horizontal to the base line, that intersects the left and right portions of the ATREF curve. A calibration curve for comonomer content is made using random ethylene/α-olefin copolymers, plotting comonomer content from NMR versus FWHM area ratio of the TREF peak. For this infra-red method, the calibration curve is generated for the same comonomer type of interest. The comonomer content of TREF peak of the inventive polymer can be determined by referencing this calibration curve using its FWHM methyl: methylene area ratio [$CH_3/CH_2$] of the TREF peak.

Comonomer content may be measured using any suitable technique, with techniques based on nuclear magnetic resonance (NMR) spectroscopy preferred. Using this technique, said blocked interpolymers have a higher molar comonomer content than a corresponding comparable interpolymer.

Preferably, for interpolymers of ethylene and 1-octene, the block interpolymer has a comonomer content of the TREF fraction eluting between 40 and 130° C. greater than or equal to the quantity (−0.2013)T+20.07, more preferably greater than or equal to the quantity (−0.2013)T+21.07, where T is the numerical value of the peak elution temperature of the TREF fraction being compared, measured in ° C.

Figure 4:
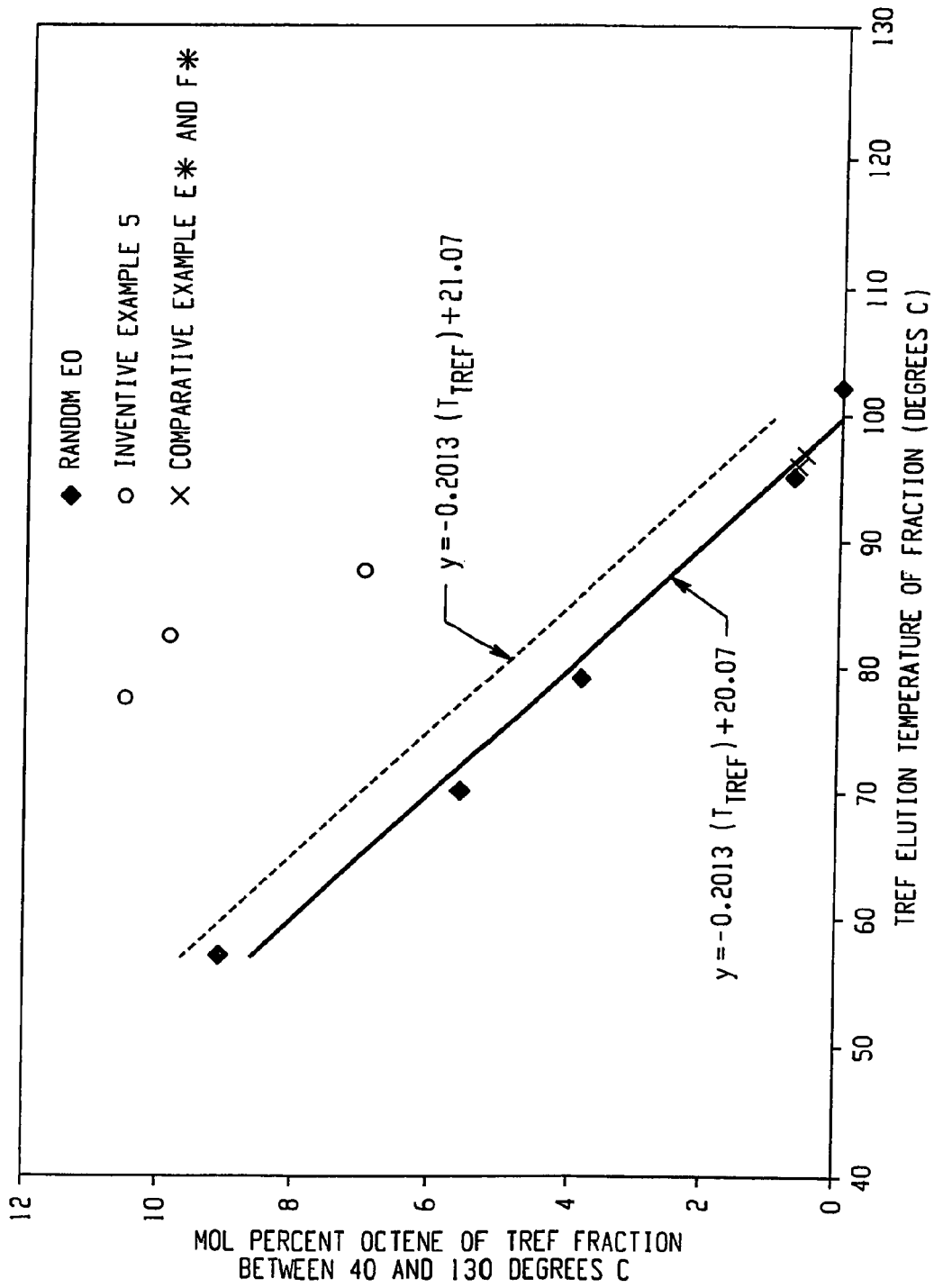
FIG. 4 is a plot of octene content of TREF fractionated ethylene/1-octene copolymer fractions versus TREF elution temperature of the fraction for the polymer of Example 5 (represented by the circles) and comparative polymer Comparative Examples E* and F* (represented by the "X" symbols). The diamonds represent traditional random ethylene/octene copolymers.

FIG. 4 graphically depicts an embodiment of the block interpolymers of ethylene and 1-octene where a plot of the comonomer content versus TREF elution temperature for several comparable ethylene/1-octene interpolymers (random copolymers) are fit to a line representing (−0.2013)T+ 20.07 (solid line). The line for the equation (−0.2013)T+ 21.07 is depicted by a dotted line. Also depicted are the comonomer contents for fractions of several block ethylene/ 1-octene interpolymers of the invention (multi-block copolymers). All of the block interpolymer fractions have significantly higher 1-octene content than either line at equivalent elution temperatures. This result is characteristic of the inventive interpolymer and is believed to be due to the presence of differentiated blocks within the polymer chains, having both crystalline and amorphous nature.

Figure 5:
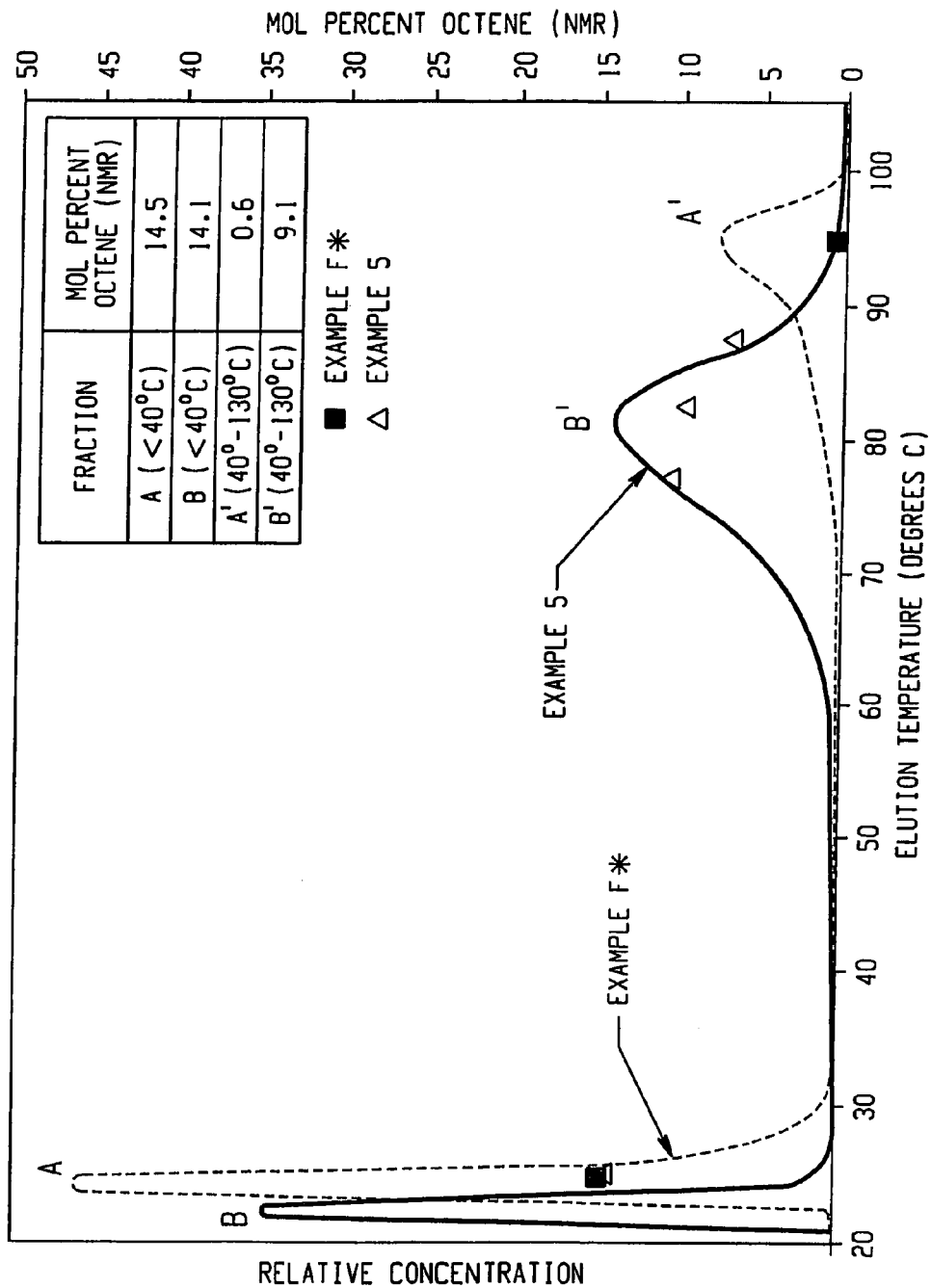
FIG. 5 is a plot of octene content of TREF fractionated ethylene/1-octene copolymer fractions versus TREF elution temperature of the fraction for the polymer of Example 5 (curve 1) and for polymer Comparative Examples F* (curve 2). The squares represent polymer Comparative Examples F*; and the triangles represent Example 5.

FIG. 5 graphically displays the TREF curve and comonomer contents of polymer fractions for Example 5 and comparative F to be discussed below. The peak eluting from 40 to 130° C., preferably from 60° C. to 95° C. for both polymers is fractionated into three parts, each part eluting over a temperature range of less than 10° C. Actual data for Example 5 is represented by triangles. The skilled artisan can appreciate that an appropriate calibration curve may be constructed for interpolymers containing different comonomers and a line used as a comparison fitted to the TREF values obtained from comparative interpolymers of the same monomers, preferably random copolymers made using a metallocene or other homogeneous catalyst composition. Inventive interpolymers are characterized by a molar comonomer content greater than the value determined from the calibration curve at the same TREF elution temperature, preferably at least 5 percent greater, more preferably at least 10 percent greater.

In addition to the above aspects and properties described herein, the inventive polymers can be characterized by one or more additional characteristics. In one aspect, the inventive polymer is an olefin interpolymer, preferably comprising ethylene and one or more copolymerizable comonomers in polymerized form, characterized by multiple blocks or segments of two or more polymerized monomer units differing in chemical or physical properties (blocked interpolymer), most preferably a multi-block copolymer, said block interpolymer having a molecular fraction which elutes between 40° C. and 130° C., when fractionated using TREF increments, characterized in that said fraction has a molar comonomer content higher, preferably at least 5 percent higher, more preferably at least 10, 15, 20 or 25 percent higher, than that of a comparable random ethylene interpolymer fraction eluting between the same temperatures, wherein said comparable random ethylene interpolymer comprises the same comonomer(s), preferably it is the same comonomer(s), and a melt index, density, and molar comonomer content (based on the whole polymer) within 10 percent of that of the blocked interpolymer. Preferably, the Mw/Mn of the comparable interpolymer is also within 10 percent of that of the blocked interpolymer and/or the comparable interpolymer has a total comonomer content within 10 weight percent of that of the blocked interpolymer.

Preferably, the above interpolymers are interpolymers of ethylene and at least one α-olefin, especially those interpolymers having a whole polymer density from about 0.855 to about 0.935 g/cm$^3$, and more especially for polymers having more than about 1 mole percent comonomer, the blocked interpolymer has a comonomer content of the TREF fraction eluting between 40 and 130° C. greater than or equal to the quantity (−0.1356)T+13.89, more preferably greater than or equal to the quantity (−0.1356)T+14.93, and most preferably greater than or equal to the quantity (−0.2013)T+21.07, where T is the numerical value of the peak ATREF elution temperature of the TREF fraction being compared, measured in ° C.

Preferably, for the above interpolymers of ethylene and at least one alpha-olefin, especially those interpolymers having a whole polymer density from about 0.855 to about 0.935 g/cm$^3$, and more especially for polymers having more than about 1 mole percent comonomer, the blocked interpolymer has a comonomer content of the TREF fraction eluting between 40 and 130° C. greater than or equal to the quantity (−0.2013)T+20.07, more preferably greater than or equal to the quantity (−0.2013)T+21.07, where T is the numerical value of the peak elution temperature of the TREF fraction being compared, measured in °C.

In still another aspect, the inventive polymer is an olefin interpolymer, preferably comprising ethylene and one or more copolymerizable comonomers in polymerized form, characterized by multiple blocks or segments of two or more polymerized monomer units differing in chemical or physical properties (blocked interpolymer), most preferably a multi-block copolymer, said block interpolymer having a molecular fraction which elutes between 40° C. and 130° C., when fractionated using TREF increments, characterized in that every fraction having a comonomer content of at least about 6 mole percent, has a melting point greater than about 100° C. For those fractions having a comonomer content from about 3 mole percent to about 6 mole percent, every fraction has a DSC melting point of about 110° C. or higher. More preferably, said polymer fractions, having at least 1 mol percent comonomer, has a DSC melting point that corresponds to the equation:

$$Tm \geq (-5.5926)(\text{mol percent comonomer in the fraction}) + 135.90.$$

In yet another aspect, the inventive polymer is an olefin interpolymer, preferably comprising ethylene and one or more copolymerizable comonomers in polymerized form, characterized by multiple blocks or segments of two or more polymerized monomer units differing in chemical or physical properties (blocked interpolymer), most preferably a multi-block copolymer, said block interpolymer having a molecular fraction which elutes between 40° C. and 130° C., when fractionated using TREF increments, characterized in that every fraction that has an ATREF elution temperature greater than or equal to about 76° C., has a melt enthalpy (heat of fusion) as measured by DSC, corresponding to the equation:

$$\text{Heat of fusion}(J/gm) \leq (3.1718)(\text{ATREF elution temperature in Celsius}) - 136.58.$$

The inventive block interpolymers have a molecular fraction which elutes between 40° C. and 130° C., when fractionated using TREF increments, characterized in that every fraction that has an ATREF elution temperature between 40° C. and less than about 76° C., has a melt enthalpy (heat of fusion) as measured by DSC, corresponding to the equation:

$$\text{Heat of fusion}(J/gm) \leq (1.1312)(\text{ATREF elution temperature in Celsius}) + 22.97.$$

ATREF Peak Comonomer Composition Measurement by Infra-Red Detector

The comonomer composition of the TREF peak can be measured using an IR4 infra-red detector available from Polymer Char, Valencia, Spain (http://www.polymerchar.com/).

The "composition mode" of the detector is equipped with a measurement sensor ($CH_2$) and composition sensor ($CH_3$) that are fixed narrow band infra-red filters in the region of 2800-3000 $cm^{-1}$. The measurement sensor detects the methylene ($CH_2$) carbons on the polymer (which directly relates to the polymer concentration in solution) while the composition sensor detects the methyl ($CH_3$) groups of the polymer. The mathematical ratio of the composition signal ($CH_3$) divided by the measurement signal ($CH_2$) is sensitive to the comonomer content of the measured polymer in solution and its response is calibrated with known ethylene alpha-olefin copolymer standards.

The detector when used with an ATREF instrument provides both a concentration ($CH_2$) and composition ($CH_3$) signal response of the eluted polymer during the TREF process. A polymer specific calibration can be created by measuring the area ratio of the $CH_3$ to $CH_2$ for polymers with known comonomer content (preferably measured by NMR). The comonomer content of an ATREF peak of a polymer can be estimated by applying the reference calibration of the ratio of the areas for the individual $CH_3$ and $CH_2$ response (i.e. area ratio $CH_3/CH_2$ versus comonomer content).

The area of the peaks can be calculated using a full width/half maximum (FWHM) calculation after applying the appropriate baselines to integrate the individual signal responses from the TREF chromatogram. The full width/half maximum calculation is based on the ratio of methyl to methylene response area [$CH_3/CH_2$] from the ATREF infra-red detector, wherein the tallest (highest) peak is identified from the base line, and then the FWHM area is determined. For a distribution measured using an ATREF peak, the FWHM area is defined as the area under the curve between T1 and T2, where T1 and T2 are points determined, to the left and right of the ATREF peak, by dividing the peak height by two, and then drawing a line horizontal to the base line, that intersects the left and right portions of the ATREF curve.

The application of infra-red spectroscopy to measure the comonomer content of polymers in this ATREF-infra-red method is, in principle, similar to that of GPC/FTIR systems as described in the following references: Markovich, Ronald P.; Hazlitt, Lonnie G.; Smith, Linley; "Development of gel-permeation chromatography-Fourier transform infrared spectroscopy for characterization of ethylene-based polyolefin copolymers", *Polymeric Materials Science and Engineering* (1991), 65, 98-100.; and Deslauriers, P. J.; Rohlfing, D. C.; Shieh, E. T.; "Quantifying short chain branching microstructures in ethylene-1-olefin copolymers using size exclusion chromatography and Fourier transform infrared spectroscopy (SEC-FTIR)", *Polymer* (2002), 43, 59-170, both of which are incorporated by reference herein in their entirety.

The ethylene/α-olefin interpolymers may also be characterized by an average block index, ABI, which is greater than zero and up to about 1.0 and a molecular weight distribution, $M_w/M_n$, greater than about 1.3. The average block index, ABI, is the weight average of the block index ("BI") for each of the polymer fractions obtained in preparative TREF (i.e., fractionation of a polymer by Temperature Rising Elution Fractionation) from 20° C. and 110° C., with an increment of 5° C. (although other temperature increments, such as 1° C., 2° C., 10° C., also can be used):

$$ABI = \Sigma(w_i BI_i)$$

where $BI_i$ is the block index for the ith fraction of the inventive ethylene/α-olefin interpolymer obtained in preparative TREF, and $w_i$ is the weight percentage of the ith fraction. Similarly, the square root of the second moment about the mean, hereinafter referred to as the second moment weight average block index, can be defined as follows.

Figure 9:
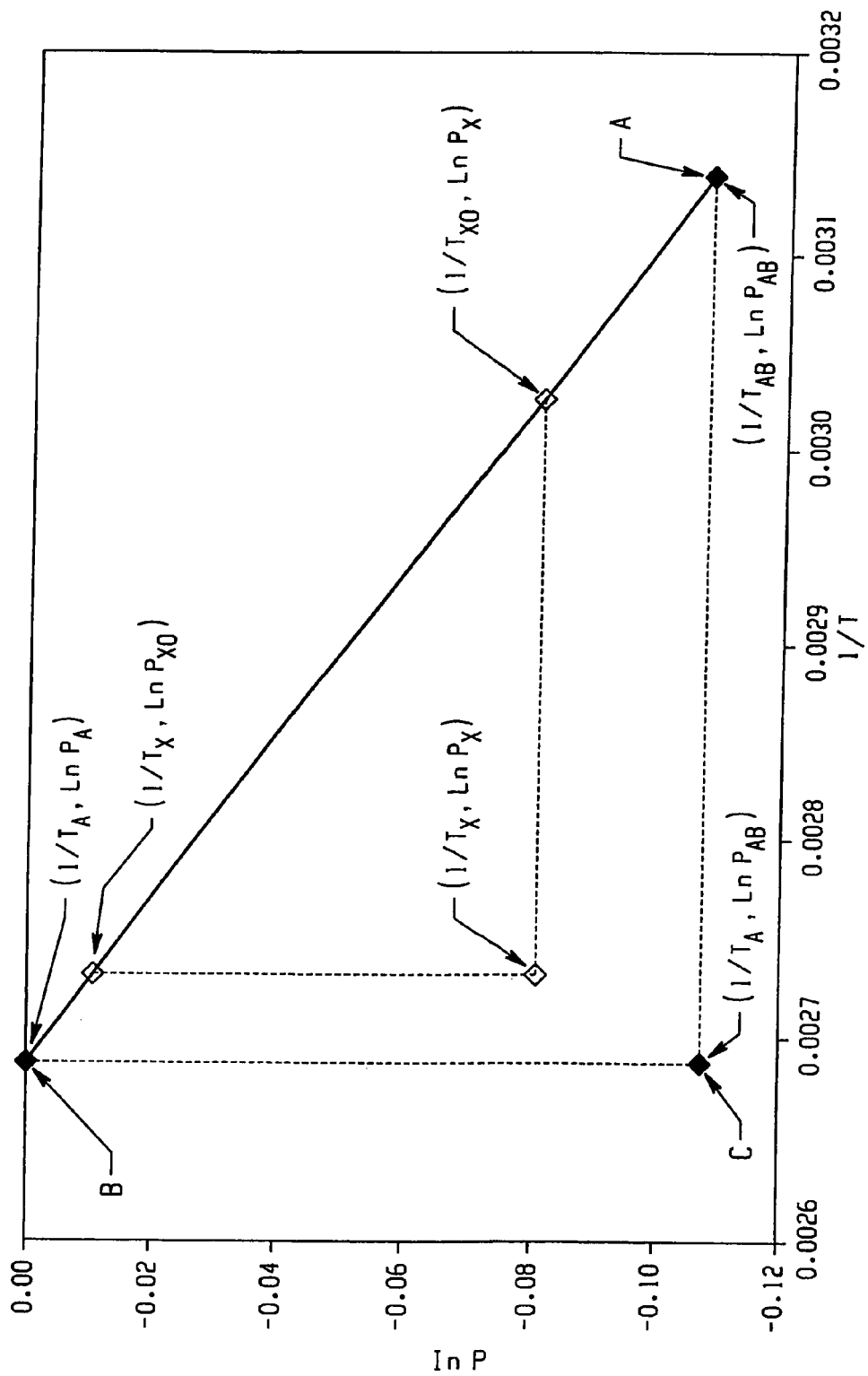
FIG. 9 is a plot constructed on the basis of the Flory equation for random ethylene/α-olefin copolymers to illustrate the definition of "block index." "A" represents the whole, perfect random copolymer; "B" represents a pure "hard segment"; and "C" represents the whole, perfect block copolymer having the same comonomer content as "A". A, B, and C define a triangular area within which most TREF fractions would fall.

$2^{nd}$ moment weight average $$BI = \sqrt{\frac{\Sigma(w_i(BI_i - ABI)^2)}{\frac{(N-1)\Sigma w_i}{N}}}$$

where N is defined as the number of fractions with $BI_i$ greater than zero. Referring to FIG. 9, for each polymer fraction, BI is defined by one of the two following equations (both of which give the same BI value):

$$BI = \frac{1/T_X - 1/T_{XO}}{1/T_A - 1/T_{AB}}$$

or $$BI = -\frac{LnP_X - LnP_{XO}}{LnP_A - LnP_{AB}}$$

where $T_X$ is the ATREF (i.e., analytical TREF) elution temperature for the ith fraction (preferably expressed in Kelvin), $P_X$ is the ethylene mole fraction for the ith fraction, which can be measured by NMR or IR as described below. $P_{AB}$ is the ethylene mole fraction of the whole ethylene/α-olefin interpolymer (before fractionation), which also can be measured by NMR or IR. $T_A$ and $P_A$ are the ATREF elution temperature and the ethylene mole fraction for pure "hard segments" (which refer to the crystalline segments of the interpolymer). As an approximation or for polymers where the "hard segment" composition is unknown, the $T_A$ and $P_A$ values are set to those for high density polyethylene homopolymer. For calculations performed herein, $T_A$ is 372 K, $P_A$ is 1.

Figure 8:
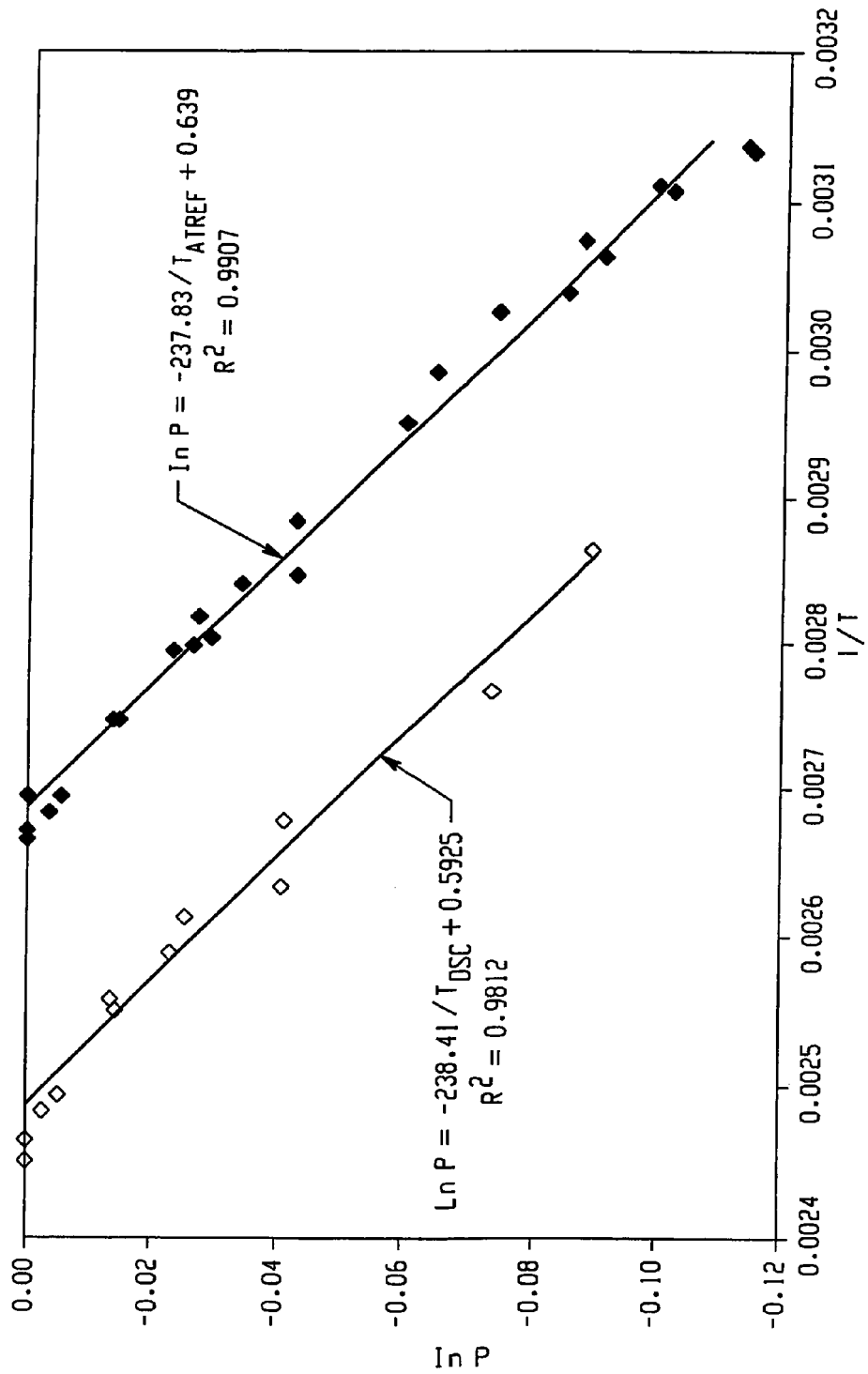
FIG. 8 is plot of natural log ethylene mole fraction for random ethylene/α-olefin copolymers as a function of the inverse of DSC peak melting temperature or ATREF peak temperature. The filled squares represent data points obtained from random homogeneously branched ethylene/α-olefin copolymers in ATREF; and the open squares represent data points obtained from random homogeneously branched ethylene/α-olefin copolymers in DSC. "P" is the ethylene mole fraction; "T" is the temperature in Kelvin.

$T_{AB}$ is the ATREF elution temperature for a random copolymer of the same composition (having an ethylene mole fraction of $P_{AB}$) and molecular weight as the inventive copolymer. $T_{AB}$ can be calculated from the mole fraction of ethylene (measured by NMR) using the following equation:

$$LnP_{AB} = \alpha/T_{AB} + \beta$$

where α and β are two constants which can be determined by a calibration using a number of well characterized preparative TREF fractions of a broad composition random copolymer and/or well characterized random ethylene copolymers with narrow composition. It should be noted that α and β may vary from instrument to instrument. Moreover, one would need to create an appropriate calibration curve with the polymer composition of interest, using appropriate molecular weight ranges and comonomer type for the preparative TREF fractions and/or random copolymers used to create the calibration. There is a slight molecular weight effect. If the calibration curve is obtained from similar molecular weight ranges, such effect would be essentially negligible. In some embodiments as illustrated in FIG. 8, random ethylene copolymers and/or preparative TREF fractions of random copolymers satisfy the following relationship:

$$LnP = -237.83/T_{ATREF} + 0.639$$

The above calibration equation relates the mole fraction of ethylene, P, to the analytical TREF elution temperature, $T_{ATREF}$, for narrow composition random copolymers and/or preparative TREF fractions of broad composition random copolymers. $T_{XO}$ is the ATREF temperature for a random copolymer of the same composition (i.e., the same comonomer type and content) and the same molecular weight and having an ethylene mole fraction of $P_X$. $T_{XO}$ can be calculated from $LnP_X = \alpha/T_{XO} + \beta$ from a measured $P_X$ mole fraction. Conversely, $P_{XO}$ is the ethylene mole fraction for a random copolymer of the same composition (i.e., the same comonomer type and content) and the same molecular weight and having an ATREF temperature of $T_X$, which can be calculated from $Ln P_{XO} = \alpha/T_X + \beta$ using a measured value of $T_X$.

Once the block index (BI) for each preparative TREF fraction is obtained, the weight average block index, ABI, for the whole polymer can be calculated. In some embodiments, ABI is greater than zero but less than about 0.4 or from about 0.1 to about 0.3. In other embodiments, ABI is greater than about 0.4 and up to about 1.0. Preferably, ABI should be in the range of from about 0.4 to about 0.7, from about 0.5 to about 0.7, or from about 0.6 to about 0.9. In some embodiments, ABI is in the range of from about 0.3 to about 0.9, from about 0.3 to about 0.8, or from about 0.3 to about 0.7, from about 0.3 to about 0.6, from about 0.3 to about 0.5, or from about 0.3 to about 0.4. In other embodiments, ABI is in the range of from about 0.4 to about 1.0, from about 0.5 to about 1.0, or from about 0.6 to about 1.0, from about 0.7 to about 1.0, from about 0.8 to about 1.0, or from about 0.9 to about 1.0.

Another characteristic of the inventive ethylene/α-olefin interpolymer is that the inventive ethylene/α-olefin interpolymer comprises at least one polymer fraction which can be obtained by preparative TREF, wherein the fraction has a block index greater than about 0.1 and up to about 1.0 and the polymer having a molecular weight distribution, $M_w/M_n$, greater than about 1.3. In some embodiments, the polymer fraction has a block index greater than about 0.6 and up to about 1.0, greater than about 0.7 and up to about 1.0, greater than about 0.8 and up to about 1.0, or greater than about 0.9 and up to about 1.0. In other embodiments, the polymer fraction has a block index greater than about 0.1 and up to about 1.0, greater than about 0.2 and up to about 1.0, greater than about 0.3 and up to about 1.0, greater than about 0.4 and up to about 1.0, or greater than about 0.4 and up to about 1.0. In still other embodiments, the polymer fraction has a block index greater than about 0.1 and up to about 0.5, greater than about 0.2 and up to about 0.5, greater than about 0.3 and up to about 0.5, or greater than about 0.4 and up to about 0.5. In yet other embodiments, the polymer fraction has a block index greater than about 0.2 and up to about 0.9, greater than about 0.3 and up to about 0.8, greater than about 0.4 and up to about 0.7, or greater than about 0.5 and up to about 0.6.

In addition to an average block index and individual fraction block indices, the ethylene/α-olefin interpolymers are characterized by one or more of the properties described as follows.

For copolymers of ethylene and an α-olefin, the inventive polymers preferably possess (1) a PDI of at least 1.3, more preferably at least 1.5, at least 1.7, or at least 2.0, and most preferably at least 2.6, up to a maximum value of 5.0, more preferably up to a maximum of 3.5, and especially up to a maximum of 2.7; (2) a heat of fusion of 80 J/g or less; (3) an ethylene content of at least 50 weight percent; (4) a glass transition temperature, $T_g$, of less than −25° C., more preferably less than −30° C., and/or (5) one and only one $T_m$.

Figure 6:
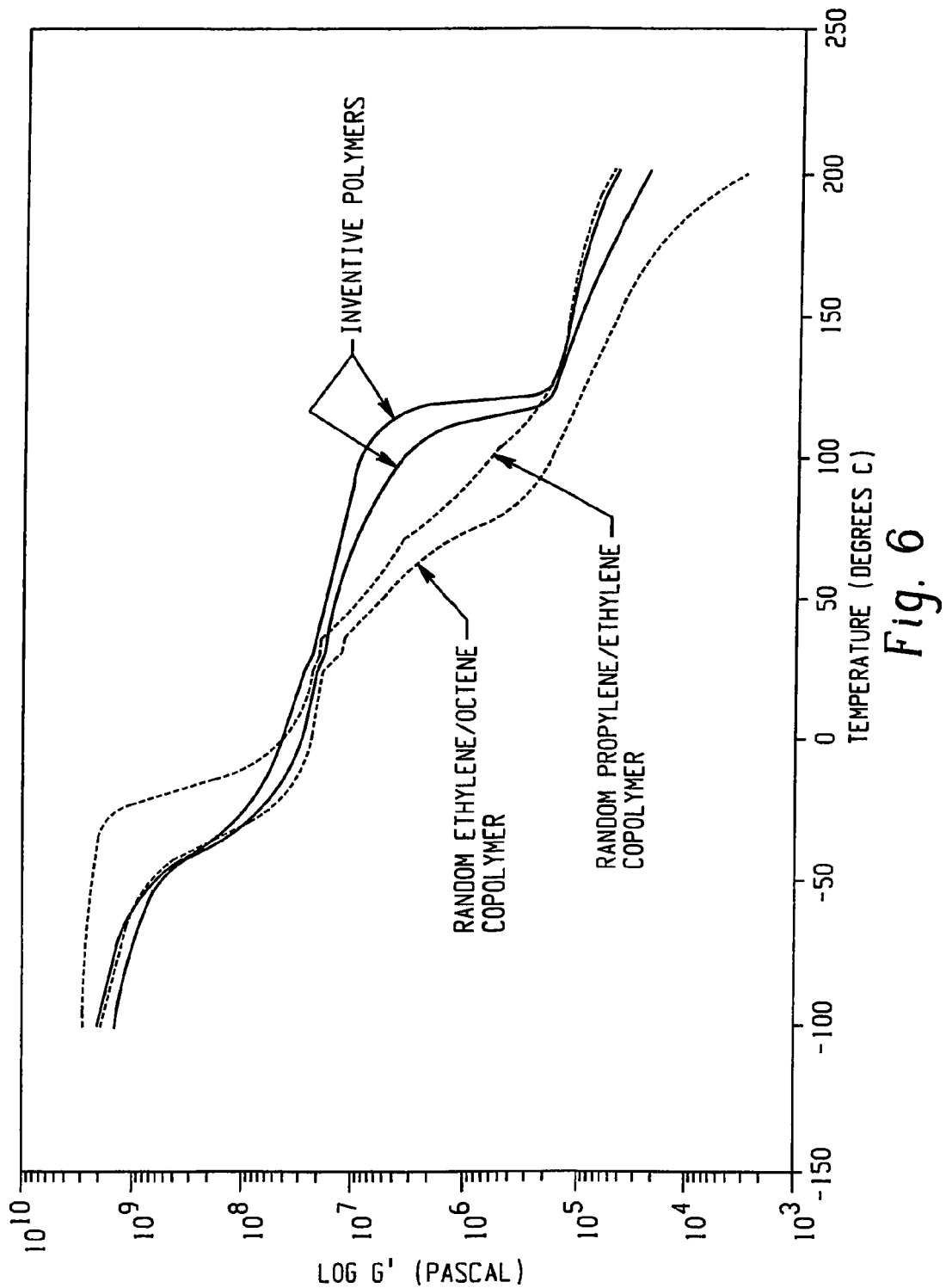
FIG. 6 is a graph of the log of storage modulus as a function of temperature for comparative ethylene/1-octene copolymer (curve 2) and propylene/ethylene copolymer (curve 3) and for two ethylene/1-octene block copolymers of the invention made with differing quantities of chain shuttling agent (curves 1).

Further, the inventive polymers can have, alone or in combination with any other properties disclosed herein, a storage modulus, G', such that log (G') is greater than or equal to 400 kPa, preferably greater than or equal to 1.0 MPa, at a temperature of 100° C. Moreover, the inventive polymers possess a relatively flat storage modulus as a function of temperature in the range from 0 to 100° C. (illustrated in FIG. 6) that is characteristic of block copolymers, and heretofore unknown for an olefin copolymer, especially a copolymer of ethylene and one or more $C_{3-8}$ aliphatic α-olefins. (By the term "relatively flat" in this context is meant that log G' (in Pascals) decreases by less than one order of magnitude between 50 and 100° C., preferably between 0 and 100° C.).

Figure 7:
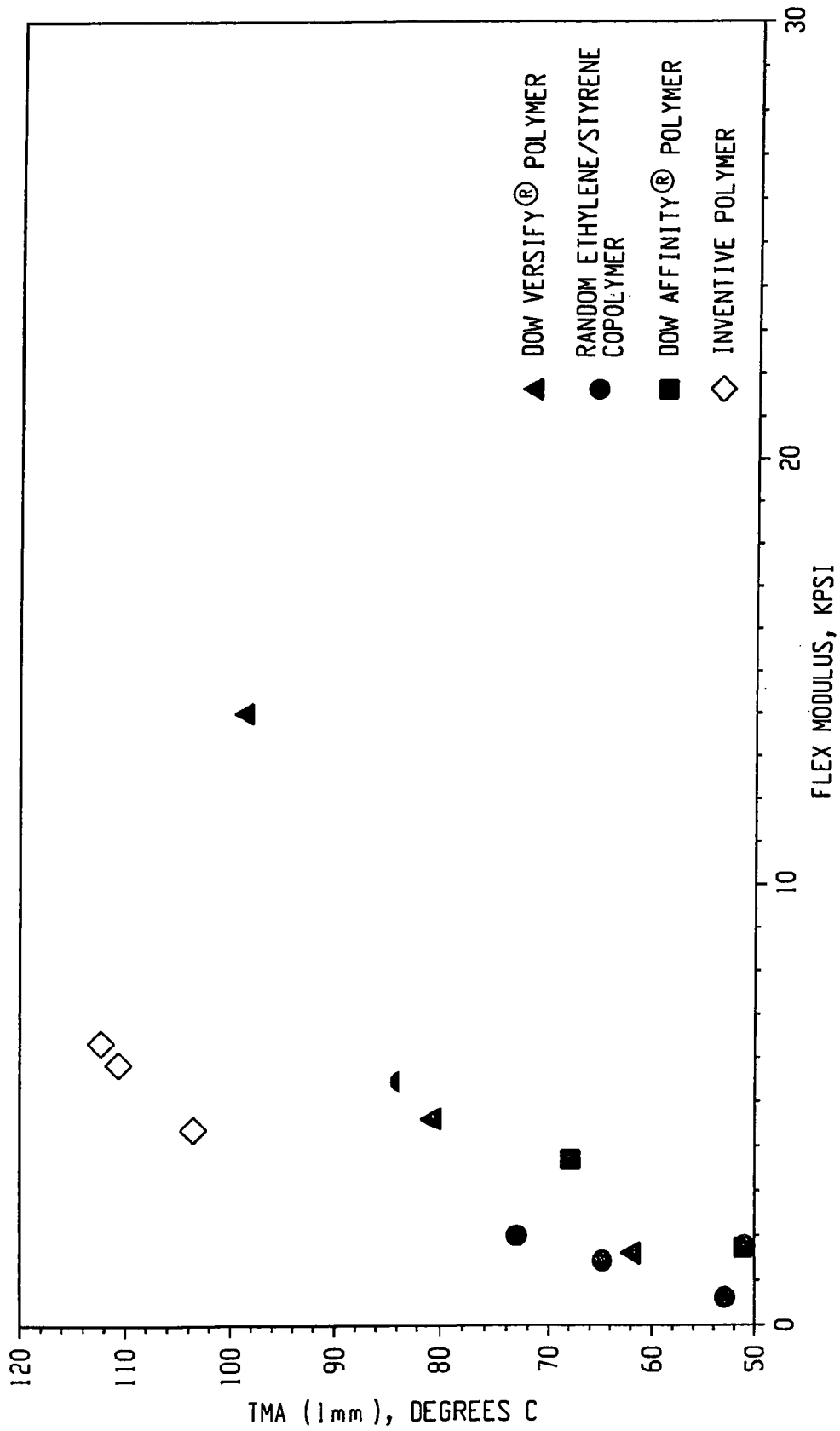
FIG. 7 shows a plot of TMA (1 mm) versus flex modulus for some inventive polymers (represented by the diamonds), as compared to some known polymers. The triangles represent various VERSIFY® polymers; the circles represent various random ethylene/styrene copolymers; and the squares represent various AFFINITY® polymers.

The inventive interpolymers may be further characterized by a thermomechanical analysis (TMA) penetration depth of 1 mm at a temperature of at least 90° C. as well as a flexural modulus (ASTM D790A) of from 3 kpsi (20 MPa) to 13 kpsi (90 MPa). Alternatively, the inventive interpolymers can have a thermomechanical analysis penetration depth of 1 mm at a temperature of at least 104° C. as well as a flexural modulus of at least 3 kpsi (20 MPa). They may be characterized as having an abrasion resistance (or volume loss) of less than 90 mm³. FIG. 7 shows the TMA (1 mm) versus flex modulus for the inventive polymers, as compared to other known polymers. The inventive polymers have significantly better flexibility-heat resistance balance than the other polymers.

Additionally, the ethylene/α-olefin interpolymers can have a melt index, $I_2$, from 0.01 to 2000 g/10 minutes, preferably from 0.01 to 1000 g/10 minutes, more preferably from 0.01 to 500 g/10 minutes, and especially from 0.01 to 100 g/10 minutes. In certain embodiments, the ethylene/α-olefin interpolymers have a melt index, $I_2$, from 0.01 to 10 g/10 minutes, from 0.5 to 50 g/10 minutes, from 1 to 30 g/10 minutes, from 1 to 6 g/10 minutes or from 0.3 to 10 g/10 minutes. In certain embodiments, the melt index for the ethylene/α-olefin polymers is 1 g/10 minutes, 5 g/10 minutes, 10 g/10 minutes, 15 g/10 minutes, 20 g/10 minutes or 24 g/10 minutes.

The polymers can have molecular weights, $M_w$, from 1,000 g/mole to 5,000,000 g/mole, preferably from 1000 g/mole to 1,000,000, more preferably from 10,000 g/mole to 500,000 g/mole, and especially from 10,000 g/mole to 300,000 g/mole. The density of the inventive polymers can be from 0.80 to 0.99 g/cm³ and preferably for ethylene containing polymers from 0.85 g/cm³ to 0.97 g/cm³. In certain embodiments, the density of the ethylene/α-olefin polymers ranges from 0.860 to 0.925 g/cm³ or 0.867 to 0.910 g/cm³. In certain embodiments, the density of the ethylene/α-olefin polymers is from about 0.860 to 0.900 g/cm³, preferably from about 0.860 to 0.885 g/cm³, more preferably from about 0.860 to 0.883 g/cm³, and most preferably from about 0.863 to 0.880 g/cm³.

The process of making the polymers has been disclosed in the following patent applications: U.S. Provisional Application No. 60/553,906, filed Mar. 17, 2004; U.S. Provisional Application No. 60/662,937, filed Mar. 17, 2005; U.S. Provisional Application No. 60/662,939, filed Mar. 17, 2005; U.S. Provisional Application No. 60/566,2938, filed Mar. 17, 2005; PCT Application No. PCT/US2005/008916, filed Mar. 17, 2005; PCT Application No. PCT/US2005/008915, filed Mar. 17, 2005; and PCT Application No. PCT/US2005/008917, filed Mar. 17, 2005, all of which are incorporated by reference herein in their entirety. For example, one such method comprises contacting ethylene and optionally one or more addition polymerizable monomers other than ethylene under addition polymerization conditions with a catalyst composition comprising:

the admixture or reaction product resulting from combining:

(A) a first olefin polymerization catalyst having a high comonomer incorporation index, (B) a second olefin polymerization catalyst having a comonomer incorporation index less than 90 percent, preferably less than 50 percent, most preferably less than 5 percent of the comonomer incorporation index of catalyst (A), and (C) a chain shuttling agent.

Representative catalysts and chain shuttling agent are as follows.

Catalyst (A1) is [N-(2,6-di(1-methylethyl)phenyl)amido) (2-isopropylphenyl)(α-naphthalen-2-diyl(6-pyridin-2-diyl) methane)]hafnium dimethyl, prepared according to the teachings of WO 03/40195, 2003US0204017, U.S. Ser. No. 10/429,024, filed May 2, 2003, and WO 04/24740.

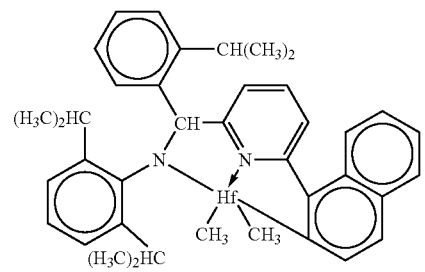

Catalyst (A2) is [N-(2,6-di(1-methylethyl)phenyl)amido) (2-methylphenyl)(1,2-phenylene-(6-pyridin-2-diyl)methane)]hafnium dimethyl, prepared according to the teachings of WO 03/40195, 2003US0204017, U.S. Ser. No. 10/429, 024, filed May 2, 2003, and WO 04/24740.

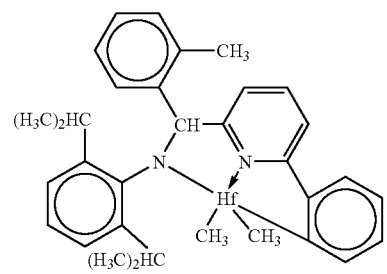

Catalyst (A3) is bis[N,N'''-(2,4,6-tri(methylphenyl)amido) ethylenediamine]hafnium dibenzyl.

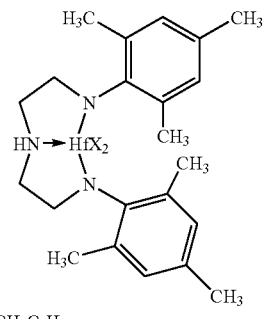

X= CH₂C₆H₅

Catalyst (A4) is bis((2-oxoyl-3-(dibenzo-1H-pyrrole-1-yl)-5-(methyl)phenyl)-2-phenoxymethyl)cyclohexane-1,2-diyl zirconium (IV) dibenzyl, prepared substantially according to the teachings of US-A-2004/0010103.

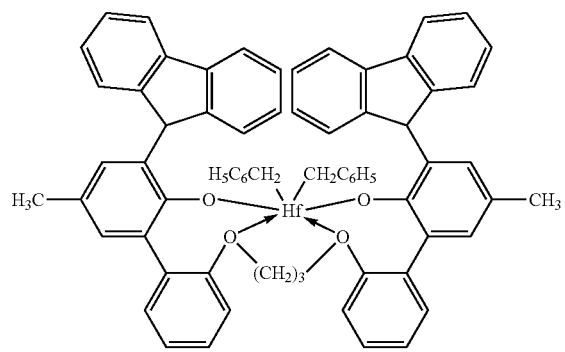

Catalyst (B1) is 1,2-bis-(3,5-di-t-butylphenylene)(1-(N-(1-methylethyl)immino)methyl)(2-oxoyl)zirconium dibenzyl

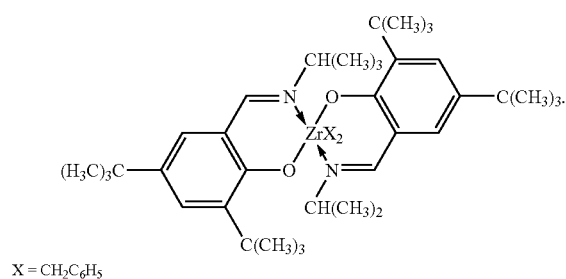

X = CH₂C₆H₅

Catalyst (B2) is 1,2-bis-(3,5-di-t-butylphenylene)(1-(N-(2-methylcyclohexyl)-immino)methyl)(2-oxoyl)zirconium dibenzyl

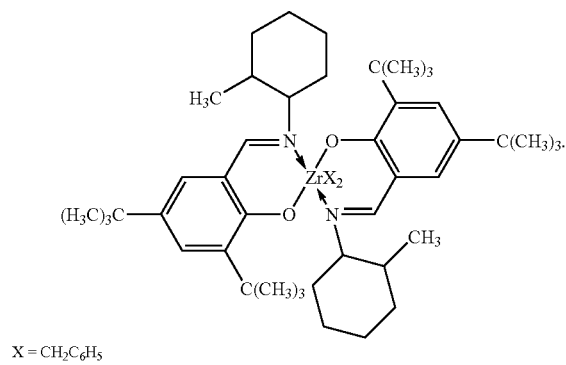

X = CH₂C₆H₅

Catalyst (C1) is (t-butylamido)dimethyl(3-N-pyrrolyl-1,2,3,3a,7a-η-inden-1-yl)silanetitanium dimethyl prepared substantially according to the techniques of U.S. Pat. No. 6,268,444:

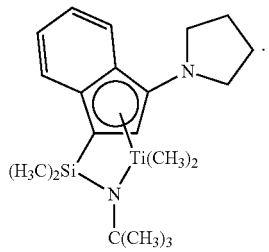

Catalyst (C2) is (t-butylamido)di(4-methylphenyl)(2-methyl-1,2,3,3a,7a-η-inden-1-yl)silanetitanium dimethyl prepared substantially according to the teachings of US-A-2003/004286:

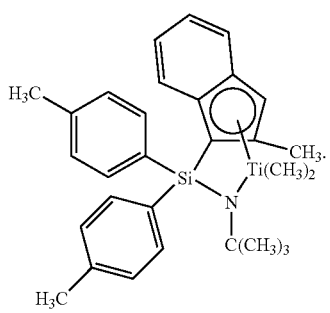

Catalyst (C3) is (t-butylamido)di(4-methylphenyl)(2-methyl-1,2,3,3a,8a-η-s-indacen-1-yl)silanetitanium dimethyl prepared substantially according to the teachings of US-A-2003/004286:

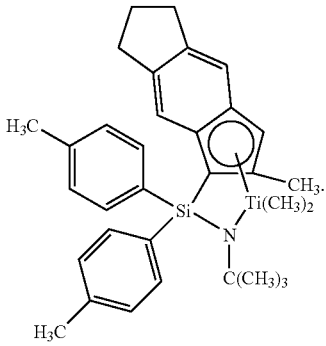

Catalyst (D1) is bis(dimethyldisiloxane)(indene-1-yl)zirconium dichloride available from Sigma-Aldrich:

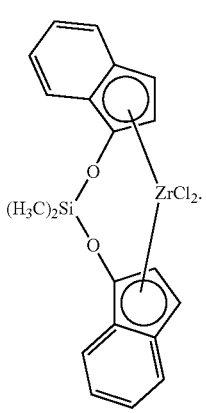

Shuttling Agents The shuttling agents employed include diethylzinc, di(i-butyl)zinc, di(n-hexyl)zinc, triethylaluminum, trioctylaluminum, triethylgallium, i-butylaluminum bis(dimethyl(t-butyl)siloxane), i-butylaluminum bis(di(trimethylsilyl)amide), n-octylaluminum di(pyridine-2-methoxide), bis(n-octadecyl)i-butylaluminum, i-butylaluminum bis(di(n-pentyl)amide), n-octylaluminum bis(2,6-di-t-butylphenoxide, n-octylaluminum di(ethyl(1-naphthyl)amide), ethylaluminum bis(t-butyldimethylsiloxide), ethylaluminum di(bis(trimethylsilyl)amide), ethylaluminum bis(2,3,6,7-dibenzo-1-azacycloheptaneamide), n-octylaluminum bis(2,3,6,7-dibenzo-1-azacycloheptaneamide), n-octylaluminum bis(dimethyl(t-butyl)siloxide, ethylzinc (2,6-diphenylphenoxide), and ethylzinc (t-butoxide).

Preferably, the foregoing process takes the form of a continuous solution process for forming block copolymers, especially multi-block copolymers, preferably linear multi-block copolymers of two or more monomers, more especially ethylene and a $C_{3-20}$ olefin or cycloolefin, and most especially ethylene and a $C_{4-20}$ α-olefin, using multiple catalysts that are incapable of interconversion. That is, the catalysts are chemically distinct. Under continuous solution polymerization conditions, the process is ideally suited for polymerization of mixtures of monomers at high monomer conversions. Under these polymerization conditions, shuttling from the chain shuttling agent to the catalyst becomes advantaged compared to chain growth, and multi-block copolymers, especially linear multi-block copolymers are formed in high efficiency.

The inventive interpolymers may be differentiated from conventional, random copolymers, physical blends of polymers, and block copolymers prepared via sequential monomer addition, fluxional catalysts, anionic or cationic living polymerization techniques. In particular, compared to a random copolymer of the same monomers and monomer content at equivalent crystallinity or modulus, the inventive interpolymers have better (higher) heat resistance as measured by melting point, higher TMA penetration temperature, higher high-temperature tensile strength, and/or higher high-temperature torsion storage modulus as determined by dynamic mechanical analysis. Compared to a random copolymer containing the same monomers and monomer content, the inventive interpolymers have lower compression set, particularly at elevated temperatures, lower stress relaxation, higher creep resistance, higher tear strength, higher blocking resistance, faster setup due to higher crystallization (solidification) temperature, higher recovery (particularly at elevated temperatures), better abrasion resistance, higher retractive force, and better oil and filler acceptance.

The inventive interpolymers also exhibit a unique crystallization and branching distribution relationship. That is, the inventive interpolymers have a relatively large difference between the tallest peak temperature measured using CRYSTAF and DSC as a function of heat of fusion, especially as compared to random copolymers containing the same monomers and monomer level or physical blends of polymers, such as a blend of a high density polymer and a lower density copolymer, at equivalent overall density. It is believed that this unique feature of the inventive interpolymers is due to the unique distribution of the comonomer in blocks within the polymer backbone. In particular, the inventive interpolymers may comprise alternating blocks of differing comonomer content (including homopolymer blocks). The inventive interpolymers may also comprise a distribution in number and/or block size of polymer blocks of differing density or comonomer content, which is a Schultz-Flory type of distribution. In addition, the inventive interpolymers also have a unique peak melting point and crystallization temperature profile that is substantially independent of polymer density, modulus, and morphology. In a preferred embodiment, the microcrystalline order of the polymers demonstrates characteristic spherulites and lamellae that are distinguishable from random or block copolymers, even at PDI values that are less than 1.7, or even less than 1.5, down to less than 1.3.

Furthermore, by combining ethylene α-olefins with styrenic block copolymers, disadvantages associated with using styrenic block copolymer formulations may be mitigated. For example, thermal instability is associated with certain styrenic block copolymers. One example is styrene-isoprene-styrene (SIS). If processed at excessively high temperatures, SIS is known to undergo chain scission. This can result in significant decreases in viscosity and loss of mechanical properties. Another example is styrene-butadiene-styrene (SBS). If processed at excessively high temperatures, SBS is known to undergo cross-linking. This can result in significant increases in viscosity and gel formation. As a result, limitations such as these can result in disadvantaged performance. Formulation with ethylene α-olefins can mitigate these disadvantages.

Moreover, the inventive interpolymers may be prepared using techniques to influence the degree or level of blockiness. That is, the amount of comonomer and length of each polymer block or segment can be altered by controlling the ratio and type of catalysts and shuttling agent as well as the temperature of the polymerization, and other polymerization variables. A surprising benefit of this phenomenon is the discovery that as the degree of blockiness is increased, the optical properties, tear strength, and high temperature recovery properties of the resulting polymer are improved. In particular, haze decreases while clarity, tear strength, and high temperature recovery properties increase as the average number of blocks in the polymer increases. By selecting shuttling agents and catalyst combinations having the desired chain transferring ability (high rates of shuttling with low levels of chain termination) other forms of polymer termination are effectively suppressed. Accordingly, little if any β-hydride elimination is observed in the polymerization of ethylene/α-olefin comonomer mixtures according to embodiments of the invention, and the resulting crystalline blocks are highly, or substantially completely, linear, possessing little or no long chain branching.

Polymers with highly crystalline chain ends can be selectively prepared in accordance with embodiments of the invention. In elastomer applications, reducing the relative quantity of polymer that terminates with an amorphous block reduces the intermolecular dilutive effect on crystalline regions. This result can be obtained by choosing chain shuttling agents and catalysts having an appropriate response to hydrogen or other chain terminating agents. Specifically, if the catalyst which produces highly crystalline polymer is more susceptible to chain termination (such as by use of hydrogen) than the catalyst responsible for producing the less crystalline polymer segment (such as through higher comonomer incorporation, regio-error, or atactic polymer formation), then the highly crystalline polymer segments will preferentially populate the terminal portions of the polymer. Not only are the resulting terminated groups crystalline, but upon termination, the highly crystalline polymer forming catalyst site is once again available for reinitiation of polymer formation. The initially formed polymer is therefore another highly crystalline polymer segment. Accordingly, both ends of the resulting multi-block copolymer are preferentially highly crystalline.

The ethylene α-olefin interpolymers used in the embodiments of the invention are preferably interpolymers of ethylene with at least one $C_3$-$C_{20}$ α-olefin. Copolymers of ethylene and a $C_3$-$C_{20}$ α-olefin are especially preferred. The interpolymers may further comprise $C_4$-$C_{18}$ diolefin and/or alkenylbenzene. Suitable unsaturated comonomers useful for polymerizing with ethylene include, for example, ethylenically unsaturated monomers, conjugated or nonconjugated dienes, polyenes, alkenylbenzenes, etc. Examples of such comonomers include $C_3$-$C_{20}$ α-olefins such as propylene, isobutylene, 1-butene, 1-hexene, 1-pentene, 4-methyl-1-pentene, 1-heptene, 1-octene, 1-nonene, 1-decene, and the like. 1-Butene and 1-octene are especially preferred. Other suitable monomers include styrene, halo- or alkyl-substituted styrenes, vinylbenzocyclobutane, 1,4-hexadiene, 1,7-octadiene, and naphthenics (e.g., cyclopentene, cyclohexene and cyclooctene).

While ethylene/α-olefin interpolymers are preferred polymers, other ethylene/olefin polymers may also be used. Olefins as used herein refer to a family of unsaturated hydrocarbon-based compounds with at least one carbon-carbon double bond. Depending on the selection of catalysts, any olefin may be used in embodiments of the invention. Preferably, suitable olefins are $C_3$-$C_{20}$ aliphatic and aromatic compounds containing vinylic unsaturation, as well as cyclic compounds, such as cyclobutene, cyclopentene, dicyclopentadiene, and norbornene, including but not limited to, norbornene substituted in the 5 and 6 position with $C_1$-$C_{20}$ hydrocarbyl or cyclohydrocarbyl groups. Also included are mixtures of such olefins as well as mixtures of such olefins with $C_4$-$C_{40}$ diolefin compounds.

Examples of olefin monomers include, but are not limited to propylene, isobutylene, 1-butene, 1-pentene, 1-hexene, 1-heptene, 1-octene, 1-nonene, 1-decene, and 1-dodecene, 1-tetradecene, 1-hexadecene, 1-octadecene, 1-eicosene, 3-methyl-1-butene, 3-methyl-1-pentene, 4-methyl-1-pentene, 4,6-dimethyl-1-heptene, 4-vinylcyclohexene, vinylcyclohexane, norbornadiene, ethylidene norbornene, cyclopentene, cyclohexene, dicyclopentadiene, cyclooctene, $C_4$-$C_{40}$ dienes, including but not limited to 1,3-butadiene, 1,3-pentadiene, 1,4-hexadiene, 1,5-hexadiene, 1,7-octadiene, 1,9-decadiene, other $C_4$-$C_{40}$ α-olefins, and the like. In certain embodiments, the α-olefin is propylene, 1-butene, 1-pentene, 1-hexene, 1-octene or a combination thereof. Although any hydrocarbon containing a vinyl group potentially may be used in embodiments of the invention, practical issues such as monomer availability, cost, and the ability to conveniently remove unreacted monomer from the resulting polymer may become more problematic as the molecular weight of the monomer becomes too high.

The polymerization processes described herein are well suited for the production of olefin polymers comprising monovinylidene aromatic monomers including styrene, o-methyl styrene, p-methyl styrene, t-butylstyrene, and the like. In particular, interpolymers comprising ethylene and styrene can be prepared by following the teachings herein. Optionally, copolymers comprising ethylene, styrene and a $C_3$-$C_{20}$ alpha olefin, optionally comprising a $C_4$-$C_{20}$ diene, having improved properties can be prepared.

Suitable non-conjugated diene monomers can be a straight chain, branched chain or cyclic hydrocarbon diene having from 6 to 15 carbon atoms. Examples of suitable non-conjugated dienes include, but are not limited to, straight chain acyclic dienes, such as 1,4-hexadiene, 1,6-octadiene, 1,7-octadiene, 1,9-decadiene, branched chain acyclic dienes, such as 5-methyl-1,4-hexadiene; 3,7-dimethyl-1,6-octadiene; 3,7-dimethyl-1,7-octadiene and mixed isomers of dihydromyricene and dihydroocinene, single ring alicyclic dienes, such as 1,3-cyclopentadiene; 1,4-cyclohexadiene; 1,5-cyclooctadiene and 1,5-cyclododecadiene, and multi-ring alicyclic fused and bridged ring dienes, such as tetrahydroindene, methyl tetrahydroindene, dicyclopentadiene, bicyclo-(2,2,1)-hepta-2,5-diene; alkenyl, alkylidene, cycloalkenyl and cycloalkylidene norbornenes, such as 5-methylene-2-norbornene (MNB); 5-propenyl-2-norbornene, 5-isopropylidene-2-norbornene, 5-(4-cyclopentenyl)-2-norbornene, 5-cyclohexylidene-2-norbornene, 5-vinyl-2-norbornene, and norbornadiene. Of the dienes typically used to prepare EPDMs, the particularly preferred dienes are 1,4-hexadiene (HD), 5-ethylidene-2-norbornene (ENB), 5-vinylidene-2-norbornene (VNB), 5-methylene-2-norbornene (MNB), and dicyclopentadiene (DCPD). The especially preferred dienes are 5-ethylidene-2-norbornene (ENB) and 1,4-hexadiene (HD).

One class of desirable polymers that can be made in accordance with embodiments of the invention are elastomeric interpolymers of ethylene, a $C_3$-$C_{20}$ α-olefin, especially propylene, and optionally one or more diene monomers. Preferred α-olefins for use in this embodiment of the present invention are designated by the formula $CH_2$=CHR*, where R* is a linear or branched alkyl group of from 1 to 12 carbon atoms. Examples of suitable α-olefins include, but are not limited to, propylene, isobutylene, 1-butene, 1-pentene, 1-hexene, 4-methyl-1-pentene, and 1-octene. A particularly preferred α-olefin is propylene. The propylene based polymers are generally referred to in the art as EP or EPDM polymers. Suitable dienes for use in preparing such polymers, especially multi-block EPDM type polymers include conjugated or non-conjugated, straight or branched chain-, cyclic- or polycyclic-dienes comprising from 4 to 20 carbons. Preferred dienes include 1,4-pentadiene, 1,4-hexadiene, 5-ethylidene-2-norbornene, dicyclopentadiene, cyclohexadiene, and 5-butylidene-2-norbornene. A particularly preferred diene is 5-ethylidene-2-norbornene.

Because the diene containing polymers comprise alternating segments or blocks containing greater or lesser quantities of the diene (including none) and α-olefin (including none), the total quantity of diene and α-olefin may be reduced without loss of subsequent polymer properties. That is, because the diene and α-olefin monomers are preferentially incorporated into one type of block of the polymer rather than uniformly or randomly throughout the polymer, they are more efficiently utilized and subsequently the crosslink density of the polymer can be better controlled. Such crosslinkable elastomers and the cured products have advantaged properties, including higher tensile strength and better elastic recovery.

In some embodiments, the inventive interpolymers made with two catalysts incorporating differing quantities of comonomer have a weight ratio of blocks formed thereby from 95:5 to 5:95. The elastomeric polymers desirably have an ethylene content of from 20 to 90 percent, a diene content of from 0.1 to 10 percent, and an α-olefin content of from 10 to 80 percent, based on the total weight of the polymer. Further preferably, the multi-block elastomeric polymers have an ethylene content of from 60 to 90 percent, a diene content of from 0.1 to 10 percent, and an α-olefin content of from 10 to 40 percent, based on the total weight of the polymer. Preferred polymers are high molecular weight polymers, having a weight average molecular weight (Mw) from 10,000 to about 2,500,000, preferably from 20,000 to 500,000, more preferably from 20,000 to 350,000, and a polydispersity less than 3.5, more preferably less than 3.0, and a Mooney viscosity (ML (1+4) 125° C.) from 1 to 250. More preferably, such polymers have an ethylene content from 65 to 75 percent, a diene content from 0 to 6 percent, and an α-olefin content from 20 to 35 percent based on the total weight of the polymer.

The ethylene/α-olefin interpolymers can be functionalized by incorporating at least one functional group in its polymer structure. Exemplary functional groups may include, for example, ethylenically unsaturated mono- and di-functional carboxylic acids, ethylenically unsaturated mono- and di-functional carboxylic acid anhydrides, salts thereof and esters thereof. Such functional groups may be grafted to an ethylene/α-olefin interpolymer, or it may be copolymerized with ethylene and an optional additional comonomer to form an interpolymer of ethylene, the functional comonomer and optionally other comonomer(s). Means for grafting functional groups onto polyethylene are described for example in U.S. Pat. Nos. 4,762,890, 4,927,888, and 4,950,541, the disclosures of these patents are incorporated herein by reference in their entirety. One particularly useful functional group is maleic anhydride.

The amount of the functional group present in the functional interpolymer can vary. The functional group can typically be present in a copolymer-type functionalized interpolymer in an amount of at least about 1.0 weight percent, preferably at least about 5 weight percent, and more preferably at least about 7 weight percent. The functional group will typically be present in a copolymer-type functionalized interpolymer in an amount less than about 40 weight percent, preferably less than about 30 weight percent, and more preferably less than about 25 weight percent.

The amount of the ethylene/α-olefin interpolymer in the polymer blend disclosed herein can be from about 5 to about 95 wt %, from about 10 to about 90 wt %, from about 20 to about 80 wt %, from about 30 to about 70 wt %, from about 10 to about 50 wt %, from about 50 to about 90 wt %, from about 60 to about 90 wt %, or from about 70 to about 90 wt % of the total weight of the polymer blend.

More on Block Index

Random copolymers satisfy the following relationship. See P. J. Flory, *Trans. Faraday Soc.*, 51, 848 (1955), which is incorporated by reference herein in its entirety.

$$\frac{1}{T_m} - \frac{1}{T_m^0} = -\left(\frac{R}{\Delta H_u}\right) \ln P \quad (1)$$

In Equation 1, the mole fraction of crystallizable monomers, P, is related to the melting temperature, $T_m$, of the copolymer and the melting temperature of the pure crystallizable homopolymer, $T_m^0$. The equation is similar to the relationship for the natural logarithm of the mole fraction of ethylene as a function of the reciprocal of the ATREF elution temperature (° K) as shown in FIG. 8 for various homogeneously branched copolymers of ethylene and olefins.

As illustrated in FIG. 8, the relationship of ethylene mole fraction to ATREF peak elution temperature and DSC melting temperature for various homogeneously branched copolymers is analogous to Flory's equation. Similarly, preparative TREF fractions of nearly all random copolymers and random copolymer blends likewise fall on this line, except for small molecular weight effects.

According to Flory, if P, the mole fraction of ethylene, is equal to the conditional probability that one ethylene unit will precede or follow another ethylene unit, then the polymer is random. On the other hand if the conditional probability that any 2 ethylene units occur sequentially is greater than P, then the copolymer is a block copolymer. The remaining case where the conditional probability is less than P yields alternating copolymers.

The mole fraction of ethylene in random copolymers primarily determines a specific distribution of ethylene segments whose crystallization behavior in turn is governed by the minimum equilibrium crystal thickness at a given temperature. Therefore, the copolymer melting and TREF crystallization temperatures of the inventive block copolymers are related to the magnitude of the deviation from the random relationship in FIG. 8, and such deviation is a useful way to quantify how "blocky" a given TREF fraction is relative to its random equivalent copolymer (or random equivalent TREF fraction). The term "blocky" refers to the extent a particular polymer fraction or polymer comprises blocks of polymerized monomers or comonomers. There are two random equivalents, one corresponding to constant temperature and one corresponding to constant mole fraction of ethylene. These form the sides of a right triangle as shown in FIG. 9, which illustrates the definition of the block index.

In FIG. 9, the point $(T_X, P_X)$ represents a preparative TREF fraction, where the ATREF elution temperature, $T_X$, and the NMR ethylene mole fraction, $P_X$, are measured values. The ethylene mole fraction of the whole polymer, $P_{AB}$, is also measured by NMR. The "hard segment" elution temperature and mole fraction, $(T_A, P_A)$, can be estimated or else set to that of ethylene homopolymer for ethylene copolymers. The $T_{AB}$ value corresponds to the calculated random copolymer equivalent ATREF elution temperature based on the measured $P_{AB}$. From the measured ATREF elution temperature, $T_X$, the corresponding random ethylene mole fraction, $P_{XO}$, can also be calculated. The square of the block index is defined to be the ratio of the area of the $(P_X, T_X)$ triangle and the $(T_A, P_{AB})$ triangle. Since the right triangles are similar, the ratio of areas is also the squared ratio of the distances from $(T_A, P_{AB})$ and $(T_X, P_X)$ to the random line. In addition, the similarity of the right triangles means the ratio of the lengths of either of the corresponding sides can be used instead of the areas.

$$BI = \frac{1/T_X - 1/T_{XO}}{1/T_A - 1/T_{AB}}$$

or $$BI = -\frac{LnP_X - LnP_{XO}}{LnP_A - LnP_{AB}}$$

It should be noted that the most perfect block distribution would correspond to a whole polymer with a single eluting fraction at the point $(T_A, P_{AB})$, because such a polymer would preserve the ethylene segment distribution in the "hard segment", yet contain all the available octene (presumably in runs that are nearly identical to those produced by the soft segment catalyst). In most cases, the "soft segment" will not crystallize in the ATREF (or preparative TREF).

The Compositions of the Present Invention

The compositions of matter of the present invention comprise the ethylene/α-olefin interpolymer described previously and a styrenic block copolymer. While any density ethylene/α-olefin interpolymer may be useful, in general, the lower the density, the more elastic the polymer will be. It is particularly preferred that the density of the interpolymer be from about 0.85 to 0.900 g/cm³, preferably from about 0.855 to 0.885 g/cm³, more preferably from about 0.860 to 0.883 g/cm³, and most preferably from about 0.863 to 0.880 g/cm³.

The Styrenic Block Copolymer

Examples of styrenic block copolymers suitable for the invention are described in but is not limited to EP0712892 B1; WO204041538 A1; U.S. Pat. No. 6,582,829 B1; US 2004/0087235 A1; US 2004/0122408 A1; US 2004/0122409 A1; U.S. Pat. No. 4,789,699; U.S. Pat. No. 5,093,422; U.S. Pat. No. 5,332,613; U.S. Pat. No. 6,916,750 B2; US 2002/0052585 A1; U.S. Pat. No. 6,323,389 B1; and U.S. Pat. No. 5,169,706, which are incorporated by reference for their teachings regarding styrenic block copolymers.

Styrenic block copolymers that may be suitable for use in the invention include polymers such as styrene-ethylenepropylene-styrene (SEPS), styrene-ethylenepropylene-styrene-ethylenepropylene SEPSEP), hydrogenated polybutadiene polymers such as styrene-ethylenebutylene styrene (SEBS), styrene-ethylenebutylene-styrene-ethylenebutylene (SEB-SEB), styrene butadiene-styrene (SBS), styrene-isoprene-styrene (SIS), and hydrogenated poly isoprene/butadiene polymer such as styrene-ethylene-ethylenepropylene-styrene (SEEPS).

In general, styrenic block copolymers suitable for the invention have at least two monoalkenyl arene blocks, preferably two polystyrene blocks, separated by a block of saturated conjugated diene comprising less than 20% residual ethylenic unsaturation, preferably a saturated polybutadiene block. The preferred styrenic block copolymers have a linear structure although branched or radial polymers or functionalized block copolymers make useful compounds.

Typically, polystyrene-saturated polybutadiene-polystyrene (S-EB-S) (S is styrene, E is ethylene, and B is butylene) and polystyrene-saturated polyisoprene-polystyrene (S-EP- S) (P is propylene) block copolymers comprise polystyrene endblocks having a number average molecular weight from 5,000 to 35,000 and saturated polybutadiene or saturated polyisoprene midblocks having a number average molecular weight from 20,000 to 170,000. The saturated polybutadiene blocks preferably have from 35% to 55% 1, 2-configuration and the saturated polyisoprene blocks preferably have greater than 85% 1, 4-configuration.

The total number average molecular weight of the styrenic block copolymer is preferably from 30,000 to 250,000 if the copolymer has a linear structure. Such block copolymers typically have an average polystyrene content from 10% by weight to 35% by weight.

A S-EB-S block copolymer useful in a particularly preferred aspect of the present invention is available from KRATON Polymers LLC (Houston, Tex.) and has a number average molecular weight of 50,000 grams per mole with polystyrene endblocks each having a number average molecular weight of 7,200 grams per mole and polystyrene content of 30% by weight.

Styrenic block copolymers may be prepared by methods known to one of ordinary skill in the art. For example, the styrenic block copolymers may be manufactured using free-radical, cationic and anionic initiators or polymerization catalysts. Such polymers may be prepared using bulk, solution or emulsion techniques. In any case, the styrenic block copolymer contains ethylenic unsaturation at a minimum, and generally, will be recovered as a solid such as a crumb, a powder, a pellet, or the like.

In general, when solution anionic techniques are used, conjugated diolefin polymers and copolymers of conjugated diolefins and alkenyl aromatic hydrocarbons are prepared by contacting the monomer or monomers to be polymerized simultaneously or sequentially with an organoalkali metal compound in a suitable solvent at a temperature in the range of from 150° C. to 300° C., preferably at a temperature in the range of from 0° C. to 100° C. Particularly effective anionic polymerization initiators are organolithium compounds having the general formula: $RLi_n$ wherein R is an aliphatic, cycloaliphatic, aromatic, or alkyl-substituted aromatic hydrocarbon radical having from 1 to 20 carbon atoms; and n is an integer of 1 to 4.

In addition to sequential techniques to obtain triblocks, tetrablocks, and higher orders of repeating structures, anionic initiators, at a minimum, can be used to prepare diblocks of styrene-polydiene having a reactive ("live") chain end on the diene block which can be reacted through a coupling agent to create, for example, $(S-I)_xY$ or $(S-B)_xY$ structures wherein x is an integer from 2 to 30, Y is a coupling agent, I is isoprene, B is butadiene and greater than 65 percent of S-I or S-B diblocks are chemically attached to the coupling agent. Y usually has a molecular weight which is low compared to the polymers being prepared and can be any of a number of materials known in the art, including halogenated organic compounds; halogenated alkyl silanes; alkoxy silanes; various esters such as alkyl and aryl benzoates, difunctional aliphatic esters such as dialkyl adipates and the like; polyfunctional agents such as divinyl benzene (DVB) and low molecular weight polymers of DVB. Depending on the selected coupling agent, the final polymer can be a fully or partially coupled linear triblock polymer (x=2), i.e., SIYIS; or in a branched, radial or star configuration. The coupling agent, being of low molecular weight, does not materially affect the properties of the final polymer. DVB oligomer is commonly used to create star polymers, wherein the number of diene arms can be 7 to 20 or even higher.

It is not required in coupled polymers that the diblock units all be identical. In fact, diverse "living" diblock units can be brought together during the coupling reaction giving a variety of unsymmetrical structures, i.e., the total diblock chain lengths can be different, as well as the sequential block lengths of styrene and diene.

Preferably, the styrenic block copolymers are hydrogenated to improve weatherability and oxidation stability. In general, the hydrogenation or selective hydrogenation of the polymer may be accomplished using any of the several hydrogenation processes known in the prior art. For example, the hydrogenation may be accomplished using methods such as those taught, in U.S. Pat. Nos. 3,494,942; 3,634,594; 3,670, 054; 3,700,633; and Re. 27,145, which are incorporated by reference for their teaching regarding hydrogenation of styrenic block copolymers and the polymers that result therefrom. The methods known in the prior art for hydrogenating polymers containing ethylenic unsaturation and for hydrogenating or selectively hydrogenating polymers containing aromatic and ethylenic unsaturation, involve the use of a suitable catalyst, particularly a catalyst or catalyst precursor comprising an iron group metal atom, particularly nickel or cobalt, and a suitable reducing agent such as an aluminum alkyl.

In general, the hydrogenation will be accomplished in a suitable solvent at a temperature in the range of from 20° C. to 100° C. and at a hydrogen partial pressure in the range of from 7 atm ($10^5$ Pa) to 340 atm ($10^5$ Pa), preferably 7 atm ($10^5$ Pa) to 70 atm ($10^5$ Pa). Catalyst concentrations are generally in the range of from 10 ppm (wt) to 500 ppm (wt) of iron group metal based on total solution. Contacting at hydrogenation conditions is generally continued for a period of time in the range of from 60 to 240 minutes. After the hydrogenation is completed, the hydrogenation catalyst and catalyst residue will, generally, be separated from the polymer.

Not wishing to be limited by theory, it is thought that the compatibility of the saturated conjugated diene with the interpolymer contributes to the ability of the composition of the present invention to exhibit the novel properties present. This is consistent with other embodiments of the present invention. For example, in a particular embodiment of the present invention, a composition comprises an interpolymer, SIS, and a minor amount of SEBS which is thought to compatibilize the interpolymer and SIS. In another embodiment of the present invention, a composition comprises an interpolymer, SBS, and a minor amount of SEBS which is thought to compatibilize the interpolymer and SBS.

The Melt Indices of the Present Invention

The preferred melt index ($I_2$) of the interpolymer is generally at least about 0.5, preferably at least about 0.75 g/10 min. Correspondingly, the preferred melt index ($I_2$) of the interpolymer is generally less than about 30 g/10 min., sometimes preferably less than about 24 g/10 min. However, the preferred melt index may often depend upon the desired conversion process, e.g. blown film, cast film and extrusion lamination, etc.

Blown Film

For blown film processes, the melt index ($I_2$) of the interpolymer is generally at least about 0.5, preferably at least about 0.75 g/10 min. The melt index ($I_2$) of the interpolymer is generally at most about 5, preferably at most about 3 g/10 min. In addition, it is often preferable that the ethylene/α-olefin interpolymer be made with a diethyl zinc chain shuttling agent wherein the mole ratio of zinc to ethylene is from about $0.03 \times 10^{-3}$ to about $1.5 \times 10^{-3}$.

Cast Film and Extrusion Lamination

For cast film and extrusion laminate processes, the melt index ($I_2$) of the interpolymer is generally at least about 0.5, preferably at least about 0.75, more preferably at least about 3, even more preferably at least about 4 g/10 min. The melt index ($I_2$) of the interpolymer is generally at most about 20, preferably at most about 17, more preferably at most about 12, even more preferably at most about 5 g/10 min.

In addition, it is often preferable that the ethylene/α-olefin interpolymer be made with a diethyl zinc chain shuttling agent wherein the ratio of zinc to ethylene is from about $0.03 \times 10^{-3}$ to about $1.5 \times 10^{-3}$.

The composition may contain additional components such as other polyolefin based plastomers and/or elastomers. Polyolefin based elastomers and plastomers/polymers include copolymers of ethylene with at least one other alpha olefin ($C_3$-$C_{22}$), as well as copolymers of propylene with at least one other alpha olefin ($C_2$, $C_4$-$C_{22}$). In a particularly preferred embodiment, a second component comprising high pressure low density type resin is employed. Possible materials for use as an additional component include LDPE (homopolymer); ethylene copolymerized with one or more α-olefin e.g. propylene or butene; and ethylene copolymerized with at least one α,β-ethylenically unsaturated comonomer, e.g., acrylic acid, methacrylic acid, methyl acrylate and vinyl acetate; branched polypropylene and blends thereof. A suitable technique for preparing useful high pressure ethylene copolymer compositions is described in U.S. Pat. No. 4,599,392, the disclosure of which is incorporated herein by reference.

In yet another embodiment of this invention, a third polymer component may be used to improve compatibility, miscibility, dispersion, or other characteristics among the polymer components as is generally known in the art.

For additional attributes, any of the polymer components may be functionalized or modified at any stage. Examples include but are not limited to grafting, crosslinking, or other methods of functionalization.

Film layers comprising the composition of the present invention are often capable of stress relaxation of at most about 60, preferably at most about 40, more preferably at most about 28% at 75% strain at 100° F. for at least 10 hours.

Meltblown Fiber

Meltblown fibers are fibers formed by extruding a molten thermoplastic material through a plurality of fine, usually circular, capillaries of a meltblowing die as molten threads or filaments into converging high-velocity, usually hot, gas (e.g., air) streams which are flowing in the same direction as the extruded filaments or threads of the molten thermoplastic material so that the extruded filaments or threads are attenuated, i.e., drawn or extended, to reduce their diameter.

The threads or filaments may be attenuated to microfiber diameter which means the threads or filaments have an average diameter not greater than about 75 microns, generally from about 0.5 microns to about 50 microns, and more particularly from about 2 microns to about 40 microns. Thereafter, the meltblown fibers are carried by the high-velocity gas stream and are deposited on a collecting surface to form a web of randomly disbursed meltblown fibers. The meltblown process is well-known and is described in various patents and publications, including NRL Report 4364, "Manufacture of super-Fine Organic Fibers" by B. A. Wendt, E. L. Boone and D. D Fluharty; NRL Report: 5265, "An Improved Device for the Formation of Super-Fine Thermoplastic Fibers" by K. D Lawrence, R. T. Lukas and J. A. Young; U.S. Pat. No. 3,676, 242 to Prentice; and U.S. Pat. No. 3,849,241 to Buntin et al. The foregoing references are incorporated herein in by reference in their entirety. Meltblown fibers are microfibers which may be continuous or discontinuous, are generally smaller than 10 microns in average diameter and are generally tacky when deposited onto a collecting surface.

Preparation of Blends

Blends can be prepared by any suitable means known in the art including tumble dry-blending, weigh feeding, solvent blending, melt blending via compound or side-arm extrusion, or the like as well as combinations thereof.

The components of the blends of the current invention can be used in a chemically and/or physically modified form to prepare the inventive composition. Such modifications can be accomplished by any known technique such as, for example, by ionomerization and extrusion grafting.

Additives such as antioxidants (e.g., hindered phenolics such as Irganox® 1010 or Irganox® 1076 supplied by Ciba Geigy), phosphites (e.g., Irgafos® 168 also supplied by Ciba Geigy), cling additives (e.g., PIB), Standostab PEPQ™ (supplied by Sandoz), pigments, colorants, fillers, and the like can also be included in the ethylene polymer extrusion composition of the present invention. The article made from or using the inventive composition may also contain additives to enhance antiblocking and coefficient of friction characteristics including, but not limited to, untreated and treated silicon dioxide, talc, calcium carbonate, and clay, as well as primary, secondary and substituted fatty acid amides, chill roll release agents, silicone coatings, etc. Other additives may also be added to enhance the anti-fogging characteristics of, for example, transparent cast films, as described, for example, in U.S. Pat. No. 4,486,552, the disclosure of which is incorporated herein by reference. Still other additives, such as quaternary ammonium compounds alone or in combination with ethylene-acrylic acid (EAA) copolymers or other functional polymers, may also be added to enhance the antistatic characteristics of coatings, profiles and films of this invention and allow, for example, the packaging or making of electronically sensitive goods. Other functional polymers such as maleic anhydride grafted polyethylene may also be added to enhance adhesion, especially to polar substrates.

Alternatively, the polymeric and non-polymeric components may be combined with steps that include solution blending (also known as solvent blending) or a combination of melt and solution methods. Solution blending methods include but are not limited to multiple reactors in series, parallel, or combinations thereof. As solution methods can sometimes result in better dispersion of the components, greater efficacy of the second component is anticipated. Benefits may include using less second component with maintenance of greater elastic properties such as reduced set strain and less hysteresis.

Monolayer or multilayer elastic films and laminates comprising the inventive composition can be prepared by any means including blown film techniques, coextrusion, laminations and the like and combinations thereof, including those techniques described below. When the inventive composition is used in multilayered constructions, substrates or adjacent material layers can be polar or nonpolar including for example, but not limited to, paper products, metals, ceramics, glass and various polymers, particularly other polyolefins, and combinations thereof. If a polymer substrate is used, it may take a variety of forms including but not limited to webs, foams, fabrics, nonwovens, films etc. Particularly preferred laminates often comprise a nonwoven fabric selected from the group consisting of melt blown, spunbond, carded staple fibers, spunlaced staple fibers, and air laid staple fibers. The fabric may comprise two or more compositionally different fibers. For example, the fabric may comprise a multi-component polymeric fiber, wherein at least one of the polymeric components comprises at least a portion of the fiber's surface. These nonwovens and the fibers that comprise them can be bonded in a variety of methods known to those of ordinary skill in the art. These methods include but are not limited to calendaring, thermal point bonding, ultrasonic welding, chemical binders, adhesives, high energy electron beams, and/or lasers etc.

Fabricated articles comprising the inventive compositions may be selected from the group consisting of adult incontinence articles, feminine hygiene articles, infant care articles, surgical gowns, medical drapes, household cleaning articles, expandable food covers, and personal care articles.

Examples of processes, manufacture, and articles that may benefit from employing the inventive composition and may be suitable for use with the current inventions include, but are not limited to, EP0575509B1, EP0575509B1, EP0707106B1, EP0707106B1, EP1637320, EP472942B1, EP472942B1, U.S. Pat. No. 3,833,973, U.S. Pat. No. 3,855,046, U.S. Pat. No. 3,860,003, U.S. Pat. No. 4,100,324, U.S. Pat. No. 4,116,892, U.S. Pat. No. 4,422,892, U.S. Pat. No. 4,443,513, U.S. Pat. No. 4,525,407, U.S. Pat. No. 4,573,986, U.S. Pat. No. 4,636,207, U.S. Pat. No. 4,662,875, U.S. Pat. No. 4,695,278, U.S. Pat. No. 4,704,116, U.S. Pat. No. 4,713,069, U.S. Pat. No. 4,720,415, U.S. Pat. No. 4,795,454, U.S. Pat. No. 4,798,603, U.S. Pat. No. 4,808,178, U.S. Pat. No. 4,818,464, U.S. Pat. No. 4,846,815, U.S. Pat. No. 4,888,231, U.S. Pat. No. 4,900,317, U.S. Pat. No. 4,909,803, U.S. Pat. No. 4,938,753, U.S. Pat. No. 4,938,757, U.S. Pat. No. 4,940,464, U.S. Pat. No. 4,963,140, U.S. Pat. No. 4,965,122, U.S. Pat. No. 4,981,747, U.S. Pat. No. 5,019,065, U.S. Pat. No. 5,032,122, U.S. Pat. No. 5,061,259, U.S. Pat. No. 5,085,654, U.S. Pat. No. 5,114,781, U.S. Pat. No. 5,116,662, U.S. Pat. No. 5,137,537, U.S. Pat. No. 5,147,343, U.S. Pat. No. 5,149,335, U.S. Pat. No. 5,151,092, U.S. Pat. No. 5,156,793, U.S. Pat. No. 5,167,897, U.S. Pat. No. 5,169,706, U.S. Pat. No. 5,226,992, U.S. Pat. No. 5,246,433, U.S. Pat. No. 5,286,543, U.S. Pat. No. 5,318,555, U.S. Pat. No. 5,336,545, U.S. Pat. No. 5,336,554, U.S. Pat. No. 5,360,420, U.S. Pat. No. 5,364,382, U.S. Pat. No. 5,415,644, U.S. Pat. No. 5,429,629, U.S. Pat. No. 5,490,846, U.S. Pat. No. 5,492,751, U.S. Pat. No. 5,496,298, U.S. Pat. No. 5,509,915, U.S. Pat. No. 5,514,470, U.S. Pat. No. 5,518,801, U.S. Pat. No. 5,522,810, U.S. Pat. No. 5,562,646, U.S. Pat. No. 5,562,650, U.S. Pat. No. 5,569,234, U.S. Pat. No. 5,591,155, U.S. Pat. No. 5,599,338, U.S. Pat. No. 5,601,542, U.S. Pat. No. 5,635,275, U.S. Pat. No. 5,635,276, U.S. Pat. No. 5,643,588, U.S. Pat. No. 5,650,214, U.S. Pat. No. 5,674,216, U.S. Pat. No. 5,685,874, U.S. Pat. No. 5,691,035, U.S. Pat. No. 5,698,054, U.S. Pat. No. 5,733,628, U.S. Pat. No. 5,772,825, U.S. Pat. No. 5,779,831, U.S. Pat. No. 5,783,014, U.S. Pat. No. 5,836,932, U.S. Pat. No. 5,837,352, U.S. Pat. No. 5,843,056, U.S. Pat. No. 5,843,057, U.S. Pat. No. 5,858,515, U.S. Pat. No. 5,879,341, U.S. Pat. No. 5,882,769, U.S. Pat. No. 5,891,544, U.S. Pat. No. 5,916,663, U.S. Pat. No. 5,931,827, U.S. Pat. No. 5,968,025, U.S. Pat. No. 5,993,433, U.S. Pat. No. 6,015,764, U.S. Pat. No. 6,027,483, U.S. Pat. No. 6,075,179, U.S. Pat. No. 6,107,537, U.S. Pat. No. 6,118,041, U.S. Pat. No. 6,153,209, U.S. Pat. No. 6,255,236, U.S. Pat. No. 6,297,424, U.S. Pat. No. 6,303,208, U.S. Pat. No. 6,307,119, U.S. Pat. No. 6,318,555, U.S. Pat. No. 6,428,526, U.S. Pat. No. 6,491,165, U.S. Pat. No. 6,605,172, U.S. Pat. No. 6,627,786, U.S. Pat. No. 6,635,797, U.S. Pat. No. 6,642,427, U.S. Pat. No. 6,645,190, U.S. Pat. No. 6,689,932, U.S. Pat. No. 6,763,944, U.S. Pat. No. 6,808,789, U.S. Pat. No. 6,849,067, U.S. Pat. No. 6,894,319, US2003/0022582, US2005/0003152, US2005/0043460, US2005/0158513, WO9003258A1, WO9003464A2, WO9815399, WO9829479, WO0521262, and WO05023544.

The composition of the present invention may be used in a method of producing a composite elastic material comprising at least one gatherable web bonded to at least one elastic web, such as disclosed in U.S. Pat. No. 4,720,415, which is herein incorporated by reference in its entirety. Such method comprises (a) tensioning an elastic web (which may comprise a fibrous web such as a nonwoven web of elastomeric fibers, e.g., meltblown elastomeric fibers) to elongate it; (b) bonding the elongated elastic web to at least one gatherable web under conditions which soften at least portions of the elastic web to form a bonded composite web; and (c) relaxing the composite web immediately after the bonding step whereby the gatherable web is gathered to form the composite elastic material. The composition of the present invention may be an elastic web or a gatherable web. Other aspects of the method provide for maintaining the fibrous elastic web in a stretched condition during bonding, at an elongation of at least about 25 percent, preferably about 25 percent to over 500 percent, for example, about 25 percent to 550 percent elongation during the bonding.

The method may also include bonding the elongated elastic web to the gatherable web by overlaying the elastic and gatherable webs and applying heat and pressure to the overlaid webs, for example, by heating bonding sites on the elastic web to a temperature of from at least about 65° C. to about 120° C., preferably from at least about 70° C. to about 90° C.

In accordance with the present invention there is also provided an elastic composite material comprising an elastic web bonded to at least one gatherable web which is extensible and contractible with the elastic web upon stretching and relaxing of the composite material, the elastic composite material being made by a method as described above, wherein the elastic composite material comprises the composition of the present invention.

In accordance with another aspect of the present invention, the elastic web is bonded to the gatherable web at a plurality of spaced-apart locations in a repeating pattern and the gatherable web is gathered between the bonded locations.

Other aspects of the invention provide that the elastic web may comprise a nonwoven web of elastomeric fibers, preferably elastomeric microfibers, such as, for example, an elastomeric nonwoven web of meltblown elastomeric fibers or an elastomeric film.

Other aspects of the invention include one or more of the following in any combination: the elastic web, e.g., a fibrous elastic web, is bonded to the gatherable web at a plurality of spaced-apart locations in a repeating pattern and the gatherable web is gathered between the bonded locations; the elastic web preferably has a low basis weight of from about 5 to about 300, preferably from about 5 to about 200, grams per square meter ($gm/m^2$), for example, from about 5 to about 100 grams per square meter, although its basis weight can be much higher; and, the gatherable web is a nonwoven, non-elastic material, preferably one composed of fibers formed from materials selected from the group including polyester fibers, e.g., poly(ethylene terephthalate) fibers, polyolefin fibers, polyamide fibers, e.g., nylon fibers, cellulosic fibers, e.g., cotton fibers, and mixtures thereof. A particular aspect of the present invention is to use elastic and/or lower modulus nonwovens including those comprising propylene copolymers such as those described in U.S. Pat. No. 7,101,623 B2, U.S. Pat. No. 7,101,622 B2, and WO2000070134. Such fibers can comprise copolymers of propylene and ethylene. Suitable resins for fabricating such fibers including but are not limited to VERSIFY™ (available from The Dow Chemical Company) and VISTAMAXX™ (available from ExxonMobil Corporation). In another aspect of the present invention, the polyolefin fibers comprise olefin block copolymers such as those generally described in the present application as well as in WO2005/090427 and US 2006-0199930 A1. Not wishing to be bound by theory, it is thought that a nonwoven comprising lower modulus and/or extensible and/or elastic fibers can enable greater compliance and elasticity to the overall structure. In situations where greater elasticity is not required, this is further thought to enable opportunities for decreased elastomeric film usage which can result in a lighter and more flexible overall structure. In another embodiment, the structure comprises a nonwoven which comprises a mixture of any combination two or more fiber types from the possible group of conventional, lower modulus, extensible, and elastic fibers. Alternatively, the gatherable web may be any suitable woven fabric. The fibers of any of the above embodiments may be made in a number of forms known to those of ordinary skill in the art. These forms include but are not limited to monofilament, bicomponent, multicomponent, side-by-side, coaxial, islands-in-the-sea etc.

The compositions of the present invention may also be used in a method of producing a composite elastic necked-bonded material including one or more layers of necked material joined to one or more layers of elastic sheet, as disclosed in U.S. Pat. Nos. 5,226,992 and 5,336,545, which are herein incorporated by reference in their entirety. The method comprises applying a tensioning force to at least one neckable material to neck the material; and joining the tensioned, necked material to at least one elastic sheet at least at two locations. The composition of the present invention may be used in a neckable material, an elastic sheet or both. The necked bonded material may comprise a laminate comprising the composition of the present invention. The necked bonded material may also be apertured.

The necked material used as a component of the composite elastic necked-bonded material is formed from a neckable material. If the material is stretchable, it may be necked by stretching in a direction generally perpendicular to the desired direction of neck-down. The neckable material may be any material that can be necked and joined to an elastic sheet. Such neckable materials include knitted and loosely woven fabrics, bonded carded webs, spunbonded webs or meltblown webs. The meltblown web may include meltblown microfibers. The neckable material may also have multiple layers such as, for example, multiple spunbonded layers and/or multiple meltblown layers. The neckable material may be made of polymers such as, for example, polyolefins. Exemplary polyolefins include polypropylene, polyethylene, ethylene copolymers and propylene copolymers. In particular, the polyolefin may comprise olefin block copolymers such as those generally described in the present application as well as in WO2005/090427 and US 2006-0199930 A1.

The composition of the present invention may also be used in a laminate in a stretched bonded material, a machine direction activated material, a cross direction activated material and a machine and cross direction activated material.

The elastic sheet may be a pressure sensitive elastomer adhesive sheet. If the elastic sheet is a nonwoven web of elastic fibers or pressure sensitive elastomer adhesive fibers, the fibers may be meltblown fibers. More particularly, the meltblown fibers may be meltblown microfibers.

The elastic sheet and the reversibly necked material may be joined by overlaying the materials and applying heat and/or pressure to the overlaid materials. Alternatively, the layers may be joined by using other bonding methods and materials such as, for example, adhesives, pressure sensitive adhesives, ultrasonic welding, high energy electron beams, and/or lasers. In one aspect, the elastic sheet may be formed directly on the necked material utilizing processes, such as, for example, meltblowing processes and film extrusion processes.

Other aspects of this invention provide that the pressure sensitive elastomer adhesive sheet and necked material may be joined without the application of heat such as, for example, by a pressure bonder arrangement or by tensioned wind-up techniques.

When an elastic sheet is formed directly on the necked material utilizing film extrusion processes, the method of the present invention may include the following steps: 1) providing a continuously advancing tensioned, necked material; 2) extruding a film of substantially molten elastomer through a die tip; 3) depositing the extruded elastomeric film onto the tensioned, necked material within from about 0.1 to about 1 second of exiting the die tip to form a multilayer material; and 4) immediately applying pressure to the multilayer material to bond the tensioned, necked material to the elastomeric film, as is disclosed in U.S. Pat. No. 5,514,470, which is herein incorporated by reference in its entirety.

Generally speaking, the tensioned, necked material may be material that was pre-necked and treated to remain in its necked condition (e.g., a reversibly necked material) or may be provided by applying a tensioning force to at least one neckable material to neck the material.

According to the invention, the film of elastomer may be deposited onto the tensioned, necked material within from about 0.25 seconds to about 0.5 seconds of exiting the die tip. For example, the film of elastomer is deposited onto the tensioned, necked material within from about 0.3 seconds to about 0.45 seconds of exiting the die tip.

According to one aspect of the invention, the film of elastomer may be extruded at a temperature of from about 180° C. to about 285° C. For example, a film of elastomer may be extruded at a temperature of from about 195° C. to about 250° C. Desirably, the film of elastomer may be extruded at a temperature from about 200° C. to about 220° C.

Pressure is applied to bond the necked material to the elastomeric film. This pressure may be applied utilizing, for example, a pressure roll arrangement. The pressure roll arrangement may include at least a first roll and a second roll configured to provide a gap between the rolls. Generally speaking, the gap setting between the first and second rolls of the pressure roll arrangement is large enough so that the force required to extend the resulting composite elastic material on the first pull is at least about 25 percent less than the force required to extend an identical composite elastic material prepared in an identical pressure roll arrangement with the pressure rolls in substantial bonding contact. For example, the method of the present invention may be practiced with the gap setting between the pressure rollers at about 15 mils (about 0.381 mm) to about 125 mils (about 3.175 mm). As a further example, the method of the present invention may be practiced with the gap setting between the pressure rollers at about 30 mils to about 100 mils. Desirably, the method of the present invention is be practiced with the gap setting between the pressure rollers at about 40 mils to about 65 mils.

Alternatively, and/or additionally, pressure applied to bond the necked material to the extruded elastomeric film may be generated by the tensioning force on the tensioned, necked material as the elastomeric film is temporarily configured between a layer of tensioned, necked material and a roller or surface (e.g., a protruding roller or protruding surface).

The elastomeric film may be a film of elastomeric pressure sensitive elastomer adhesive. The elastomeric pressure sensitive elastomer adhesive may be formed from a blend including an elastomeric polymer of the present invention and a tackifying resin.

The present invention also encompasses a composite elastic material produced by the method described above.

According to one aspect of the present invention, the method of producing a composite elastic necked-bonded material including one or more layers of necked material joined to one or more layers of elastic sheet includes the following steps: 1) providing a first and second continuously advancing sheet, each sheet being composed of at least one tensioned, necked material and each sheet advancing in intersecting relationship to form a contact zone; 2) extruding a film of substantially molten elastomer through a die tip between the first and second continuously advancing sheet of tensioned, necked material so that the extruded elastomeric film is deposited into the contact zone within from about 0.1 to about 1 second of exiting the die tip to form a multilayer material; and 3) immediately applying pressure to the multilayer material to bond each tensioned, necked material to the elastomeric film.

Generally speaking, the first and second continuously advancing sheets of tensioned, necked material may be material that was pre-necked and treated to remain in its necked condition (e.g., a reversibly necked material) or may be provided by applying a tensioning force to at least one neckable material to neck the material.

According to the invention, the film of elastomer may be deposited onto the tensioned, necked material within from about 0.25 seconds to about 1 second of exiting the die tip. For example, the film of elastomer may be deposited onto the tensioned, necked material within from about 0.3 seconds to about 0.45 seconds of exiting the die tip.

In an aspect of the invention, the film of elastomer may be extruded at a temperature of from about 180° C. to about 285° C. For example, a film of elastomer may be extruded at a temperature of from about 195° C. to about 250° C. Desirably, the film of elastomer may be extruded at a temperature from about 200° C. to about 220° C.

Other aspects of this invention provide that the pressure sensitive elastomer adhesive sheet and necked material may be joined without the application of heat such as, for example, by a pressure bonder arrangement or by tensioned wind-up techniques.

The present invention also comprises a continuous feed spun bonded laminate comprising the composition of the present invention having improved elastic properties at body temperature such as those disclosed in WO1999/017926 and U.S. Pat. No. 6,323,389, which is herein incorporated by reference in its entirety. In a preferred embodiment, the laminate comprises a layer of filaments formed by a continuous filament process, to which is bonded a layer of meltblown fibers. This composite material is then sandwiched between two layers of spunbond fibers after being stretched. The resulting layers are then passed between a pair of niprolls and the resulting laminate is then relaxed prior to winding on a 4:1 takeup roll.

The composition of the present invention is preferably used in the filament layer. The styrenic block copolymer is preferably a triblock polystyrene-poly(ethylene/propylene)-polystyrene ("SEPS") copolymer or a polystyrenepoly(ethylene/butylene)-polystyrene ("SEBS") copolymer, each having a number average molecular weight of about 81,000 g/mol. The weight percent of styrene is approximately 18% and the weight percent of ethylene/propylene is approximately 82%. Conventional triblock polymer is typically in the 61,000 g/mol range. The molecular weight increase in the polymer midblock, while holding the molecular weight of the styrene block constant, increases the entanglement density, polymer chain persistence length and the relaxation time. The laminate is particularly useful as side panel material in training pants because of the resistance to sagging at body temperature.

In addition, the present invention relates to non-tacky, microtextured, multi-layer elastomeric laminates such as described in EP500590 B 1, and U.S. Pat. Nos. 5,501,679 and 5,691,034, which are herein incorporated by reference in their entirety. The laminates of the present invention are comprised both of an elastomeric polymeric core layer(s), which provides elastomeric properties to the laminate and one or more polymeric skin layers which are capable of becoming microtextured. This microtexturing increases the comfort level of the elastomeric material which is complemented by a significant lowering of the laminate's coefficient of friction and modulus. In preferred embodiments of the present invention the skin layer further can function to permit controlled release or recovery of the stretched elastomer, modify the modulus of elasticity of the elastomeric laminate and/or stabilize the shape of the elastomeric laminate (i.e., by controlling further necking). The laminates can be prepared by coextrusion of the selected polymers or by application of one or more elastomer layers onto one or more already formed skin layer(s). Coextrusion is preferred. The novel non-tacky microtextured laminate is obtained by stretching the laminate past the elastic limit of the outer skin layers. The laminate then recovers, which can be instantaneous, over an extended time period, which is skin layer controllable, or by the application of heat, which is also skin layer controllable.

Stretching of the laminate can be uniaxial, sequentially biaxial, or simultaneously biaxial. The method and degree of stretch allow significant control over the resulting microtextured surface.

The elastomer comprises compositions of the present invention. Further, preferably, the elastomer of the invention will sustain only small permanent set following deformation and relaxation which set is preferably 20 to 200 percent and more preferably 20 to 100 percent of the original length at 500%. The elastomer of the present invention should be stretched to a degree that causes relatively consistent permanent deformation in a relatively inelastic skin layer. This can be as low as 50% elongation. Preferably, the elastomer is capable of undergoing up to 300 to 1200% elongation at room temperature, and most preferably up to 600 to 800% elongation at room temperature.

In a particular aspect, the composition of the present invention comprises a layer in a multilayer structure in which at least one skin layer is used. In a particular aspect, the skin layer can be formed of any higher crystalline, semicrystalline or amorphous polymer that is less elastic (e.g. higher permanent set) than the core layer(s) and will undergo permanent deformation at the stretch percentage that the elastomeric laminate will undergo. Therefore, slightly elastic compounds, such as some olefinic elastomers, e.g. ethylene-propylene elastomers, other olefin block copolymers, or ethylene-propylene-diene terpolymer elastomers or ethylenic copolymers, e.g., ethylene vinyl acetate, can be used as skin layers, either alone or in blends. However, the skin layer is generally a polyolefin such as polyethylene, polypropylene, polybutylene or a polyethylene-polypropylene copolymer, but may also be wholly or partly polyamide such as nylon, polyester such as polyethylene terephthalate, polyvinylidene fluoride, polyacrylate such as poly(methyl methacrylate)(only in blends) and the like, and blends thereof. In one particular aspect, the skin layer comprises α-olefins. In another aspect, the skin layer comprises olefin block copolymers such as those generally described in the present application as well as in WO2005/090427 and US 2006-0199930 A1. The skin layer material can be influenced by the type of elastomer selected. If the elastomeric layer is in direct contact with the skin layer the skin layer should have sufficient adhesion to the elastomeric core layer such that it will not readily delaminate. Skin-to-core contact has been found to follow three modes: first, full contact between the core and microtextured skin; second, cohesive failure of the core under the microtexture folds; and third, adhesive failure of the skin to the core under the microtexture folds with intermittent skin/core contact at the fold valleys. However, where a high modulus elastomeric layer is used with a softer polymer skin layer attachment may be acceptable yet a microtextured surface may not form.

The skin layer is used in conjunction with an elastomeric layer and can either be an outer layer or an inner layer (e.g., sandwiched between two elastomeric layers). Used as either an outer or inner layer the skin layer will modify the elastic properties of the elastomeric laminate.

Additives useful in the skin layer include, but are not limited to, mineral oil extenders, antistatic agents, pigments, dyes, antiblocking agents, provided in amounts less than about 15%, starch and metal salts for degradability and stabilizers such as those described for the elastomeric core layer.

Other layers may be added between the core layer and the outer layers, such as tie layers to improve the bonding of the layers. Tie layers can be formed of, or compounded with, typical compounds for this use including ethylene copolymers, propylene copolymers, propylene-ethylene copolymers, olefin block copolymers, maleic anhydride modified elastomers, ethyl vinyl acetates and olefins, polyacrylic imides, butyl acrylates, peroxides such as peroxypolymers, e.g., peroxyolefins, silanes, e.g., epoxysilanes, reactive polystyrenes, chlorinated polyethylene, acrylic acid modified polyolefins and ethyl vinyl acetates with acetate and anhydride functional groups and the like, which can also be used in blends or as compatiblizers in one or more of the skin or core layers. Tie layers are particularly useful when the bonding force between the skin and core is low. This is often the case with polyethylene skin as its low surface tension resists adhesion. However, any added layers must not significantly affect the microstructuring of the skin layers.

In particular, the tie layer may comprise olefin block copolymers such as those generally described in the present application as well as in WO2005/090427 and US 2006-0199930 A1.

One unique feature of this aspect of the invention is the ability to control the shrink recovery mechanism of the laminate depending on the conditions of film formation, the nature of the elastomeric layer, the nature of the skin layer, the manner in which the laminate film is stretched and the relative thicknesses of the elastomeric and skin layer(s). By controlling these variables, the laminate film can be designed to instantaneously recover, recover over time or recover upon heat activation.

The present invention is also directed to laminates such as those described above wherein the one or more polymeric skin layers are capable of becoming microtextured at specified areas along the laminate length, as described in U.S. Pat. No. 5,344,691, which is herein incorporated by reference. The microtextured areas will correspond to sections of the laminate that have been activated from an inelastic to an elastomeric form. In preferred embodiments of the present invention, the skin layer can further function to permit controlled recovery of the stretched elastomer, modify the modulus behavior of the elastomeric laminate and/or stabilize the shape of the elastomeric laminate (e.g., by controlling necking). The novel, non-tacky microtextured laminate is obtained by stretching the laminate past the elastic limit of predetermined regions of the skin layers. This is termed selective or preferential activation. The laminate then recovers in these predetermined regions, which can be instantaneous, over an extended time period, which is skin layer controllable, or by the application of heat, which is also skin layer controllable.

This selective or preferential activation is produced by controlling the relative elastic modulus values of selected cross-sectional areas of the laminate to be less than modulus values of adjacent cross-sectional areas. The areas controlled to have reduced modulus will preferentially yield when subjected to stress. This will result in either preferential elastization of specified zones or fully elasticized laminates with higher strain regions, depending on the location of the areas of low modulus and the manner of stretch. Alternatively, the laminate could be treated to enhance or concentrate stress in selected regions. This will yield essentially the same results as providing low modulus regions. By either construction, the laminate can activate in selected regions at lower stretch ratios than would normally be required to activate the entire laminate.

The modulus can be controlled by providing one or more layers of the laminate with relatively low and high modulus areas. This can be accomplished by selectively altering the physical or chemical characteristics of regions of one or more layers or by providing a layer(s) with regions of diverse chemical composition. Regionally enhanced stress can be induced by physical or chemical treatment of a layer(s) such as by ablation, scoring, corona treatment or the like.

Viscosity reducing polymers and plasticizers can also be blended with the elastomers such as low molecular weight polyethylene and polypropylene polymers and copolymers, or tackifying resins such as Wingtack™, aliphatic hydrocarbon tackifiers available from Goodyear Chemical Company. Tackifiers can also be used to increase the adhesiveness of an elastomeric layer to a skin layer. Examples of tackifiers include aliphatic or aromatic hydrocarbon liquid tackifiers, polyterpene resin tackifiers, and hydrogenated tackifying resins. Aliphatic hydrocarbon resins are preferred.

Additives such as dyes, pigments, antioxidants, antistatic agents, bonding aids, antiblocking agents, slip agents, heat stabilizers, photostabilizers, foaming agents, glass bubbles, starch and metal salts for degradability or microfibers can also be used in the elastomeric core layer(s). Suitable antistatic aids include ethoxylated amines or quaternary amines such as those described, for example, in U.S. Pat. No. 4,386,125, which also describes suitable antiblocking agents, slip agents and lubricants. Softening agents, tackifiers or lubricants are described, for example, in U.S. Pat. No. 4,813,947 and include coumarone-indene resins, terpene resins, hydrocarbon resins and the like. These agents can also function as viscosity reducing aids. Conventional heat stabilizers include organic phosphates, trihydroxy butyrophenone or zinc salts of alkyl dithiocarbonate. Suitable antioxidants include hindered phenolic compounds and amines possibly with thiodipropionic acid or aromatic phosphates or tertiary butyl cresol. See also U.S. Pat. No. 4,476,180 for suitable additives and percentages.

The composition of the present invention may also be used in non-tacky, microtextured, multi-layer elastomeric laminated tape backings and the tapes made therefrom, such as those described in U.S. Pat. No. 5,354,597, which is herein incorporated by reference in its entirety. The laminate tape backings of the present invention are comprised both of an elastomeric polymeric core layer(s), which provides elastomeric properties to the laminate and one or more polymeric skin layers which are capable of becoming microtextured. This microtexturing gives the tape natural low adhesion backsize properties, increases ink receptivity, acts as an adhesive primer, and lowers the laminate coefficient of friction and modulus. In preferred embodiments of the present invention the skin layer further can function to permit controlled release or recovery of the stretched elastomer, modify the modulus of elasticity of the elastomeric tape and/or stabilize the shape of the elastomeric tape. The laminate tape backings may be prepared by coextrusion of the selected polymers or by application of one or more elastomer layers onto one or more already formed skin layer(s) or vice versa. Coextrusion is preferred. Pressure-sensitive adhesive (hereinafter adhesive) may be applied by any conventional mechanism including coextrusion. The novel microtextured laminate tape and/or tape backing is obtained by stretching the laminate past the elastic limit of the skin layers. The laminate then recovers, which can be instantaneous, over an extended time period, which is skin layer controllable, or by the application of heat, which is also skin layer controllable. Stretching of the laminate tape or backing can be uniaxial, sequentially biaxial, or simultaneously biaxial.

A laminate capable of instantaneous shrink is one in which the stretched elastomeric laminate will recover more than 15% in 1 sec. A laminate capable of time shrink is one where the 15% recovery point takes place more than 1 sec., preferably more than 5 sec., most preferably more than 20 sec. after stretch, and a laminate capable of heat shrink is where less than 15% shrink recovery occurs to the laminate in the first 20 seconds after stretch. Percent recovery is the percent that the amount of shrinkage is of the stretched length minus the original length. For heat shrink, there will be an activation temperature which will initiate significant heat activated recovery. The activation temperature used for heat shrink will generally be the temperature that will yield 50% of the total possible recovery ($T_{a-50}$) and preferably this temperature is defined as the temperature which will yield 90% ($T_{a-90}$) of the total possible recovery. Total possible recovery includes the amount of preactivation shrinkage.

Generally, where the skin layer of the laminate tape backing is relatively thin, the laminate will tend to contract or recover immediately. When the skin thickness is increased sufficiently the laminate can become heat shrinkable. This phenomenon can occur even when the elastomeric layer is formed from a non-heat shrinkable material. Further, by careful selection of the thicknesses of the elastomeric layer and the skin layer(s), the temperature at which the laminate recovers by a set amount can be controlled within a set range. This is termed skin controlled recovery where generally by altering the thickness or composition of the skin, one can raise the activation temperature of an elastomeric core by a significant degree, generally more than at least 10° F. (5.6° C.) and preferably by 15° F. (8.3° C.) and more. Although any skin thickness which is effective can be employed, too thick a skin will cause the laminate to remain permanently set when stretched. Generally, where a single skin is less than 30% of the laminate this will not occur. For most heat or time shrink materials the stretched elastomer must be cooled so that the energy released during stretching does not cause immediate heat activated recovery. Fine tuning of the shrink recovery mechanism can be accomplished by the amount of stretch. This overall control over the shrink recovery mechanism can be an extremely important advantage, for example, when the unactivated tape is used in a manufacturing process. This control permits adjustment of the recovery mechanism of the elastomeric laminate tape to fit the requirements of a manufacturing process rather than the need to adjust a manufacturing process to fit the shrink recovery mechanism of the elastomer itself.

Skin controlled recovery may also be used to control the slow or time shrink recovery mechanism, as with the heat shrink mechanism. This shrink recovery mechanism occurs as an intermediate between instant and heat shrink recovery. Skin layer and stretch ratio control of recovery is possible as in the heat shrink mechanism, with the added ability to change the shrink mechanism in either direction, i.e., to a heat or an instant shrink elastomeric laminate tape.

A time shrink recovery laminate tape will also exhibit some heat shrink characteristics and vice versa. For example, a time shrink laminate tape can be prematurely recovered by exposure to heat, e.g., at a time prior to 20 seconds after stretch.

Recovery can also be initiated for most time shrink and some low activation temperature heat shrink recovery laminates by mechanical deformation or activation. In this case, the laminate tape is scored, folded, wrinkled, or the like to cause localized stress fractures that cause localized premature folding of the skin, accelerating formation of the recovered microtextured laminate. Mechanical activation can be performed by any suitable method such as by using a textured roll, a scoring wheel, mechanical deformation or the like.

The laminate tape backings of the present invention may be formed by any convenient layer forming process such as pressing layers together, coextruding the layers or stepwise extrusion of layers, but coextrusion is a preferred process. Coextrusion per se is known and is described, for example, in U.S. Pat. Nos. 3,557,265 and 3,479,425. Tubular coextrusion or double bubble extrusion is also possible. The layers are typically coextruded through a specialized die and/or feedblock that will bring the diverse materials into contact while forming the laminate.

Whether the laminate backing is prepared by coating, lamination, sequential extrusion, coextrusion or a combination thereof, the laminate formed and its layers will preferably have substantially uniform thicknesses across the laminate backing. Preferably the layers are coextensive across the width and length of the laminate. With such a construction the microtexturing is substantially uniform over the elastomeric laminate surface. Laminates prepared in this manner have generally uniform elastomeric properties with a minimum of edge effects such as curl, modulus change, fraying and the like. Further, when wound as in a roll of tape, this will minimize formation of hard bands, winding problems, roll telescoping or the like.

The laminate backing of the invention has an unlimited range of potential widths, the width limited solely by the fabricating machinery width limitations. This allows fabrication of microtextured elastomeric tapes for a wide variety of potential uses.

After formation, the laminate tape backing can be stretched past the elastic limit of the skin, which deforms. The laminate tape backing then is recovered instantaneously, with time or by the application of heat, as discussed above. For heat recovery, the temperature of activation is determined by the materials used to form the laminate in the first instance. For any particular laminate, the activation temperature, either $T_{a-50}$ or $T_{a-90}$, can be adjusted by varying the skin/core ratio of the laminate, adjusting the percent stretch or the overall laminate thickness. The activation temperature used for a heat shrink laminate is generally at least 80° F. (26.7° C.), preferably at least 90° F. (32.2° C.) and most preferably over 100° F. (37.8° C.). When heat-activated, the stretched laminates are quenched on a cooling roller, which prevents the heat generated from the elongation from activating laminate recovery. The chill roll is below the activation temperature.

The composition of the present invention may also be used in improved non-tacky, microtextured, multi-layer elastomeric laminates, such as those described in U.S. Pat. Nos. 5,422,178 and 5,376,430, both of which are herein incorporated by reference in their entirety. The laminates of the present invention are comprised of an elastomeric polymeric core layer(s), which provides elastomeric properties to the laminate and one or more polymeric skin layers. Laminates can be prepared by coextrusion of the selected polymers for the skin and core layers or by application of one or more elastomer layer(s) onto one or more already formed skin layer(s). The novel, non-tacky microtextured laminate is obtained by stretching the laminate past the elastic limit of the skin layers and, while the laminate is stretched, selectively deactivating the elasticity of the laminate at predetermined regions. The laminate then recovers, in the non-deactivated regions, which can be instantaneous, over an extended time period, which is skin layer controllable, or by the application of heat, which is also skin layer controllable.

The selectively deactivated areas provide high-strength inelastic regions. The recovered regions can be microtextured or have detached skin layers.

These laminates may also be used in pressure-sensitive adhesive backed tapes.

In addition, the laminates may be used such as described in U.S. Pat. No. 5,462,708, which is herein incorporated by reference in its entirety. In particular, the shrink recovery mechanism of the laminate, after stretching and selective deactivation, depends on the conditions of film formation, the nature of the elastomeric layer(s), the nature of the skin layer(s), the manner in which the laminate film is stretched and the relative thicknesses of the elastomeric and skin layer(s). By controlling these variables, the laminate film can be designed to instantaneously recover, recover over time or recover upon heat activation. Generally, the core-to-single skin layer ratio will be at least 3, preferably, at least 5 and less than about 100 and most preferably at least 5 to about 75. The overall laminate thickness will be at least 1 mil, preferably at least 2 mils, although preferably less than 10 mils for cost and performance considerations. At core-to-skin layer ratios less than 3, the laminate has a tendency to not recover when stretched. A stretched and selectively deactivated laminate capable of instantaneous shrink is one in which the stretched, non-deactivated areas of the elastomeric laminate will recover more than 15% in 1 sec. A laminate capable of time shrink is one where the 15% recovery point takes place more than 1 sec., preferably more than 5 sec., most preferably more than 20 sec. after stretch, and a laminate capable of heat shrink is where less than 15% shrink recovery occurs to the laminate in the first 20 seconds after stretch and will remain capable of heat shrink for weeks after it is stretched. Percent recovery is the percent that the amount of shrinkage is of the stretched length minus the original length of the activated area. For heat-shrink laminates there will be an activation temperature which will initiate significant heat-activated recovery. The activation temperature used for a heat-shrink laminate will generally be the temperature that will yield 50% of the total possible recovery ($T_{a-50}$) and preferably this temperature is defined as the temperature which will yield 90% ($T_{a-90}$) of the total possible recovery. Total possible recovery includes the amount of preactivation shrinkage.

Also, as described in U.S. Pat. No. 5,468,428, which is herein incorporated by reference, the selective or preferential activation is produced by controlling the relative elastic modulus values of selected cross-sectional areas of the laminate to be less than modulus values of adjacent cross-sectional areas. The areas controlled to have reduced modulus will preferentially yield when subjected to stress. This will result in either preferential elastization of specified zones or fully elasticized laminates with higher strain regions, depending on the location of the areas of low modulus and the manner of stretch. Alternatively, the laminate could be treated to enhance or concentrate stress in selected regions. This will yield essentially the same results as providing low modulus regions. By either construction, the laminate can activate in selected regions at lower stretch ratios than would normally be required activate the entire laminate.

The modulus can be controlled by providing one or more layers of the laminate with relatively low and high modulus areas. This can be accomplished by selectively altering the physical or chemical characteristics of regions of one or more layers or by providing a layer(s) with regions of diverse chemical composition. Regionally enhanced stress can be induced by physical or chemical treatment of a layer(s) such as by ablation, scoring, corona treatment or the like.

The composition of the present invention may also be used in improved non-tacky, nonelastomeric materials capable of becoming elastomeric when stretched, as described in U.S. Pat. No. 5,429,856. Such materials comprise at least one elastomeric core and a surrounding nonelastomeric matrix, preferably prepared by coextrusion. The material of the present invention may be used in the elastomeric polymeric core region, which provides the elastomeric properties to the material and a polymeric matrix, which is capable of becoming microtextured at specified areas. The microtextured areas will correspond to sections of the material that have been activated from an inelastic to an elastomeric form. In preferred embodiments of the present invention, the matrix material further can function to permit controlled recovery of the stretched elastomer, modify the modulus of elasticity of the elastomeric material and/or stabilize the shape of the elastomeric material (e.g., by controlling further necking). The material is preferably prepared by coextrusion of the selected matrix and elastomeric polymers. The novel, non-tacky microtextured form of the material is obtained by stretching the material past the elastic limit of the matrix polymer in predetermined elastic containing regions. The laminate then recovers in these predetermined regions, which can be instantaneous, over an extended time period, which is matrix material controllable, or by the application of heat, which is also matrix material controllable.

In certain constructions, complex periodic macrostructures can form between selectively elasticized regions depending on the method and direction of stretch activation. This can result in elastics with a considerable degree of bulk formed with relatively small amounts of elastic. This is desirable for many applications, particularly in garments.

Another use for the compositions of the present invention is in film laminates as described in U.S. Pat. No. 5,620,780, which is herein incorporated by reference in its entirety. In particular, the composition may be used in a film laminate as an elasticized diaper fastening tab as per, e.g., U.S. Pat. No. 3,800,796. The one or more elastomeric core(s) could be placed at the desired location while providing nonelastic end portions. The elasticized film is preferably 10 mm to 50 mm wide for most conventional tape tab constructions. This provides adequate tension without having to stretch the tape too far onto the diaper front. This tab could be cut from film stock containing one or more elastomeric bands. Adhesive or a mechanical fastener (e.g., hook or loop) element could then be applied to one or more faces of the nonelastic end portions. However, the pressure-sensitive adhesive coated (or mechanical fastener containing) end portion for releasable attaching to the diaper front portion could be 8 to 15 mm wide while the end portion permanently attached to the diaper side is widened substantially, as disclosed in U.S. Pat. No. 5,399, 219.

The present invention may also be used in an extensible elastic tab designed to be adhered to the edge of an article, formed using a coextruded elastic film comprising at least one elastic layer and at least one second layer on at least a first face of the elastic layer, such as described in U.S. Pat. No. 6,159, 584, which is herein incorporated by reference. One face of the coextruded elastic film is attached to at least a partially extensible nonwoven layer. The partially expandable, or extensible nonwoven layer has at least one first portion with limited extensibility in a first direction and at least one second inextensible portion in the first direction. The extensible elastic tab when stretched to the extension limit of the first portion or portions in the first direction will elastically recover at least 1.0 cm, preferably at least 2 cm providing an elastic tab having a Useful Stretch Ratio (as defined in the Examples of U.S. Pat. No. 6,159,584) of at least 30 percent. The Useful Stretch Ratio includes the portion of the elastic recovery length having an elastic recovery force of greater than 20 grams/cm force, but below a given extension which generally is 90 percent of the extension limit. Further, the elastic tab in the region of the Useful Stretch Ratio preferably has an incremental extension force of less than about 300 grams/cm. The coextruded elastic film second layer is preferably a relatively inelastic material or blend and provided on both faces of the at least one elastic layer.

The present invention may also be used in pressure sensitive adhesive backed tape, such as that described in U.S. Pat. No. 5,800,903, which is herein incorporated by reference in its entirety.

The composition of the present invention may also be used in a thin multi-layer elastic film that stretches in the transverse direction, such as described in U.S. Pat. No. 6,472,084, which is herein incorporated by reference. The elastic film has a first layer, a second layer and a core layer. The film has activated zones and non-activated zones. The activated zones have sufficient elasticity to stretch to at least 200% while maintaining a permanent set percent of no more than 5%. The non-activated zones have sufficient non-elasticity to stretch at least 200% while maintaining a permanent set percent of up to 5%. The activated zones have a tear strength as measured by the Elmendorf Tear Test of 30 g while the non-activated zones have a tear strength as measured by the Elmendorf Tear Test of at least 50 g. The elastic film is particularly useful in products such as elastic waistbands, side panels and the like for use in products such as absorbent, disposable products. The superior tear-strength of the film prevents tearing during use of the film and promotes longer-lasting applications of the film. In addition, the superior tear-strength of the film prevents existing tears from propagating throughout the film.

The high performance elastic behavior is defined by tensile set less than about 50 percent and force relaxation less than about 20 percent after 300 percent elongation. The procedure to measure hysteresis of a sample is as follows:

1. A sample of the film or laminate (6 inches long and 1 inch wide strip) is prepared with the length in the intended direction of use. The sample is placed lengthwise in the jaws (separated by 4 inches) of a tensile testing machine.
2. The sample is pulled a first time (cycle 1 elongation) at the rate of 20 inches per minute to the desired elongation (for example, 200 percent)
3. The force upon reaching the desired elongation is noted.
4. The sample is held at the desired elongation for 30 seconds after which the force is noted.
5. The instrument is returned to its initial position (zero elongation)
6. The sample is held in a relaxed state for 30 seconds.
7. The sample is pulled a second time (cycle 2 elongation) at the rate of 20 inches per minute to the desired elongation. The amount of movement in the tensile testing machine jaw before the film exerts any force is noted.
8. The sample is held at the desired elongation for 30 seconds and then relaxed.

Tensile set is a measure of the permanent deformation of the sample as a result of the initial elongation, hold, and relax cycle. Specifically, tensile set is the elongation measured in the second cycle divided by the initial sample length (2 inches).

When the inventive blend is used in multilayer structures such as those described within U.S. Pat. No. 6,472,084 B1 the overall structure is measured using the Elmendorf Tear Test in accordance with ASTM D 1922, entitled Standard Test Method for Propagation Tear Resistance of Plastic Film and Thin Sheeting by Pendulum Method.

In another aspect of the invention, the elastomeric composition is fabricated into an apertured film. In another aspect, the apertured film may be laminated to a nonwoven and elasticity may be introduced by methods described elsewhere in this document. Depending on the apertured structure, the film or laminate is preferred to have a web porosity of at least 1 cubic feet of air per minute per square foot of material (e.g. film or laminate) (CFM/sq. ft), preferably at least 10 CFM/sq. ft, preferably at least 100 CFM/sq. ft., and more preferably at least 200 CFM/sq. ft. Web porosity is a measure of the ability of the film or laminate to allow air flow in end use. In personal care articles, sufficient air flow in end-use can prevent undesirable moisture accumulation which can result in skin irritation. Web porosity may be measured using the ASTMD-737 method.

The composition of the present invention may also be used in a composite material comprising an elastomeric three dimensional, apertured film having a planar surface and a three dimensional surface, and a carrier material bonded to at least the planar surface of the elastomeric film, such as described in WO-A-199815399, which is herein incorporated by reference. Such a composite material may be made by a process comprising: (a) supplying successive portions of a molten or semi-molten elastomeric film having a top surface and a bottom surface, the elastomeric film being supplied at a predetermined temperature; (b) supplying a carrier material onto the top surface of the elastomeric film; (c) optionally providing a compressive force to the film and the carrier material; (d) subjecting the bottom surface of the elastomeric film to the action of a fluid pressure differential; and, (e) maintaining the pressure differential for a period of time sufficient to form a plurality of three-dimensional apertured structures in the elastomeric film and to bond the carrier material to the top surface of the elastomeric film to form the breathable, elastomeric composite material.

Another aspect of the invention includes a composite material comprising an elastomeric three-dimensional, apertured film, such as described in U.S. Pat. No. 5,733,628, which is herein incorporated by reference, having a planar surface and a three-dimensional surface, the three-dimensional surface having a plurality of three-dimensional protuberances wherein each protuberance defines an aperture, and a carrier material bonded to at least the planar surface of the elastomeric film, wherein the film has elastic hysteresis properties such that the film has about 10% or less tensile set and about 21% or less force relaxation after about a 300% elongation using the test contained therein and wherein the composite material comprises the composition of the invention. The invention also relates to an absorbent article comprising a topsheet formed of this composite material, an absorbent pad and a fluid impervious backsheet. The present invention also relates to a three-dimensional, breathable elastic film laminate comprising an elastomeric film and a carrier material adhered thereto. The laminate is particularly useful as a layer in disposable products including absorbent products and wound dressings and the like. However, the present invention is not limited to such applications and the film laminate of the present invention may be used advantageously to produce other products comprising an elastomeric film having desired high stretch characteristics.

The composition of the present invention may also be used in a composite material comprising an elastomeric three-dimensional, apertured film having a first surface and a three-dimensional surface with a plurality of protuberances, wherein each protuberance defines an aperture at a terminal end of said protuberance, and a film carrier material bonded to at least one of the first surface and the three-dimensional surface of the elastomeric film, said composite material comprising a continuous supply of the film carrier material coextruded with the elastomeric film material thereby forming a laminate which is apertured in a secondary process, said composite material having elastic hysteresis properties such that the composite material has less than 10% tensile set after elongation of about 300%, such as described in U.S. Pat. No. 6,303,208, which is herein incorporated by reference.

The film may also be perforated by means of a conventional high intensity laser apparatus designed to convey a flexible plastic film strip or web through an adjustable laser-exposure station to produce a plurality of spaced holes and adjacent columns of such holes, each hole having the predetermined diameter and spacing, such as described in U.S. Pat. No. 5,336,554, which is herein incorporated by reference.

Breathability may also be provided via an elastic web into which is inserted, by a slitting mechanism, a plurality of slits, a majority of them having their major axes oriented in such a direction that they are within 45° of a common direction. When a tensile force is applied to the web in the direction in which the major axes are pointed, the ligaments between the slits stretch and also neck, causing the slits to widen into apertures. The apertures then provide breathability to the web. The level of breathability increases with an increase in the elongation of the web. Such slitting may be accomplished as described in US Patent Application Publication No. 2005-018513, which is herein incorporated by reference.

A breathable laminate comprising the composition of the present invention may also be made by a method for forming an elastic, breathable film comprising the steps of: a) filling a higher crystalline, predominantly linear polymer with a filler to form a filled polymer such that said filled polymer contains at least 60 percent by weight filler; b) dry-blending a thermoplastic elastomer with the filled polymer to form a blended elastomer composition, such that the said blended elastomer composition includes between about 25 and 70 percent filler by weight, between about 5 and 30 percent higher crystalline polymer by weight, and between about 15 and 60 percent by weight elastomer; c) extruding the blended elastomer composition into a film; d) orienting said film in a machine direction between about 2 and 5 times, such that said film produced has a basis weight of between about 15 and 60 gsm and demonstrates a breathability greater than about 100 g/m$^2$/24 hours and a load loss value at 50 percent elongation of less than about 50 percent. Such a method is described in WO2005/023544A1, which is herein incorporated by reference.

Suitable fillers may include calcium carbonate ($CaCO_3$), various clays, silica ($SiO_2$), alumina, barium sulfate, sodium carbonate, talc, magnesium sulfate, titanium dioxide, zeolites, aluminum sulfate, cellulose-type powders, diatomaceous earth, gypsum, magnesium sulfate, magnesium carbonate, barium carbonate, kaolin, mica, carbon, calcium oxide, magnesium oxide, aluminum hydroxide, pulp powder, wood powder, cellulose derivatives, polymeric particles, chitin and chitin derivatives and combinations thereof.

The filler particles may optionally be coated with a fatty acid, such as stearic acid or behenic acid, and/or other material in order to facilitate the free flow of the particles (in bulk) and their ease of dispersion in to the carrier polymer. One such filler is calcium carbonate sold under the brand Supercoat®, of Imerys of Roswell, Ga. Another is Omyacarb® 2 SS T of Omya, Inc. North America of Proctor, Vt. The latter filler is coated with stearic acid. Desirably, the amount of filler in the product film (final film formulation) is between about 40 and 70 percent. More desirably, the amount of filler in the product film is between about 45 and 60 weight percent.

The invention also relates to an elastic, breathable film comprising a blended thermoplastic elastomer and a filled higher crystalline predominantly linear polymer, said film comprising between about 25 and 70 weight percent filler, between about 5 and 30 by weight percent higher crystalline linear polymer, and between about 15 and 60 by weight elastomeric polymer, wherein said filler is closely associated with said higher crystalline linear polymer, and further wherein said film demonstrates a load loss value at a 50 percent elongation of less than about 50 percent, and a breathability of greater than about 100 g/m$^2$/24 hours, and wherein the film comprises the composition of the present invention. The film may be stretched, thus forming microvoids to render the film microporous and subsequently breathable as described in and using methods described in WO2005/023544A1. Microvoids are defined as open spaces on the order of 1 to 100 microns that can be created as a consequence of delamination and cavitation around filler particles. Though not intended to be limited by any particular theory, it is thought that when microvoids form continuous, albeit tortuous pathways, through the thickness of the film, breathability is possible. Also, it is believed their small dimensions coupled with the inherent hydrophobicity of the polymer-based film imparts hydrohead performance.

The composition of the present invention may also be used in a method for forming an elastic, breathable film laminate that includes the steps of filling a higher crystalline, predominantly linear polymer with a filler to form a filled polymer such that the filled polymer contains at least 60 percent by weight filler, and desirably at least 70 percent by weight filler; dry-blending a thermoplastic elastomer comprising the composition of the present invention with the filled polymer to form a blended elastomeric composition, such that the blended elastomeric composition includes between about 25 and 70 percent filler by weight, between about 5 and 30 percent higher crystalline polymer by weight, and between about 15 and 60 percent by weight elastomer polymer; extruding the blended elastomeric composition into a film; orienting the film in a machine direction between about 2 and 5 times, such that the film produced has a basis weight of between about 15 and 60 gsm and demonstrates a breathability greater than 100 g/m$^2$/24 hours and a load loss value at 50 percent elongation of less than 50 percent, bonding the produced film to a nonwoven layer to produce a film layer/ nonwoven layer laminate, such as described in WO05/021262A1, which is herein incorporated by reference. This general process may comprise the concentrate letdown process, wherein one resin is used as a carrier resin to make a concentrate with a filler. In the current application, a carrier resin, typically a high melt index or melt flow rate/low viscosity resin with higher density level (0.910-0.960 g/cc) for polyethylene-based polymers, and a density level between about 0.89 g/cc and 0.90 g/cc for polypropylene-based polymers, may be used to disperse high loadings of filler. The concentrate is let down (combined) with elastic resin to dilute the final filler content to a desired percentage.

Desirably, a concentrate of "filled polymer" (carrier resin and filler) is made with the filler and the higher crystalline carrier polyolefin in the range of between about 60-85 percent by weight filler, more desirably 70-85 percent by weight filler. It is also desirable to reduce the amount of the higher crystalline polymer in the final composition so as to have the least impact on the elastic performance of the elastomeric polymer phase. The elastic polymer is blended with the filled polymer concentrate resin prior to introduction into the film screw extruder in a blending station as a "letdown" resin. The concentration of the thermoplastic elastomer is then generally determined by the desired filler level in the final composition. The level of filler will necessarily affect breathability as well as elastic properties of the film. In one embodiment it is desirable for the filler to be present in the filled polymer in an amount of greater than 80 weight percent, such that the film demonstrates the desired properties.

As an example, the filler may be present in a film configuration of between about 25-65 weight percent, the elastomer may be present in a range between about 15-60 weight percent, and the higher crystalline polymer may be present in a range of between about 5-30 weight percent.

In an aspect of the invention, a laminate comprising the microporous elastomeric film with at least 20 weight percent filler particles, when laminated to a melt blown nonwoven, has a hydrohead value of at least about 10 centimeters, preferably at least about 20 centimeters, more preferably at least about 30 centimeters, even more preferably at least about 40 centimeters, even more preferably at least about 50 centimeters, even more preferably at least about 75 centimeters, and most preferably at least about 90 centimeters. A suitable technique for determining the hydrohead value is the Hydrostatic Pressure Test which is described in further detail herein below. Hydrohead values less than necessary for a particular application are undesirable. For example, a hydrohead value less than desirable can result in the strike through of liquids (e.g. leakage), such as urine through a diaper backsheet, during use.

In still a further alternative embodiment, as described in WO05/021262A1, the composition of the present invention may also be used in an elastic, breathable film layer/nonwoven layer laminate that includes a film, including a thermoplastic elastomer and a filled higher crystalline polymer. The film includes between about 25 and 70 weight percent filler, between about 5 and 30 by weight percent higher crystalline polymer, and between about 15 and 60 by weight percent elastomer. The filler is closely associated with said higher crystalline polymer. The nonwoven layer is bonded to the film and the film/nonwoven laminate demonstrates a load loss value at 50 percent elongation, when stretched to a 70 percent elongation, of less than about 75 percent and a breathability of greater than about 100 g/m$^2$/24 hours. In still a further alternative embodiment of the laminate, the higher crystalline polymer is a polyethylene or polyethylene copolymer having a melt index greater than 10 g/10 min and a density greater than 0.915 g/cc. In a further alternative embodiment of the laminate, the higher crystalline polymer is a polyethylene or polyethylene copolymer having a melt index greater than about 20 g/10 min. In still further alternative embodiments of the laminate, the higher crystalline polymer has a density of about 0.917 g/cc, of greater than about 0.917 g/cc, has a density of between about 0.917 g/cc and 0.960 g/cc or has a density of between about 0.923 g/cc and 0.960 g/cc. In an additional alternative embodiment of the laminate, the higher crystalline polymer is a polypropylene or polypropylene copolymer having a melt flow rate of greater than 20 g/10 min. and a density between about 0.89 g/c and 0.90 g/cc. After bonding, the laminate may be further processed. Following lamination, the multilayered laminate may be subjected to numerous stretching and manufacturing processes. For instance, such laminate may be slit and/or necked. Alternatively, the laminate may be stretched in a machine direction or cross-machine direction. For instance, in one embodiment, it is desirable to stretch the film/support layer laminate in either traditional grooved rolls having peaks and valleys, or grooved rolls formed from discs along an axis. For instance, such laminate may be coursed through a series of grooved rolls that have grooves in the CD direction. Such processing step may provide additional desired attributes to the laminate, such as softness, without sacrificing elasticity or breathability.

In an additional embodiment, the laminate is incorporated into a personal care product and may provide an aesthetically pleasing appearance and a pleasant tactile touch. In further alternative embodiments, the laminate is incorporated into a personal care product as a hook engageable outercover, as a liner or outercover, or it may be incorporated into a recreational outdoor cover or a disposable protective garment.

In addition, the present invention relates to a breathable elastomeric film, such as described in WO98/29479A1, which is herein incorporated by reference, wherein the film comprises a composition of the present invention or the ethylene/α-olefin component alone and at least 30% by weight of a filler having a particle size that contributes to pore formation. Preferably, the polymeric resin material has a density of from about 0.850 to about 0.917 g/cc. Preferably, the film includes from about 45 to about 60% filler by weight of the filled resin.

For certain applications of the present invention, the breathable film has an immediate recovery length that is at least about 50% of its elongation following a stretch cycling that achieved a stretched length of about 160% of the unbiased length. In yet other applications, the film may have an immediate recovery length that is at least about 50% its elongation length following a stretch cycling that achieved a stretched length of about 200% of the unbiased length, such as described in WO98/29479A1.

The present invention is also directed to a process for preparing a breathable elastomeric film as described in WO98/29479A1, wherein the process further comprises providing a material comprising a polymer of the present invention; adding to the polymer at least 30% by weight of a filler having a particle size that contributes to pore formation to form a filled resin; forming a film having a first length from the filled resin; and stretching the film to form a microporous film.

The invention also relates to a breathable laminate including at least one support layer and an oriented microporous film that includes an elastomeric resin and at least 30% by weight of the film of a filler having a particle size that contributes to pore formation, such as described in U.S. Pat. No.

6,015,764, which is herein incorporated by reference, wherein the elastomeric resin comprises the composition of the present invention.

The present invention also is directed to a process for producing a laminate including at least one support layer and an oriented microporous elastomeric film including the steps of providing a filled film layer having a first length that includes at least 30% by weight of a filler having a particle size that contributes to pore formation and an elastic polymeric material that is capable of being stretched at room temperature to at least twice its original length and, upon release of the stretching force, will retract approximately to its original unstretched length; stretching the filled film to produce a microporous film having a second length; and bonding at least one support layer to the microporous film to form a laminate, such as described in U.S. Pat. No. 6,015,764, wherein the elastic polymeric material comprises a composition of the present invention.

Such films and laminates have a wide variety of uses including, but not limited to, applications in personal care absorbent articles including diapers, training pants, sanitary napkins, incontinence devices, bandages and the like. These same films and laminates also may be used in items such as surgical drapes and gowns as well as various articles of clothing either as the entire article or simply as a component thereof.

The composition of the present invention may also be used in a method wherein a predetermined thickness of a layer of a carrier material is introduced onto a top surface of an elastomeric film material just prior to or directly at the point of forming the three-dimensional characteristics of the film, as described in U.S. Pat. No. 6,808,789, which is herein incorporated by reference, wherein the elastomeric film material comprises a composition of the present invention. The carrier material is supplied under an appropriate tension to the film material. In preferred embodiments, the elastic film is formed into a three-dimensional structure using a vacuum or pressure differential process. The carrier material covers a predetermined area of the elastomeric film surface and partially embeds or fuses onto the top surface of the elastomeric film material.

The composition of the present invention may also be used in an activated, laminated web, such as described in EP1637320A1, which is herein incorporated by reference, wherein the activation is carried out before the component webs in the laminate have been bonded. After activation, the component webs are bonded in a face to face relationship by using the pressure generated by the activating process provided sufficient heat is applied to the interface between the webs.

Additionally, the composition of the present invention may be used in a tear resistant laminate comprising an elastic polymeric film that has a first nonwoven web formed of nonelastic fibers bonded to a top surface of the elastic polymeric film and a second nonwoven web formed of nonelastic fibers bonded to a bottom surface of the elastic polymeric film. Each of the nonwoven webs has a permanent deformation range from about 20% to about 200%, measured in a predefined transverse direction, and an ultimate force to break of greater than 1,500 g/in. in said predefined transverse direction. The laminate has an elastic elongation value greater than the elastic elongation values of the first and second nonwoven webs, and an ultimate force to break value of at least 3,000 g/in. Such a laminate is described in US. Patent Application Publication No. 2003/0022582, which is herein incorporated by reference.

The composition of the present invention may also be used in a laminate comprising an elastic web, a first nonwoven bonded to a first side of the elastic web, and a second nonwoven bonded to a second side of the elastic web, wherein the laminate includes at least one dead lane or stiffened lane extending through the laminate, and at least one elastic lane, such as described in U.S. Pat. No. 6,255,236, which is herein incorporated by reference.

In another embodiment, a web includes a repeating pattern of elongated high stress lanes aligned substantially normal to a stretch force axis. The pattern of high stress lanes is defined by a plurality of depressions which protrude away from an uppermost contacting plane of the web. The depressions have substantially vertical sidewalls. The high stress lanes have a width defined by a distance between the substantially vertical sidewalls of the depressions on either side of the lane. The repeating pattern of lanes have a separation distance between the lanes. The depressions are interrupted by connecting members extending between adjacent high stress lanes, such as described in US Patent Application Publication No. 2005/0003152, which is herein incorporated by reference.

Additionally, the composition of the present invention may be used in a method for producing a laminated film having at least one three-dimensional apertured or non-apertured film material laminated to at least one flat or three-dimensional apertured or non-apertured film material and the films produced thereby, such as described in U.S. Pat. No. 5,698,054, which is herein incorporated by reference.

In another embodiment, the composition of the present invention is used in an absorbent article with a body facing side, the absorbent article comprising: a backsheet opposite the body facing side; an absorbent core between the backsheet and the body facing side; and a composite topsheet between the absorbent core and the body facing side, said composite topsheet comprising: a resilient three-dimensional apertured formed film between the absorbent core and the body facing side, said formed film having a male side with protrusions and a female side with lands opposite the male side, and small scale apertures having a mesh count; a nonwoven web of fibers between the formed film and the body facing side of the absorbent article; and a plurality of three-dimensional conical shaped apertures in the nonwoven layer that extend through the formed film, said apertures having a mesh count which is less than the mesh count of the small scale apertures, such absorbent article as described in U.S. Pat. No. 6,849,319, which is herein incorporated by reference.

The composition of the present invention may also be used in a composite material comprising at least one layer of a thermally sensitive three-dimensional first material laminated to at least one layer of a second material without causing thermal distortion or damage to the first or second materials; wherein the first material comprises a three-dimensional non-apertured material having a planar side and a three-dimensional side, the three-dimensional side of the first, non-apertured material defining a plurality of non-apertured microprotuberances, each microprotuberance having a thickness and mass that are less than a thickness and mass of the material forming the planar side of the first, non-apertured material; and the second material comprises a three-dimensional, apertured material having a planar side and a three-dimensional side, the three-dimensional side of the second, apertured material defining a plurality of apertured microprotuberances, each apertured microprotuberance having at least one side wall which terminates at an aperture, each microprotuberance having a thickness and mass that are less than a thickness and mass of the material forming the planar side of the second, apertured material, wherein the three dimensional, apertured side of the second material is laminated to the planar side of the first material, such as described in U.S. Pat. Nos. 5,635,275 and 5,635,276, both of which are herein incorporated by reference.

The invention also relates to a method for the manufacture of a laminated composite film comprising: a) supplying at least one layer of a first thermoplastic material at a sufficiently elevated temperature and at a sufficient mass in order to achieve a bond between the first material and a second material, the first material having a top surface and a bottom surface; b) passing successive portions of the first material into contact with a continuous moving perforated member having perforations which extend through the perforated member, subjecting the bottom surface of the first material to the action of a fluid pressure differential, the fluid pressure differential causing portions of the first material to flow into the perforations of the continuous moving perforated member; c) maintaining the fluid pressure differential for a period of time sufficiently for a plurality of microprotuberances to be formed in the first material, the microprotuberances having a thickness and mass that are less than a thickness and mass of the material forming the top surface of the first material; d) supplying at least one layer of the second material comprising a thin, thermally sensitive thermoplastic material, the second material having a top surface and a bottom surface such that the top surface or the bottom surface of the second material is brought into contact with the top surface of the first material after the protuberances have been formed in the first material, wherein the second material laminates or adheres to the first material without substantially distorting the first material or the second material; and, e) continuously removing the laminated first and second materials from the moving perforated member, such as described in U.S. Pat. No. 5,783,014, which is herein incorporated by reference, wherein the laminated composite film comprises the composition of the present invention.

The following examples are presented to exemplify embodiments of the invention. All numerical values are approximate. When numerical ranges are given, it should be understood that embodiments outside the stated ranges may still fall within the scope of the invention. Specific details described in each example should not be construed as necessary features of the invention.

EXAMPLES

Testing Methods

In the examples that follow, the following analytical techniques are employed:

GPC Method for Samples 1-4 and A-C

An automated liquid-handling robot equipped with a heated needle set to 160° C. is used to add enough 1,2,4-trichlorobenzene stabilized with 300 ppm Ionol to each dried polymer sample to give a final concentration of 30 mg/mL. A small glass stir rod is placed into each tube and the samples are heated to 160° C. for 2 hours on a heated, orbital-shaker rotating at 250 rpm. The concentrated polymer solution is then diluted to 1 mg/ml using the automated liquid-handling robot and the heated needle set to 160° C.

A Symyx Rapid GPC system is used to determine the molecular weight data for each sample. A Gilson 350 pump set at 2.0 ml/min flow rate is used to pump helium-purged 1,2-dichlorobenzene stabilized with 300 ppm Ionol as the mobile phase through three Plgel 10 micrometer (μm) Mixed B 300 mm×7.5 mm columns placed in series and heated to 160° C. A Polymer Labs ELS 1000 Detector is used with the Evaporator set to 250° C., the Nebulizer set to 165° C., and the nitrogen flow rate set to 1.8 SLM at a pressure of 60-80 psi (400-600 kPa) $N_2$. The polymer samples are heated to 160° C. and each sample injected into a 250 μl loop using the liquid-handling robot and a heated needle. Serial analysis of the polymer samples using two switched loops and overlapping injections are used. The sample data is collected and analyzed using Symyx Epoch™ software. Peaks are manually integrated and the molecular weight information reported uncorrected against a polystyrene standard calibration curve.

Standard CRYSTAF Method

Branching distributions are determined by crystallization analysis fractionation (CRYSTAF) using a CRYSTAF 200 unit commercially available from PolymerChar, Valencia, Spain. The samples are dissolved in 1,2,4 trichlorobenzene at 160° C. (0.66 mg/mL) for 1 hr and stabilized at 95° C. for 45 minutes. The sampling temperatures range from 95 to 30° C. at a cooling rate of 0.2° C./min. An infrared detector is used to measure the polymer solution concentrations. The cumulative soluble concentration is measured as the polymer crystallizes while the temperature is decreased. The analytical derivative of the cumulative profile reflects the short chain branching distribution of the polymer.

The CRYSTAF peak temperature and area are identified by the peak analysis module included in the CRYSTAF Software (Version 2001.b, PolymerChar, Valencia, Spain). The CRYSTAF peak finding routine identifies a peak temperature as a maximum in the dW/dT curve and the area between the largest positive inflections on either side of the identified peak in the derivative curve. To calculate the CRYSTAF curve, the preferred processing parameters are with a temperature limit of 70° C. and with smoothing parameters above the temperature limit of 0.1, and below the temperature limit of 0.3.

DSC Standard Method (Excluding Samples 1-4 and A-C)

Differential Scanning Calorimetry results are determined using a TAI model Q1000 DSC equipped with an RCS cooling accessory and an autosampler. A nitrogen purge gas flow of 50 ml/min is used. The sample is pressed into a thin film and melted in the press at about 175° C. and then air-cooled to room temperature (25° C.). 3-10 mg of material is then cut into a 6 mm diameter disk, accurately weighed, placed in a light aluminum pan (ca 50 mg), and then crimped shut. The thermal behavior of the sample is investigated with the following temperature profile. The sample is rapidly heated to 180° C. and held isothermal for 3 minutes in order to remove any previous thermal history. The sample is then cooled to −40° C. at 10° C./min cooling rate and held at −40° C. for 3 minutes. The sample is then heated to 150° C. at 10° C./min. heating rate. The cooling and second heating curves are recorded.

The DSC melting peak is measured as the maximum in heat flow rate (W/g) with respect to the linear baseline drawn between −30° C. and end of melting. The heat of fusion is measured as the area under the melting curve between −30° C. and the end of melting using a linear baseline.

GPC Method (Excluding Samples 1-4 and A-C)

The gel permeation chromatographic system consists of either a Polymer Laboratories Model PL-210 or a Polymer Laboratories Model PL-220 instrument. The column and carousel compartments are operated at 140° C. Three Polymer Laboratories 10-micron Mixed-B columns are used. The solvent is 1,2,4 trichlorobenzene. The samples are prepared at a concentration of 0.1 grams of polymer in 50 milliliters of solvent containing 200 ppm of butylated hydroxytoluene (BHT). Samples are prepared by agitating lightly for 2 hours at 160° C. The injection volume used is 100 microliters and the flow rate is 1.0 ml/minute.

Calibration of the GPC column set is performed with 21 narrow molecular weight distribution polystyrene standards with molecular weights ranging from 580 to 8,400,000, arranged in 6 "cocktail" mixtures with at least a decade of separation between individual molecular weights. The standards are purchased from Polymer Laboratories (Shropshire, UK). The polystyrene standards are prepared at 0.025 grams in 50 milliliters of solvent for molecular weights equal to or greater than 1,000,000, and 0.05 grams in 50 milliliters of solvent for molecular weights less than 1,000,000. The polystyrene standards are dissolved at 80° C. with gentle agitation for 30 minutes. The narrow standards mixtures are run first and in order of decreasing highest molecular weight component to minimize degradation. The polystyrene standard peak molecular weights are converted to polyethylene molecular weights using the following equation (as described in Williams and Ward, *J. Polym. Sci., Polym. Let.*, 6, 621 (1968)): $M_{polyethylene}=0.431(M_{polystyrene})$.

Polyethylene equivalent molecular weight calculations are performed using Viscotek TriSEC software Version 3.0.

Compression Set

Compression set is measured according to ASTM D 395. The sample is prepared by stacking 25.4 mm diameter round discs of 3.2 mm, 2.0 mm, and 0.25 mm thickness until a total thickness of 12.7 mm is reached. The discs are cut from 12.7 cm×12.7 cm compression molded plaques molded with a hot press under the following conditions: zero pressure for 3 min at 190° C., followed by 86 MPa for 2 min at 190° C., followed by cooling inside the press with cold running water at 86 MPa.

Density

Samples for density measurement are prepared according to ASTM D 1928. Measurements are made within one hour of sample pressing using ASTM D792, Method B.

Flexural/Secant Modulus/Storage Modulus

Samples are compression molded using ASTM D 1928. Flexural and 2 percent secant moduli are measured according to ASTM D-790. Storage modulus is measured according to ASTM D 5026-01 or equivalent technique.

Optical Properties

Films of 0.4 mm thickness are compression molded using a hot press (Carver Model #4095-4PR1001R). The pellets are placed between polytetrafluoroethylene sheets, heated at 190° C. at 55 psi (380 kPa) for 3 min, followed by 1.3 MPa for 3 min, and then 2.6 MPa for 3 min. The film is then cooled in the press with running cold water at 1.3 MPa for 1 min. The compression molded films are used for optical measurements, tensile behavior, recovery, and stress relaxation.

Clarity is measured using BYK Gardner Haze-gard as specified in ASTM D 1746.

45° gloss is measured using BYK Gardner Glossmeter Microgloss 45° as specified in ASTM D-2457

Internal haze is measured using BYK Gardner Haze-gard-based on ASTM D 1003 Procedure A. Mineral oil is applied to the film surface to remove surface scratches.

Mechanical Properties—Tensile, Hysteresis, and Tear

Stress-strain behavior in uniaxial tension is measured using ASTM D 1708 microtensile specimens. Samples are stretched with an Instron at 500% min$^{-1}$ at 21° C. Tensile strength and elongation at break are reported from an average of 5 specimens.

300% Hysteresis and Tensile Tests at Ambient Conditions

Inventive and comparative examples (Tables 19, 20, 21, 22) were formulated by weighing out the components. They were then introduced to the Haake mixer preheated to 190° C. and set at 40 rpm rotor speed. After torque reached steady state (typically three to five minutes), the sample was then removed and allowed to cool. The blends were then molded in following method.

Compression molded plaques are prepared by weighing out the necessary amount of material to fill a 9 inch long by 6 inch wide by 0.5 millimeter thick mold. The material and the mold are lined with Mylar film and placed between chrome coated metal sheets and then the ensemble is placed into a PHI laminating press model PW-L425 (City of Industry, Calif.) preheated to 190° C. The material is allowed to melt for 5 minutes under minimal pressure. Then a force of 10000 pounds is applied for 5 minutes. Next, the force is increased to 20000 pounds and 1 minute is allowed to elapse. Afterwards, the ensemble is placed between 25° C. water-cooled platens and cooled for 5 minutes. The molded plaque is then removed from the mold and is aged at ambient conditions (about 20° C., 50% relative humidity) for at least 24 hours before testing.

The 300% hysteresis test at ambient conditions is performed at about 20° C. with 50% relative humidity using an Instron™ 5564 (Canton, Mass.) equipped with pneumatic grips and fitted with a 2 kN pound tension load cell. Compression molded plaques are prepared according to the compression molding aforementioned procedure. Microtensile specimens (ASTM D1708) are extracted of the compression molded plaques using a NAEF (Bolton Landing, N.Y.) B-36 punch. After proper calibration of the load cell, the microtensile (ASTM 1708) specimen is oriented parallel to the displacement direction of the crosshead and then is gripped using a grip separation of 22.25 mm. This separation of 22.25 mm is also taken as the gauge length of the sample. The sample is then stretched to 300% strain at a rate of 500% min$^{-1}$ (111.25 mm/min). The crosshead direction is then immediately reversed at then returned to the starting grip separation also at 500% min$^{-1}$ (111.25 mm/min). The crosshead direction is then again reversed such that the sample is then extended at 500% min$^{-1}$ (111.25 mm/min). During this loading step, the strain corresponding to a tensile stress of 0.05 MPa (megapascals) is taken as the permanent set.

The tensile test at ambient conditions is performed at about 20° C. with 50% relative humidity. Specimens are prepared according to the compression molding procedure described above. An Instron™ 5564 (Canton, Mass.) equipped with pneumatic grips and fitted with a 2 kN pound tension load cell is used. Microtensile specimens (ASTM D1708) are extracted of the compression molded plaques using a NAEF (Bolton Landing, N.Y.) B-36 punch. After proper calibration of the load cell, the microtensile (ASTM 1708) specimen is oriented parallel to the displacement direction of the crosshead and then is gripped using a grip separation of 22.25 mm. This separation of 22.25 mm is also taken as the gauge length of the sample. The sample is then stretched at a rate of 500% min$^{-1}$ (111.25 mm/min) until the specimen breaks. The peak tensile stress is taken as the tensile strength of the material. The corresponding strain is taken as the elongation at break.

Strain is measured as a percentage and is defined as the crosshead displacement divided by the original grip separation of 22.25 mm and then multiplied by 100. Stress is defined as force divided by the cross sectional area of the narrow portion of the gauge portion of the ASTM D1708 microtensile specimen prior to deformation.

Uncertainty for tensile strength measurements is estimated to be about less than 20% of the measured values.

Uncertainty for elongation to break measurements is estimated to be about less than 20% of the measured values.

Uncertainty for 2% secant modulus is estimated to be about less than 30% of the measured values.

Uncertainty for permanent set measurements is estimated to be about ±5% strain.

TMA

Thermal Mechanical Analysis (Penetration Temperature) is conducted on 30 mm diameter×3.3 mm thick, compression molded discs, formed at 180° C. and 10 MPa molding pressure for 5 minutes and then air quenched. The instrument used is a Perkin-Elmer TMA 7. In the test, a probe with 1.5 mm radius tip (P/N N519-0416) is applied to the surface of the sample disc with 1N force. The temperature is raised at 5° C./min from 25° C. The probe penetration distance is measured as a function of temperature. The experiment ends when the probe has penetrated 1 mm into the sample.

DMA

Dynamic Mechanical Analysis (DMA) is measured on compression molded disks formed in a hot press at 180° C. at 10 MPa pressure for 5 minutes and then water cooled in the press at 90° C./min. Testing is conducted using an ARES controlled strain rheometer (TA Instruments) equipped with dual cantilever fixtures for torsion testing.

A 1.5 mm plaque is pressed and cut in a bar of dimensions 32×12 mm. The sample is clamped at both ends between fixtures separated by 10 mm (grip separation ΔL) and subjected to successive temperature steps from –100° C. to 200° C. (5° C. per step). At each temperature the torsion modulus G' is measured at an angular frequency of 10 rad/s, the strain amplitude being maintained between 0.1 percent and 4 percent to ensure that the torque is sufficient and that the measurement remains in the linear regime.

An initial static force of 10 g is maintained (auto-tension mode) to prevent slack in the sample when thermal expansion occurs. As a consequence, the grip separation ΔL increases with the temperature, particularly above the melting or softening point of the polymer sample. The test stops at the maximum temperature or when the gap between the fixtures reaches 65 mm.

Melt Index

Melt index, or $I_2$, is measured in accordance with ASTM D 1238, Condition 190° C./2.16 kg. Melt index, or $I_{10}$ is also measured in accordance with ASTM D 1238, Condition 190° C./10 kg.

Melt Flow Rate

Melt flow rate, or MFR, is measured in accordance with ASTM D 1238, Condition 230° C./2.16 kg.

ATREF

Analytical temperature rising elution fractionation (ATREF) analysis is conducted according to the method described in U.S. Pat. No. 4,798,081 and Wilde, L.; Ryle, T. R.; Knobeloch, D. C.; Peat, I. R.; *Determination of Branching Distributions in Polyethylene and Ethylene Copolymers*, J. Polym. Sci., 20, 441-455 (1982), which are incorporated by reference herein in their entirety. The composition to be analyzed is dissolved in trichlorobenzene and allowed to crystallize in a column containing an inert support (stainless steel shot) by slowly reducing the temperature to 20° C. at a cooling rate of 0.1° C./min. The column is equipped with an infrared detector. An ATREF chromatogram curve is then generated by eluting the crystallized polymer sample from the column by slowly increasing the temperature of the eluting solvent (trichlorobenzene) from 20 to 120° C. at a rate of 1.5° C./min.

$^{13}$C NMR Analysis

The samples are prepared by adding approximately 3 g of a 50/50 mixture of tetrachloroethane-$d^2$/orthodichlorobenzene to 0.4 g sample in a 10 mm NMR tube. The samples are dissolved and homogenized by heating the tube and its contents to 150° C. The data are collected using a JEOL Eclipse™ 400 MHz spectrometer or a Varian Unity Plus™ 400 MHz spectrometer, corresponding to a $^{13}$C resonance frequency of 100.5 MHz. The data are acquired using 4000 transients per data file with a 6 second pulse repetition delay. To achieve minimum signal-to-noise for quantitative analysis, multiple data files are added together. The spectral width is 25,000 Hz with a minimum file size of 32K data points. The samples are analyzed at 130° C. in a 10 mm broad band probe. The comonomer incorporation is determined using Randall's triad method (Randall, J. C.; JMS-Rev. Macromol. Chem. Phys., C29, 201-317 (1989), which is incorporated by reference herein in its entirety.

Polymer Fractionation by TREF

Large-scale TREF fractionation is carried by dissolving 15-20 g of polymer in 2 liters of 1,2,4-trichlorobenzene (TCB) by stirring for 4 hours at 160° C. The polymer solution is forced by 15 psig (100 kPa) nitrogen onto a 3 inch by 4 foot (7.6 cm×12 cm) steel column packed with a 60:40 (v:v) mix of 30-40 mesh (600-425 μm) spherical, technical quality glass beads (available from Potters Industries, HC 30 Box 20, Brownwood, Tex., 76801) and stainless steel, 0.028" (0.7 mm) diameter cut wire shot (available from Pellets, Inc. 63 Industrial Drive, North Tonawanda, N.Y., 14120). The column is immersed in a thermally controlled oil jacket, set initially to 160° C. The column is first cooled ballistically to 125° C., then slow cooled to 20° C. at 0.04° C. per minute and held for one hour. Fresh TCB is introduced at about 65 ml/min while the temperature is increased at 0.167° C. per minute.

Approximately 2000 ml portions of eluant from the preparative TREF column are collected in a 16 station, heated fraction collector. The polymer is concentrated in each fraction using a rotary evaporator until about 50 to 100 ml of the polymer solution remains. The concentrated solutions are allowed to stand overnight before adding excess methanol, filtering, and rinsing (approx. 300-500 ml of methanol including the final rinse). The filtration step is performed on a 3 position vacuum assisted filtering station using 5.0 μm polytetrafluoroethylene coated filter paper (available from Osmonics Inc., Cat #Z50WP04750). The filtrated fractions are dried overnight in a vacuum oven at 60° C. and weighed on an analytical balance before further testing.

Melt Strength

Melt Strength (MS) is measured by using a capillary rheometer fitted with a 2.1 mm diameter, 20:1 die with an entrance angle of approximately 45 degrees. After equilibrating the samples at 190° C. for 10 minutes, the piston is run at a speed of 1 inch/minute (2.54 cm/minute). The standard test temperature is 190° C. The sample is drawn uniaxially to a set of accelerating nips located 100 mm below the die with an acceleration of 2.4 mm/sec$^2$. The required tensile force is recorded as a function of the take-up speed of the nip rolls. The maximum tensile force attained during the test is defined as the melt strength. The melt strength is recorded in centiNewtons ("cN").

Water Vapor Transmission Rate (WVTR)/Breathability: A suitable technique for determining the WVTR (water vapor transmission rate) value of a film or laminate material of the invention is the test procedure standardized by INDA (Association of the Nonwoven Fabrics Industry), number IST-70.4-99, entitled "STANDARD TEST METHOD FOR WATER VAPOR TRANSMISSION RATE THROUGH NONWOVEN AND PLASTIC FILM USING A GUARD FILM AND VAPOR PRESSURE SENSOR" which is incorporated by reference herein. The INDA procedure provides for the determination of WVTR, the permeance of the film to water vapor and, for homogeneous materials, water vapor permeability coefficient.

The INDA test method is well known and will not be set forth in detail herein. However, the test procedure is summarized as follows. A dry chamber is separated from a wet chamber of known temperature and humidity by a permanent guard film and the sample material to be tested. The purpose of the guard film is to define a definite air gap and to quiet or still the air in the air gap while the air gap is characterized. The dry chamber, guard film, and the wet chamber make up a diffusion cell in which the test film is sealed. The sample holder is known as the Permatran-W Model 100K manufactured by Mocon, Inc., Minneapolis, Minn. A first test is made of the WVTR of the guard film and the air gap between an evaporator assembly that generates 100% relative humidity.

Water vapor diffuses through the air gap and the guard film and then mixes with a dry gas flow which is proportional to water vapor concentration. The electrical signal is routed to a computer for processing. The computer calculates the transmission rate of the air gap and the guard film and stores the value for further use.

The transmission rate of the guard film and air gap is stored in the computer as CalC. The sample material is then sealed in the test cell. Again, water vapor diffuses through the air gap to the guard film and the test material and then mixes with a dry gas flow that sweeps the test material. Also again, this mixture is carried to the vapor sensor. This information is used to calculate the transmission rate at which moisture is transmitted through the test material according to the equation:

$$TR^{-1}_{testmaterial} = TR^{-1}_{testmaterial,guardfilm,airgap} - TR^{-1}_{guardfilm,airgap}$$

Calculations:
WVTR: The calculation of the WVTR uses the formula:

$$WVTR = F p_{sat}(T) RH / (A p_{sat}(T)(1-RH))$$

where:
F=The flow of water vapor in cc/mint,
$p_{sat}(T)$=The density of water in saturated air at temperature T.
RH=The relative humidity at specified locations in the cell,
A=The cross sectional area of the cell, and,
$p_{sat}(T)$=The saturation vapor pressure of water vapor at temperature T.

For the purposes of this Application, the testing temperature for the above test was at about 37.8° C., the flow was at 100 cc/min, and the relative humidity was at 60%.

Additionally, the value for n was equal to 6 and the number of cycles was 3.

Cycle Testing: The materials is tested using a cyclical testing procedure to determine load loss and percent set. In particular 2 cycle testing is utilized to 70 percent defined elongation. For this test, the sample size is 3 inch in the MD by 6 inch in the CD. The grip size is 3 inch width. The grip separation is 4 inch. The samples are loaded such that the cross-direction of the sample is in the vertical direction. A preload of approximately 10-15 grams is set. The test pulls the sample at 20 inches/min (500 mm/min) to 70 percent elongation (2.8 inches in addition to the 4 inch gap), and then immediately (without pause) returns to the zero point (the 4 inch gauge separation). In-process testing (resulting in the data in this application) is done as a 2 cycle test. The results of the test data are all from the first and second cycles. The testing is done on a Sintech Corp. constant rate of extension tester 2/S with a Renew MTS mongoose box (controller) using TESTWORKS 4.07b software. (Sintech Corp, of Cary, N.C.). The tests are conducted under ambient conditions (20° C., 50% relative humidity).

Hydrostatic Pressure Test—The Hydrostatic Pressure Test is a measure of the liquid barrier properties of a material. In general, the Hydrostatic Pressure Test determines the height of water (in centimeters) in a column which the material will support before a predetermined amount of water passes through. A material with a higher hydrohead value indicates it is a greater barrier to liquid penetration than a material having a lower hydrohead value. The Hydrostatic Pressure Test is performed according to Method 5514—Federal Test Methods Standard No. 191A.

Preparation and Properties of Olefin Block Copolymers Catalysts

The term "overnight", if used, refers to a time of approximately 16-18 hours, the term "room temperature", refers to a temperature of 20-25° C., and the term "mixed alkanes" refers to a commercially obtained mixture of $C_{6-9}$ aliphatic hydrocarbons available under the trade designation Isopar E®, from ExxonMobil Chemical Company. In the event the name of a compound herein does not conform to the structural representation thereof, the structural representation shall control. The synthesis of all metal complexes and the preparation of all screening experiments were carried out in a dry nitrogen atmosphere using dry box techniques. All solvents used were HPLC grade and were dried before their use.

MMAO refers to modified methylalumoxane, a triisobutylaluminum modified methylalumoxane available commercially from Akzo-Nobel.

The preparation of catalyst (B1) is conducted as follows.

a) Preparation of (1-methylethyl)(2-hydroxy-3,5-di (t-butyl)phenyl)methylimine 3,5-Di-t-butylsalicylaldehyde (3.00 g) is added to 10 mL of isopropylamine. The solution rapidly turns bright yellow. After stirring at ambient temperature for 3 hours, volatiles are removed under vacuum to yield a bright yellow, crystalline solid (97 percent yield).

b) Preparation of 1,2-bis-(3,5-di-t-butylphenylene) (1-N-(1-methylethyl)immino)methyl)(2-oxoyl)zirconium dibenzyl A solution of (1-methylethyl)(2-hydroxy-3,5-di(t-butyl) phenyl)imine (605 mg, 2.2 mmol) in 5 mL toluene is slowly added to a solution of $Zr(CH_2Ph)_4$ (500 mg, 1.1 mmol) in 50 mL toluene. The resulting dark yellow solution is stirred for 30 min. Solvent is removed under reduced pressure to yield the desired product as a reddish-brown solid.

The preparation of catalyst (B2) is conducted as follows.

a) Preparation of (1-(2-methylcyclohexyl)ethyl)(2-oxoyl-3,5-di(t-butyl)phenyl)imine 2-Methylcyclohexylamine (8.44 mL, 64.0 mmol) is dissolved in methanol (90 mL), and di-t-butylsalicaldehyde (10.00 g, 42.67 mmol) is added. The reaction mixture is stirred for three hours and then cooled to −25° C. for 12 hrs. The resulting yellow solid precipitate is collected by filtration and washed with cold methanol (2×15 mL), and then dried under reduced pressure. The yield is 11.17 g of a yellow solid. $^1$H NMR is consistent with the desired product as a mixture of isomers.

b) Preparation of bis-(1-(2-methylcyclohexyl)ethyl) (2-oxoyl-3,5-di(t-butyl)phenyl) immino)zirconium dibenzyl A solution of (1-(2-methylcyclohexyl)ethyl)(2-oxoyl-3,5-di(t-butyl)phenyl)imine (7.63 g, 23.2 mmol) in 200 mL toluene is slowly added to a solution of $Zr(CH_2Ph)_4$ (5.28 g, 11.6 mmol) in 600 mL toluene. The resulting dark yellow solution is stirred for 1 hour at 25° C. The solution is diluted further with 680 mL toluene to give a solution having a concentration of 0.00783 M.

Cocatalyst 1 A mixture of methyldi($C_{14-18}$ alkyl)ammonium salts of tetrakis(pentafluorophenyl)borate (here-in-after armeenium borate), prepared by reaction of a long chain trialkylamine (Armeen™ M2HT, available from Akzo-Nobel), HCl and $Li[B(C_6F_5)_4]$, substantially as disclosed in U.S. Pat. No. 5,919,9883, Ex. 2.

Cocatalyst 2 Mixed $C_{14-18}$ alkyldimethylammonium salt of bis(tris(pentafluorophenyl)-alumane)-2-undecylimidazolide, prepared according to U.S. Pat. No. 6,395,671, Ex. 16.

Shuttling Agents The shuttling agents employed include diethylzinc (DEZ, SA1), di(i-butyl)zinc (SA2), di(n-hexyl)zinc (SA3), triethylaluminum (TEA, SA4), trioctylaluminum (SA5), triethylgallium (SA6), i-butylaluminum bis(dimethyl (t-butyl)siloxane) (SA7), i-butylaluminum bis(di(trimethylsilyl)amide) (SA8), n-octylaluminum di(pyridine-2-methoxide) (SA9), bis(n-octadecyl)i-butylaluminum (SA10), i-butylaluminum bis(di(n-pentyl)amide) (SA11), n-octylaluminum bis(2,6-di-t-butylphenoxide) (SA12), n-octylaluminum di(ethyl(1-naphthyl)amide) (SA13), ethylaluminum bis(t-butyldimethylsiloxide) (SA14), ethylaluminum di(bis (trimethylsilyl)amide) (SA15), ethylaluminum bis(2,3,6,7-dibenzo-1-azacycloheptaneamide) (SA16), n-octylaluminum bis(2,3,6,7-dibenzo-1-azacycloheptaneamide) (SA17), n-octylaluminum bis(dimethyl(t-butyl)siloxide) (SA18), ethylzinc (2,6-diphenylphenoxide) (SA19), and ethylzinc (t-butoxide) (SA20).

Examples 1-4

Comparative A-C

General High Throughput Parallel Polymerization Conditions

Polymerizations are conducted using a high throughput, parallel polymerization reactor (PPR) available from Symyx Technologies, Inc. and operated substantially according to U.S. Pat. Nos. 6,248,540, 6,030,917, 6,362,309, 6,306,658, and 6,316,663. Ethylene copolymerizations are conducted at 130° C. and 200 psi (1.4 MPa) with ethylene on demand using 1.2 equivalents of Cocatalyst 1 based on total catalyst used (1.1 equivalents when MMAO is present). A series of polymerizations are conducted in a parallel pressure reactor (PPR) contained of 48 individual reactor cells in a 6×8 array that are fitted with a pre-weighed glass tube. The working volume in each reactor cell is 6000 μL. Each cell is temperature and pressure controlled with stirring provided by individual stirring paddles. The monomer gas and quench gas are plumbed directly into the PPR unit and controlled by automatic valves. Liquid reagents are robotically added to each reactor cell by syringes and the reservoir solvent is mixed alkanes. The order of addition is mixed alkanes solvent (4 ml), ethylene, 1-octene comonomer (1 ml), Cocatalyst 1 or Cocatalyst 1/MMAO mixture, shuttling agent, and catalyst or catalyst mixture. When a mixture of Cocatalyst 1 and MMAO or a mixture of two catalysts is used, the reagents are premixed in a small vial immediately prior to addition to the reactor. When a reagent is omitted in an experiment, the above order of addition is otherwise maintained. Polymerizations are conducted for approximately 1-2 minutes, until predetermined ethylene consumptions are reached. After quenching with CO, the reactors are cooled and the glass tubes are unloaded. The tubes are transferred to a centrifuge/vacuum drying unit, and dried for 12 hours at 60° C. The tubes containing dried polymer are weighed and the difference between this weight and the tare weight gives the net yield of polymer. Results are contained in Table 1. In Table 1 and elsewhere in the application, comparative compounds are indicated by an asterisk (*).

Examples 1-4 demonstrate the synthesis of linear block copolymers by the present invention as evidenced by the formation of a very narrow MWD, essentially monomodal copolymer when DEZ is present and a bimodal, broad molecular weight distribution product (a mixture of separately produced polymers) in the absence of DEZ. Due to the fact that Catalyst (A1) is known to incorporate more octene than Catalyst (B1), the different blocks or segments of the resulting copolymers of the invention are distinguishable based on branching or density.

TABLE 1

| Ex. | Cat. (A1) (μmol) | Cat (B1) (μmol) | Cocat (μmol) | MMAO (μmol) | shuttling agent (μmol) | Yield (g) | Mn | Mw/Mn | hexyls[1] |
|---|---|---|---|---|---|---|---|---|---|
| A* | 0.06 | — | 0.066 | 0.3 | — | 0.1363 | 300502 | 3.32 | — |
| B* | — | 0.1 | 0.110 | 0.5 | — | 0.1581 | 36957 | 1.22 | 2.5 |
| C* | 0.06 | 0.1 | 0.176 | 0.8 | — | 0.2038 | 45526 | 5.30[2] | 5.5 |
| 1 | 0.06 | 0.1 | 0.192 | — | DEZ (8.0) | 0.1974 | 28715 | 1.19 | 4.8 |
| 2 | 0.06 | 0.1 | 0.192 | — | DEZ (80.0) | 0.1468 | 2161 | 1.12 | 14.4 |
| 3 | 0.06 | 0.1 | 0.192 | — | TEA (8.0) | 0.208 | 22675 | 1.71 | 4.6 |
| 4 | 0.06 | 0.1 | 0.192 | — | TEA (80.0) | 0.1879 | 3338 | 1.54 | 9.4 |

[1]$C_6$ or higher chain content per 1000 carbons
[2]Bimodal molecular weight distribution It may be seen that the olefin block copolymers produced according to the invention have a relatively narrow polydispersity (Mw/Mn) and larger block-copolymer content (trimer, tetramer, or larger) than polymers prepared in the absence of the shuttling agent.

Further characterizing data for the polymers of Table 1 are determined by reference to the Figures. More specifically DSC and ATREF results show the following:

The DSC curve for the polymer of Example 1 shows a 115.7° C. melting point (Tm) with a heat of fusion of 158.1 J/g. The corresponding CRYSTAF curve shows the tallest peak at 34.5° C. with a peak area of 52.9 percent. The difference between the DSC Tm and the Tcrystaf is 81.2° C.

The DSC curve for the polymer of Example 2 shows a peak with a 109.7° C. melting point (Tm) with a heat of fusion of 214.0 J/g. The corresponding CRYSTAF curve shows the tallest peak at 46.2° C. with a peak area of 57.0 percent. The difference between the DSC Tm and the Tcrystaf is 63.5° C.

The DSC curve for the polymer of Example 3 shows a peak with a 120.7° C. melting point (Tm) with a heat of fusion of 160.1 J/g. The corresponding CRYSTAF curve shows the tallest peak at 66.1° C. with a peak area of 71.8 percent. The difference between the DSC Tm and the Tcrystaf is 54.6° C.

The DSC curve for the polymer of Example 4 shows a peak with a 104.5° C. melting point (Tm) with a heat of fusion of 170.7 J/g. The corresponding CRYSTAF curve shows the tallest peak at 30° C. with a peak area of 18.2 percent. The difference between the DSC Tm and the Tcrystaf is 74.5° C.

The DSC curve for Comparative A shows a 90.0° C. melting point (Tm) with a heat of fusion of 86.7 J/g. The corresponding CRYSTAF curve shows the tallest peak at 48.5° C. with a peak area of 29.4 percent. Both of these values are consistent with a resin that is low in density. The difference between the DSC Tm and the Tcrystaf is 41.8° C.

The DSC curve for Comparative B shows a 129.8° C. melting point (Tm) with a heat of fusion of 237.0 J/g. The corresponding CRYSTAF curve shows the tallest peak at 82.4° C. with a peak area of 83.7 percent. Both of these values are consistent with a resin that is high in density. The difference between the DSC Tm and the Tcrystaf is 47.4° C.

The DSC curve for Comparative C shows a 125.3° C. melting point (Tm) with a heat of fusion of 143.0 J/g. The corresponding CRYSTAF curve shows the tallest peak at 81.8° C. with a peak area of 34.7 percent as well as a lower crystalline peak at 52.4° C. The separation between the two peaks is consistent with the presence of a high crystalline and a low crystalline polymer. The difference between the DSC Tm and the Tcrystaf is 43.5° C.

Examples 5-19

Comparatives D-F, Continuous Solution Polymerization, Catalyst A1/B2+DEZ

Continuous solution polymerizations are carried out in a computer controlled autoclave reactor equipped with an internal stirrer. Purified mixed alkanes solvent (Isopar™ E available from ExxonMobil Chemical Company), ethylene at 2.70 lbs/hour (1.22 kg/hour), 1-octene, and hydrogen (where used) are supplied to a 3.8 L reactor equipped with a jacket for temperature control and an internal thermocouple. The solvent feed to the reactor is measured by a mass-flow controller. A variable speed diaphragm pump controls the solvent flow rate and pressure to the reactor. At the discharge of the pump, a side stream is taken to provide flush flows for the catalyst and cocatalyst 1 injection lines and the reactor agitator. These flows are measured by Micro-Motion mass flow meters and controlled by control valves or by the manual adjustment of needle valves. The remaining solvent is combined with 1-octene, ethylene, and hydrogen (where used) and fed to the reactor. A mass flow controller is used to deliver hydrogen to the reactor as needed. The temperature of the solvent/monomer solution is controlled by use of a heat exchanger before entering the reactor. This stream enters the bottom of the reactor. The catalyst component solutions are metered using pumps and mass flow meters and are combined with the catalyst flush solvent and introduced into the bottom of the reactor. The reactor is run liquid-full at 500 psig (3.45 MPa) with vigorous stirring. Product is removed through exit lines at the top of the reactor. All exit lines from the reactor are steam traced and insulated. Polymerization is stopped by the addition of a small amount of water into the exit line along with any stabilizers or other additives and passing the mixture through a static mixer. The product stream is then heated by passing through a heat exchanger before devolatilization. The polymer product is recovered by extrusion using a devolatilizing extruder and water cooled pelletizer. Process details and results are contained in Table 2. Selected polymer properties are provided in Table 3.

TABLE 2

Process Details

| Ex. | $C_8H_{16}$ kg/hr | Solv. kg/hr | $H_2$ sccm[1] | T °C. | Cat Al[2] ppm | Cat A1 Flow kg/hr | Cat B2[3] ppm | B2 Flow kg/hr | DEZ Conc % | DEZ Flow kg/hr | Cocat Conc. ppm | Cocat Flow kg/hr | $[C_2H_4]/[DEZ]$[4] | Poly Rate[5] kg/hr | Conv %[6] | Solids % | Eff.[7] |
|---|---|---|---|---|---|---|---|---|---|---|---|---|---|---|---|---|---|
| D* | 1.63 | 12.7 | 29.90 | 120 | 142.2 | 0.14 | — | — | 0.19 | 0.32 | 820 | 0.17 | 536 | 1.81 | 88.8 | 11.2 | 95.2 |
| E* | " | 9.5 | 5.00 | " | — | — | 109 | 0.10 | 0.19 | " | 1743 | 0.40 | 485 | 1.47 | 89.9 | 11.3 | 126.8 |
| F* | " | 11.3 | 251.6 | " | 71.7 | 0.06 | 30.8 | 0.06 | — | — | " | 0.11 | — | 1.55 | 88.5 | 10.3 | 257.7 |
| 5 | " | " | — | " | " | 0.14 | 30.8 | 0.13 | 0.17 | 0.43 | " | 0.26 | 419 | 1.64 | 89.6 | 11.1 | 118.3 |
| 6 | " | " | 4.92 | " | " | 0.10 | 30.4 | 0.08 | 0.17 | 0.32 | " | 0.18 | 570 | 1.65 | 89.3 | 11.1 | 172.7 |
| 7 | " | " | 21.70 | " | " | 0.07 | 30.8 | 0.06 | 0.17 | 0.25 | " | 0.13 | 718 | 1.60 | 89.2 | 10.6 | 244.1 |
| 8 | " | " | 36.90 | " | " | 0.06 | " | " | " | 0.10 | " | 0.12 | 1778 | 1.62 | 90.0 | 10.8 | 261.1 |
| 9 | " | " | 78.43 | " | " | " | " | " | " | 0.04 | " | " | 4596 | 1.63 | 90.2 | 10.8 | 267.9 |
| 10 | " | " | 0.00 | 123 | 71.1 | 0.12 | 30.3 | 0.14 | 0.34 | 0.19 | 1743 | 0.08 | 415 | 1.67 | 90.31 | 11.1 | 131.1 |
| 11 | " | " | " | 120 | 71.1 | 0.16 | " | 0.17 | 0.80 | 0.15 | 1743 | 0.10 | 249 | 1.68 | 89.56 | 11.1 | 100.6 |
| 12 | " | " | " | 121 | 71.1 | 0.15 | " | 0.07 | " | 0.09 | 1743 | 0.07 | 396 | 1.70 | 90.02 | 11.3 | 137.0 |
| 13 | " | " | " | 122 | 71.1 | 0.12 | " | 0.06 | " | 0.05 | 1743 | 0.05 | 653 | 1.69 | 89.64 | 11.2 | 161.9 |
| 14 | " | " | " | 120 | 71.1 | 0.05 | " | 0.29 | " | 0.10 | 1743 | 0.10 | 395 | 1.41 | 89.42 | 9.3 | 114.1 |
| 15 | 2.45 | " | " | " | 71.1 | 0.14 | " | 0.17 | " | 0.14 | 1743 | 0.09 | 282 | 1.80 | 89.33 | 11.3 | 121.3 |
| 16 | " | " | " | 122 | 71.1 | 0.10 | " | 0.13 | " | 0.07 | 1743 | 0.07 | 485 | 1.78 | 90.11 | 11.2 | 159.7 |
| 17 | " | " | " | 121 | 71.1 | 0.10 | " | 0.14 | " | 0.08 | 1743 | " | 506 | 1.75 | 89.08 | 11.0 | 155.6 |
| 18 | 0.69 | " | " | 121 | 71.1 | " | " | 0.22 | " | 0.11 | 1743 | 0.10 | 331 | 1.25 | 89.93 | 8.8 | 90.2 |
| 19 | 0.32 | " | " | 122 | 71.1 | 0.06 | " | " | " | 0.09 | 1743 | 0.08 | 367 | 1.16 | 90.74 | 8.4 | 106.0 |

*Comparative, not an example of the invention
[1] standard cm³/min
[2] [N-(2,6-di(1-methylethyl)phenyl)amido)(2-isopropylphenyl)(α-naphthalen-2-diyl(6-pyridin-2-diyl)methane)]hafnium dimethyl
[3] bis-(1-(2-methylcyclohexyl)ethyl)(2-oxoyl-3,5-di(t-butyl)phenyl)immino) zirconium dibenzyl
[4] molar ratio in reactor
[5] polymer production rate
[6] percent ethylene conversion in reactor
[7] efficiency, kg polymer/g M where g M = g Hf + g Zr

TABLE 3

Physical Properties

| Ex. | Density (g/cm³) | $I_2$ | $I_{10}$ | $I_{10}/I_2$ | Mw (g/mol) | Mn (g/mol) | Mw/Mn | Heat of Fusion (J/g) | $T_m$ (° C.) | $T_c$ (° C.) | $T_{CRYSTAF}$ (° C.) | $Tm - T_{CRYSTAF}$ (° C.) | CRYSTAF Peak Area (percent) |
|---|---|---|---|---|---|---|---|---|---|---|---|---|---|
| D* | 0.8627 | 1.5 | 10.0 | 6.5 | 110,000 | 55,800 | 2.0 | 32 | 37 | 45 | 30 | 7 | 99 |
| E* | 0.9378 | 7.0 | 39.0 | 5.6 | 65,000 | 33,300 | 2.0 | 183 | 124 | 113 | 79 | 45 | 95 |
| F* | 0.8895 | 0.9 | 12.5 | 13.4 | 137,300 | 9,980 | 13.8 | 90 | 125 | 111 | 78 | 47 | 20 |
| 5 | 0.8786 | 1.5 | 9.8 | 6.7 | 104,600 | 53,200 | 2.0 | 55 | 120 | 101 | 48 | 72 | 60 |
| 6 | 0.8785 | 1.1 | 7.5 | 6.5 | 109600 | 53300 | 2.1 | 55 | 115 | 94 | 44 | 71 | 63 |
| 7 | 0.8825 | 1.0 | 7.2 | 7.1 | 118,500 | 53,100 | 2.2 | 69 | 121 | 103 | 49 | 72 | 29 |
| 8 | 0.8828 | 0.9 | 6.8 | 7.7 | 129,000 | 40,100 | 3.2 | 68 | 124 | 106 | 80 | 43 | 13 |
| 9 | 0.8836 | 1.1 | 9.7 | 9.1 | 129600 | 28700 | 4.5 | 74 | 125 | 109 | 81 | 44 | 16 |
| 10 | 0.8784 | 1.2 | 7.5 | 6.5 | 113,100 | 58,200 | 1.9 | 54 | 116 | 92 | 41 | 75 | 52 |
| 11 | 0.8818 | 9.1 | 59.2 | 6.5 | 66,200 | 36,500 | 1.8 | 63 | 114 | 93 | 40 | 74 | 25 |
| 12 | 0.8700 | 2.1 | 13.2 | 6.4 | 101,500 | 55,100 | 1.8 | 40 | 113 | 80 | 30 | 83 | 91 |
| 13 | 0.8718 | 0.7 | 4.4 | 6.5 | 132,100 | 63,600 | 2.1 | 42 | 114 | 80 | 30 | 81 | 8 |
| 14 | 0.9116 | 2.6 | 15.6 | 6.0 | 81,900 | 43,600 | 1.9 | 123 | 121 | 106 | 73 | 48 | 92 |
| 15 | 0.8719 | 6.0 | 41.6 | 6.9 | 79,900 | 40,100 | 2.0 | 33 | 114 | 91 | 32 | 82 | 10 |
| 16 | 0.8758 | 0.5 | 3.4 | 7.1 | 148,500 | 74,900 | 2.0 | 43 | 117 | 96 | 48 | 69 | 65 |
| 17 | 0.8757 | 1.7 | 11.3 | 6.8 | 107,500 | 54,000 | 2.0 | 43 | 116 | 96 | 43 | 73 | 57 |
| 18 | 0.9192 | 4.1 | 24.9 | 6.1 | 72,000 | 37,900 | 1.9 | 136 | 120 | 106 | 70 | 50 | 94 |
| 19 | 0.9344 | 3.4 | 20.3 | 6.0 | 76,800 | 39,400 | 1.9 | 169 | 125 | 112 | 80 | 45 | 88 |

The resulting polymers are tested by DSC and ATREF as with previous examples. Results are as follows:

The DSC curve for the polymer of Example 5 shows a peak with a 119.6° C. melting point (Tm) with a heat of fusion of 60.0 J/g. The corresponding CRYSTAF curve shows the tallest peak at 47.6° C. with a peak area of 59.5 percent. The delta between the DSC Tm and the Tcrystaf is 72.0° C.

The DSC curve for the polymer of Example 6 shows a peak with a 115.2° C. melting point (Tm) with a heat of fusion of 60.4 J/g. The corresponding CRYSTAF curve shows the tallest peak at 44.2° C. with a peak area of 62.7 percent. The delta between the DSC Tm and the Tcrystaf is 71.0° C.

The DSC curve for the polymer of Example 7 shows a peak with a 121.3° C. melting point with a heat of fusion of 69.1 J/g. The corresponding CRYSTAF curve shows the tallest peak at 49.2° C. with a peak area of 29.4 percent. The delta between the DSC Tm and the Tcrystaf is 72.1° C.

The DSC curve for the polymer of Example 8 shows a peak with a 123.5° C. melting point (Tm) with a heat of fusion of 67.9 J/g. The corresponding CRYSTAF curve shows the tallest peak at 80.1° C. with a peak area of 12.7 percent. The delta between the DSC Tm and the Tcrystaf is 43.4° C.

The DSC curve for the polymer of Example 9 shows a peak with a 124.6° C. melting point (Tm) with a heat of fusion of 73.5 J/g. The corresponding CRYSTAF curve shows the tallest peak at 80.8° C. with a peak area of 16.0 percent. The delta between the DSC Tm and the Tcrystaf is 43.8° C.

The DSC curve for the polymer of Example 10 shows a peak with a 115.6° C. melting point (Tm) with a heat of fusion of 60.7 J/g. The corresponding CRYSTAF curve shows the tallest peak at 40.9° C. with a peak area of 52.4 percent. The delta between the DSC Tm and the Tcrystaf is 74.7° C.

The DSC curve for the polymer of Example 11 shows a peak with a 113.6° C. melting point (Tm) with a heat of fusion of 70.4 J/g. The corresponding CRYSTAF curve shows the tallest peak at 39.6° C. with a peak area of 25.2 percent. The delta between the DSC Tm and the Tcrystaf is 74.1° C.

The DSC curve for the polymer of Example 12 shows a peak with a 113.2° C. melting point (Tm) with a heat of fusion of 48.9 J/g. The corresponding CRYSTAF curve shows no peak equal to or above 30° C. (Tcrystaf for purposes of further calculation is therefore set at 30° C.). The delta between the DSC Tm and the Tcrystaf is 83.2° C.

The DSC curve for the polymer of Example 13 shows a peak with a 114.4° C. melting point (Tm) with a heat of fusion of 49.4 J/g. The corresponding CRYSTAF curve shows the tallest peak at 33.8° C. with a peak area of 7.7 percent. The delta between the DSC Tm and the Tcrystaf is 84.4° C.

The DSC for the polymer of Example 14 shows a peak with a 120.8° C. melting point (Tm) with a heat of fusion of 127.9 J/g. The corresponding CRYSTAF curve shows the tallest peak at 72.9° C. with a peak area of 92.2 percent. The delta between the DSC Tm and the Tcrystaf is 47.9° C.

The DSC curve for the polymer of Example 15 shows a peak with a 114.3° C. melting point (Tm) with a heat of fusion of 36.2 J/g. The corresponding CRYSTAF curve shows the tallest peak at 32.3° C. with a peak area of 9.8 percent. The delta between the DSC Tm and the Tcrystaf is 82.0° C.

The DSC curve for the polymer of Example 16 shows a peak with a 116.6° C. melting point (Tm) with a heat of fusion of 44.9 J/g. The corresponding CRYSTAF curve shows the tallest peak at 48.0° C. with a peak area of 65.0 percent. The delta between the DSC Tm and the Tcrystaf is 68.6° C.

The DSC curve for the polymer of Example 17 shows a peak with a 116.0° C. melting point (Tm) with a heat of fusion of 47.0 J/g. The corresponding CRYSTAF curve shows the tallest peak at 43.1° C. with a peak area of 56.8 percent. The delta between the DSC Tm and the Tcrystaf is 72.9° C.

The DSC curve for the polymer of Example 18 shows a peak with a 120.5° C. melting point (Tm) with a heat of fusion of 141.8 J/g. The corresponding CRYSTAF curve shows the tallest peak at 70.0° C. with a peak area of 94.0 percent. The delta between the DSC Tm and the Tcrystaf is 50.5° C.

The DSC curve for the polymer of Example 19 shows a peak with a 124.8° C. melting point (Tm) with a heat of fusion of 174.8 J/g. The corresponding CRYSTAF curve shows the tallest peak at 79.9° C. with a peak area of 87.9 percent. The delta between the DSC Tm and the Tcrystaf is 45.0° C.

The DSC curve for the polymer of Comparative D shows a peak with a 37.3° C. melting point (Tm) with a heat of fusion of 31.6 J/g. The corresponding CRYSTAF curve shows no peak equal to and above 30° C. Both of these values are consistent with a resin that is low in density. The delta between the DSC Tm and the Tcrystaf is 7.3° C.

The DSC curve for the polymer of Comparative E shows a peak with a 124.0° C. melting point (Tm) with a heat of fusion of 179.3 J/g. The corresponding CRYSTAF curve shows the tallest peak at 79.3° C. with a peak area of 94.6 percent. Both of these values are consistent with a resin that is high in density. The delta between the DSC Tm and the Tcrystaf is 44.6° C.

The DSC curve for the polymer of Comparative F shows a peak with a 124.8° C. melting point (Tm) with a heat of fusion of 90.4 J/g. The corresponding CRYSTAF curve shows the tallest peak at 77.6° C. with a peak area of 19.5 percent. The separation between the two peaks is consistent with the presence of both a high crystalline and a low crystalline polymer. The delta between the DSC Tm and the Tcrystaf is 47.2° C.

Physical Property Testing

Polymer samples are evaluated for physical properties such as high temperature resistance properties, as evidenced by TMA temperature testing, pellet blocking strength, high temperature recovery, high temperature compression set and storage modulus ratio, G'(25° C.)/G'(100° C.). Several commercially available polymers are included in the tests: Comparative G* is a substantially linear ethylene/1-octene copolymer (AFFINITY®, available from The Dow Chemical Company), Comparative H* is an elastomeric, substantially linear ethylene/1-octene copolymer (AFFINITY®EG8100, available from The Dow Chemical Company), Comparative I is a substantially linear ethylene/1-octene copolymer (AFFINITY®PL1840, available from The Dow Chemical Company), Comparative J is a hydrogenated styrene/butadiene/styrene triblock copolymer (KRATON™ G1652, available from KRATON Polymers LLC), Comparative K is a thermoplastic vulcanizate (TPV, a polyolefin blend containing dispersed therein a crosslinked elastomer). Results are presented in Table 4.

C. or even greater than 100° C. This shows that the novel olefin block copolymers have better dimensional stability at higher temperatures compared to a physical blend of homopolymers of the comonomers. Comparative J (a commercial SEBS) has a good 1 mm TMA temperature of about 107° C., but it has very poor (high temperature 70° C.) compression set of about 100 percent and it also failed to recover (sample broke) during a high temperature (80° C.) 300 percent strain recovery. Thus, the exemplified olefin block copolymers have a unique combination of properties unavailable even in some commercially available, high performance thermoplastic elastomers.

Similarly, Table 4 shows a low (good) storage modulus ratio, G'(25° C.)/G'(100° C.), for the inventive olefin block copolymers of 6 or less, whereas a physical blend (Comparative F) has a storage modulus ratio of 9 and a random ethylene/octene copolymer (Comparative G) of similar density has a storage modulus ratio an order of magnitude greater (89). It is desirable that the storage modulus ratio of a polymer be as close to 1 as possible. Such polymers will be relatively unaffected by temperature, and fabricated articles made from such polymers can be usefully employed over a broad temperature range. This feature of low storage modulus ratio and temperature independence is particularly useful in elastomer applications such as in pressure sensitive adhesive formulations.

The data in Table 4 also demonstrate that the olefin block copolymers of the invention possess improved pellet blocking strength. In particular, Example 5 has a pellet blocking strength of 0 MPa, meaning it is free flowing under the conditions tested, compared to Comparatives F and G which show considerable blocking. Blocking strength is important since bulk shipment of polymers having large blocking

TABLE 4

High Temperature Mechanical Properties

| Ex. | TMA-1 mm penetration (° C.) | Pellet Blocking Strength lb/ft$^2$ (kPa) | G'(25° C.)/ G'(100° C.) | 300% Strain Recovery (80° C.) (percent) | Compression Set (70° C.) (percent) |
|---|---|---|---|---|---|
| D* | 51 | — | 9 | Failed | — |
| E* | 130 | — | 18 | — | — |
| F* | 70 | 141 (6.8) | 9 | Failed | 100 |
| 5 | 104 | 0 (0) | 6 | 81 | 49 |
| 6 | 110 | — | 5 | — | 52 |
| 7 | 113 | — | 4 | 84 | 43 |
| 8 | 111 | — | 4 | Failed | 41 |
| 9 | 97 | — | 4 | — | 66 |
| 10 | 108 | — | 5 | 81 | 55 |
| 11 | 100 | — | 8 | — | 68 |
| 12 | 88 | — | 8 | — | 79 |
| 13 | 95 | — | 6 | 84 | 71 |
| 14 | 125 | — | 7 | — | — |
| 15 | 96 | — | 5 | — | 58 |
| 16 | 113 | — | 4 | — | 42 |
| 17 | 108 | 0 (0) | 4 | 82 | 47 |
| 18 | 125 | — | 10 | — | — |
| 19 | 133 | — | 9 | — | — |
| G* | 75 | 463 (22.2) | 89 | Failed | 100 |
| H* | 70 | 213 (10.2) | 29 | Failed | 100 |
| I* | 111 | — | 11 | — | — |
| J* | 107 | — | 5 | Failed | 100 |
| K* | 152 | — | 3 | — | 40 |

In Table 4, Comparative F (which is a physical blend of the two polymers resulting from simultaneous polymerizations using catalyst A1 and B1) has a 1 mm penetration temperature of about 70° C., while Examples 5-9 have a 1 mm penetration temperature of 100° C. or greater. Further, examples 10-19 all have a 1 mm penetration temperature of greater than 85° C., with most having 1 mm TMA temperature of greater than 90° strengths can result in product clumping or sticking together upon storage or shipping, resulting in poor handling properties.

High temperature (70° C.) compression set for the inventive olefin block copolymers is generally good, meaning generally less than about 80 percent, preferably less than about 70 percent and especially less than about 60 percent. In contrast, Comparatives F, G, H and J all have a 70° C. compression set of 100 percent (the maximum possible value, indicating no recovery). Good high temperature compression set (low numerical values) is especially needed for applications such as gaskets, window profiles, o-rings, and the like.

compared to, for example, Comparative G. Lower stress relaxation means that the polymer retains its force better in applications such as diapers and other garments where retention of elastic properties over long time periods at body temperatures is desired.

TABLE 5

Ambient Temperature Mechanical Properties

| Ex. | Flex Modulus (MPa) | Tensile Modulus (MPa) | Tensile Strength (MPa)[1] | Elongation at Break[1] (%) | Tensile Strength (MPa) | Elongation at Break (%) | Abrasion: Volume Loss (mm³) | Tensile Notched Tear Strength (mJ) | 100% Strain Recovery 21° C. (percent) | 300% Strain Recovery 21° C. (percent) | Retractive Stress at 150% Strain (kPa) | Compression Set 21° C. (Percent) | Stress Relaxation at 50% Strain[2] |
|---|---|---|---|---|---|---|---|---|---|---|---|---|---|
| D* | 12 | 5 | — | — | 10 | 1074 | — | — | 91 | 83 | 760 | — | — |
| E* | 895 | 589 | — | — | 31 | 1029 | — | — | — | — | — | — | — |
| F* | 57 | 46 | — | — | 12 | 824 | 93 | 339 | 78 | 65 | 400 | 42 | — |
| 5 | 30 | 24 | 14 | 951 | 16 | 1116 | 48 | — | 87 | 74 | 790 | 14 | 33 |
| 6 | 33 | 29 | — | — | 14 | 938 | — | — | — | 75 | 861 | 13 | — |
| 7 | 44 | 37 | 15 | 846 | 14 | 854 | 39 | — | 82 | 73 | 810 | 20 | — |
| 8 | 41 | 35 | 13 | 785 | 14 | 810 | 45 | 461 | 82 | 74 | 760 | 22 | — |
| 9 | 43 | 38 | — | — | 12 | 823 | — | — | — | — | — | 25 | — |
| 10 | 23 | 23 | — | — | 14 | 902 | — | — | 86 | 75 | 860 | 12 | — |
| 11 | 30 | 26 | — | — | 16 | 1090 | — | 976 | 89 | 66 | 510 | 14 | 30 |
| 12 | 20 | 17 | 12 | 961 | 13 | 931 | — | 1247 | 91 | 75 | 700 | 17 | — |
| 13 | 16 | 14 | — | — | 13 | 814 | — | 691 | 91 | — | — | 21 | — |
| 14 | 212 | 160 | — | — | 29 | 857 | — | — | — | — | — | — | — |
| 15 | 18 | 14 | 12 | 1127 | 10 | 1573 | — | 2074 | 89 | 83 | 770 | 14 | — |
| 16 | 23 | 20 | — | — | 12 | 968 | — | — | 88 | 83 | 1040 | 13 | — |
| 17 | 20 | 18 | — | — | 13 | 1252 | — | 1274 | 13 | 83 | 920 | 4 | — |
| 18 | 323 | 239 | — | — | 30 | 808 | — | — | — | — | — | — | — |
| 19 | 706 | 483 | — | — | 36 | 871 | — | — | — | — | — | — | — |
| G* | 15 | 15 | — | — | 17 | 1000 | — | 746 | 86 | 53 | 110 | 27 | 50 |
| H* | 16 | 15 | — | — | 15 | 829 | — | 569 | 87 | 60 | 380 | 23 | — |
| I* | 210 | 147 | — | — | 29 | 697 | — | — | — | — | — | — | — |
| J* | — | — | — | — | 32 | 609 | — | — | 93 | 96 | 1900 | 25 | — |
| K* | — | — | — | — | — | — | — | — | — | — | — | 30 | — |

[1]Tested at 51 cm/minute
[2]measured at 38° C. for 12 hours

Table 5 shows results for mechanical properties for the new olefin block copolymers as well as for various comparison polymers at ambient temperatures. It may be seen that the inventive polymers have very good abrasion resistance when tested according to ISO 4649, generally showing a volume loss of less than about 90 mm³, preferably less than about 80 mm³, and especially less than about 50 mm³. In this test, higher numbers indicate higher volume loss and consequently lower abrasion resistance.

Tear strength as measured by tensile notched tear strength of the inventive polymers is generally 1000 mJ or higher, as shown in Table 5. Tear strength for the inventive polymers can be as high as 3000 mJ, or even as high as 5000 mJ. Comparative polymers generally have tear strengths no higher than 750 mJ.

Table 5 also shows that the polymers of the invention have better retractive stress at 150 percent strain (demonstrated by higher retractive stress values) than some of the comparative samples. Comparative Examples F, G and H have retractive stress value at 150 percent strain of 400 kPa or less, while the inventive polymers have retractive stress values at 150 percent strain of 500 kPa (Ex. 11) to as high as about 1100 kPa (Ex. 17). Polymers having higher than 150 percent retractive stress values would be quite useful for elastic applications, such as elastic fibers and fabrics, especially nonwoven fabrics. Other applications include diaper, hygiene, and medical garment waistband applications, such as tabs and elastic bands.

Table 5 also shows that stress relaxation (at 50 percent strain) is also improved (less) for the inventive polymers as Optical Testing

TABLE 6

Polymer Optical Properties

| Ex. | Internal Haze (percent) | Clarity (percent) | 45° Gloss (percent) |
|---|---|---|---|
| F* | 84 | 22 | 49 |
| G* | 5 | 73 | 56 |
| 5 | 13 | 72 | 60 |
| 6 | 33 | 69 | 53 |
| 7 | 28 | 57 | 59 |
| 8 | 20 | 65 | 62 |
| 9 | 61 | 38 | 49 |
| 10 | 15 | 73 | 67 |
| 11 | 13 | 69 | 67 |
| 12 | 8 | 75 | 72 |
| 13 | 7 | 74 | 69 |
| 14 | 59 | 15 | 62 |
| 15 | 11 | 74 | 66 |
| 16 | 39 | 70 | 65 |
| 17 | 29 | 73 | 66 |
| 18 | 61 | 22 | 60 |
| 19 | 74 | 11 | 52 |
| G* | 5 | 73 | 56 |
| H* | 12 | 76 | 59 |
| I* | 20 | 75 | 59 |

The optical properties reported in Table 6 are based on compression molded films substantially lacking in orientation. Optical properties of the polymers may be varied over wide ranges, due to variation in crystallite size, resulting from variation in the quantity of chain shuttling agent employed in the polymerization.

Extractions of Multi-Block Copolymers

Extraction studies of the polymers of Examples 5, 7 and Comparative E are conducted. In the experiments, the polymer sample is weighed into a glass fritted extraction thimble and fitted into a Kumagawa type extractor. The extractor with sample is purged with nitrogen, and a 500 mL round bottom flask is charged with 350 mL of diethyl ether. The flask is then fitted to the extractor. The ether is heated while being stirred. Time is noted when the ether begins to condense into the thimble, and the extraction is allowed to proceed under nitrogen for 24 hours. At this time, heating is stopped and the solution is allowed to cool. Any ether remaining in the extractor is returned to the flask. The ether in the flask is evaporated under vacuum at ambient temperature, and the resulting solids are purged dry with nitrogen. Any residue is transferred to a weighed bottle using successive washes of hexane. The combined hexane washes are then evaporated with another nitrogen purge, and the residue dried under vacuum overnight at 40° C. Any remaining ether in the extractor is purged dry with nitrogen.

A second clean round bottom flask charged with 350 mL of hexane is then connected to the extractor. The hexane is heated to reflux with stirring and maintained at reflux for 24 hours after hexane is first noticed condensing into the thimble. Heating is then stopped and the flask is allowed to cool. Any hexane remaining in the extractor is transferred back to the flask. The hexane is removed by evaporation under vacuum at ambient temperature, and any residue remaining in the flask is transferred to a weighed bottle using successive hexane washes. The hexane in the flask is evaporated by a nitrogen purge, and the residue is vacuum dried overnight at 40° C.

The polymer sample remaining in the thimble after the extractions is transferred from the thimble to a weighed bottle and vacuum dried overnight at 40° C. Results are contained in Table 7.

catalyst component solutions are metered using pumps and mass flow meters. The reactor is run liquid-full at approximately 550 psig pressure. Upon exiting the reactor, water and additive are injected in the polymer solution. The water hydrolyzes the catalysts, and terminates the polymerization reactions. The post reactor solution is then heated in preparation for a two-stage devolatization. The solvent and unreacted monomers are removed during the devolatization process. The polymer melt is pumped to a die for underwater pellet cutting.

For Example 19J

Continuous solution polymerizations are carried out in a computer controlled autoclave reactor equipped with an internal stirrer. Purified mixed alkanes solvent (Isopar™ E available from ExxonMobil Chemical Company), ethylene at 2.70 lbs/hour (1.22 kg/hour), 1-octene, and hydrogen (where used) are supplied to a 3.8 L reactor equipped with a jacket for temperature control and an internal thermocouple. The solvent feed to the reactor is measured by a mass-flow controller. A variable speed diaphragm pump controls the solvent flow rate and pressure to the reactor. At the discharge of the pump, a side stream is taken to provide flush flows for the catalyst and cocatalyst injection lines and the reactor agitator. These flows are measured by Micro-Motion mass flow meters and controlled by control valves or by the manual adjustment of needle valves. The remaining solvent is combined with 1-octene, ethylene, and hydrogen (where used) and fed to the reactor. A mass flow controller is used to deliver hydrogen to the reactor as needed. The temperature of the solvent/monomer solution is controlled by use of a heat exchanger before entering the reactor. This stream enters the bottom of the reactor. The catalyst component solutions are metered using pumps and mass flow meters and are combined with the catalyst flush solvent and introduced into the bottom of the reactor. The reactor is run liquid-full at 500 psig (3.45 MPa) with vigorous stirring. Product is removed through exit lines

TABLE 7

| Sample | wt. (g) | ether soluble (g) | ether soluble (percent) | $C_8$ mole percent[1] | hexane soluble (g) | hexane soluble (percent) | $C_8$ mole percent[1] | residue $C_8$ mole percent[1] |
|---|---|---|---|---|---|---|---|---|
| Comp. F* | 1.097 | 0.063 | 5.69 | 12.2 | 0.245 | 22.35 | 13.6 | 6.5 |
| Ex. 5 | 1.006 | 0.041 | 4.08 | — | 0.040 | 3.98 | 14.2 | 11.6 |
| Ex. 7 | 1.092 | 0.017 | 1.59 | 13.3 | 0.012 | 1.10 | 11.7 | 9.9 |

[1]Determined by $^{13}$C NMR

Additional Polymer Examples 19A-J

Continuous Solution Polymerization, Catalyst A1/B2+DEZ

For Examples 19A-I

Continuous solution polymerizations are carried out in a computer controlled well-mixed reactor. Purified mixed alkanes solvent (Isopar™ E available from Exxon Mobil Chemical Company) ethylene, 1-octene, and hydrogen (where used) are combined and fed to a 27 gallon reactor. The feeds to the reactor are measured by mass-flow controllers. The temperature of the feed stream is controlled by use of a glycol cooled heat exchanger before entering the reactor. The at the top of the reactor. All exit lines from the reactor are steam traced and insulated. Polymerization is stopped by the addition of a small amount of water into the exit line along with any stabilizers or other additives and passing the mixture through a static mixer. The product stream is then heated by passing through a heat exchanger before devolatilization. The polymer product is recovered by extrusion using a devolatilizing extruder and water cooled pelletizer.

Process details and results are contained in Table 8. Selected polymer properties are provided in Tables 9A-C.

In Table 9B, inventive examples 19F and 19G show low immediate set of around 65-70% strain after 500% elongation.

TABLE 8

| | | | | | | Polymerization Conditions | | | | | |
|---|---|---|---|---|---|---|---|---|---|---|---|
| Ex. | C₂H₄ lb/hr | C₈H₁₆ lb/hr | Solv. lb/hr | H₂ sccm[1] | T °C. | Cat A1[2] Conc. ppm | Cat A1 Flow lb/hr | Cat B2[3] Conc. ppm | Cat B2 Flow lb/hr | DEZ Conc wt % | DEZ Flow lb/hr |
| 19A | 55.29 | 32.03 | 323.03 | 101 | 120 | 600 | 0.25 | 200 | 0.42 | 3.0 | 0.70 |
| 19B | 53.95 | 28.96 | 325.3 | 577 | 120 | 600 | 0.25 | 200 | 0.55 | 3.0 | 0.24 |
| 19C | 55.53 | 30.97 | 324.37 | 550 | 120 | 600 | 0.216 | 200 | 0.609 | 3.0 | 0.69 |
| 19D | 54.83 | 30.58 | 326.33 | 60 | 120 | 600 | 0.22 | 200 | 0.63 | 3.0 | 1.39 |
| 19E | 54.95 | 31.73 | 326.75 | 251 | 120 | 600 | 0.21 | 200 | 0.61 | 3.0 | 1.04 |
| 19F | 50.43 | 34.80 | 330.33 | 124 | 120 | 600 | 0.20 | 200 | 0.60 | 3.0 | 0.74 |
| 19G | 50.25 | 33.08 | 325.61 | 188 | 120 | 600 | 0.19 | 200 | 0.59 | 3.0 | 0.54 |
| 19H | 50.15 | 34.87 | 318.17 | 58 | 120 | 600 | 0.21 | 200 | 0.66 | 3.0 | 0.70 |
| 19I | 55.02 | 34.02 | 323.59 | 53 | 120 | 600 | 0.44 | 200 | 0.74 | 3.0 | 1.72 |
| 19J | 7.46 | 9.04 | 50.6 | 47 | 120 | 150 | 0.22 | 76.7 | 0.36 | 0.5 | 0.19 |

| Ex. | Cocat 1 Conc. ppm | Cocat 1 Flow lb/hr | Cocat 2 Conc. ppm | Cocat 2 Flow lb/hr | Zn[4] in polymer ppm | Poly Rate[5] lb/hr | Conv[6] wt % | Polymer wt % | Eff.[7] |
|---|---|---|---|---|---|---|---|---|---|
| 19A | 4500 | 0.65 | 525 | 0.33 | 248 | 83.94 | 88.0 | 17.28 | 297 |
| 19B | 4500 | 0.63 | 525 | 0.11 | 90 | 80.72 | 88.1 | 17.2 | 295 |
| 19C | 4500 | 0.61 | 525 | 0.33 | 246 | 84.13 | 88.9 | 17.16 | 293 |
| 19D | 4500 | 0.66 | 525 | 0.66 | 491 | 82.56 | 88.1 | 17.07 | 280 |
| 19E | 4500 | 0.64 | 525 | 0.49 | 368 | 84.11 | 88.4 | 17.43 | 288 |
| 19F | 4500 | 0.52 | 525 | 0.35 | 257 | 85.31 | 87.5 | 17.09 | 319 |
| 19G | 4500 | 0.51 | 525 | 0.16 | 194 | 83.72 | 87.5 | 17.34 | 333 |
| 19H | 4500 | 0.52 | 525 | 0.70 | 259 | 83.21 | 88.0 | 17.46 | 312 |
| 19I | 4500 | 0.70 | 525 | 1.65 | 600 | 86.63 | 88.0 | 17.6 | 275 |
| 19J | — | — | — | — | — | — | — | — | — |

[1] standard cm³/min
[2] [N-(2,6-di(1-methylethyl)phenyl)amido)(2-isopropylphenyl)(α-naphthalen-2-diyl)(6-pyridin-2-diyl) methane)]hafnium dimethyl
[3] bis-(1-(2-methylcyclohexyl)ethyl)(2-oxoyl-3,5-di(t-butyl)phenyl)immino) zirconium dimethyl
[4] ppm in final product calculated by mass balance
[5] polymer production rate
[6] weight percent ethylene conversion in reactor
[7] efficiency, kg polymer/g M where g M = g Hf + g Z

TABLE 9A

Polymer Physical Properties

| Ex. | Density (g/cc) | I₂ | I₁₀ | I₁₀/I₂ | M_w (g/mol) | M_n (g/mol) | M_w/M_n | Heat of Fusion (J/g) | T_m (°C.) | T_c (°C.) | T_CRYSTAF (°C.) | T_m − T_CRYSTAF (°C.) | CRYSTAF Peak Area (wt %) |
|---|---|---|---|---|---|---|---|---|---|---|---|---|---|
| 19A | 0.8781 | 0.9 | 6.4 | 6.9 | 123700 | 61000 | 2.0 | 56 | 119 | 97 | 46 | 73 | 40 |
| 19B | 0.8749 | 0.9 | 7.3 | 7.8 | 133000 | 44300 | 3.0 | 52 | 122 | 100 | 30 | 92 | 76 |
| 19C | 0.8753 | 5.6 | 38.5 | 6.9 | 81700 | 37300 | 2.2 | 46 | 122 | 100 | 30 | 92 | 8 |
| 19D | 0.8770 | 4.7 | 31.5 | 6.7 | 80700 | 39700 | 2.0 | 52 | 119 | 97 | 48 | 72 | 5 |
| 19E | 0.8750 | 4.9 | 33.5 | 6.8 | 81800 | 41700 | 2.0 | 49 | 121 | 97 | 36 | 84 | 12 |
| 19F | 0.8652 | 1.1 | 7.5 | 6.8 | 124900 | 60700 | 2.1 | 27 | 119 | 88 | 30 | 89 | 89 |
| 19G | 0.8649 | 0.9 | 6.4 | 7.1 | 135000 | 64800 | 2.1 | 26 | 120 | 92 | 30 | 90 | 90 |
| 19H | 0.8654 | 1.0 | 7.0 | 7.1 | 131600 | 66900 | 2.0 | 26 | 118 | 88 | — | — | — |
| 19I | 0.8774 | 11.2 | 75.2 | 6.7 | 66400 | 33700 | 2.0 | 49 | 119 | 99 | 40 | 79 | 13 |
| 19J | 0.8995 | 5.6 | 39.4 | 7.0 | 75500 | 29900 | 2.5 | 101 | 122 | 106 | — | — | — |

TABLE 9B

Polymer Physical Properties of Compression Molded Film

| Example | Density (g/cm³) | Melt Index (g/10 min) | Immediate Set after 100% Strain (%) | Immediate Set after 300% Strain (%) | Immediate Set after 500% Strain (%) | Recovery after 100% (%) | Recovery after 300% (%) | Recovery after 500% (%) |
|---|---|---|---|---|---|---|---|---|
| 19A | 0.878 | 0.9 | 15 | 63 | 131 | 85 | 79 | 74 |
| 19B | 0.877 | 0.88 | 14 | 49 | 97 | 86 | 84 | 81 |
| 19F | 0.865 | 1 | — | — | 70 | — | 87 | 86 |
| 19G | 0.865 | 0.9 | — | — | 66 | — | — | 87 |
| 19H | 0.865 | 0.92 | — | 39 | — | — | 87 | — |

TABLE 9C

Average Block Index for Exemplary Polymers[1]

| Example | $Zn/C_2$[2] | Average BI |
|---|---|---|
| Polymer F | 0 | 0 |
| Polymer 8 | 0.56 | 0.59 |
| Polymer 19a | 1.3 | 0.62 |
| Polymer 5 | 2.4 | 0.52 |
| Polymer 19b | 0.56 | 0.54 |
| Polymer 19h | 3.15 | 0.59 |

[1]Additional information regarding the calculation of the block indices for various polymers is disclosed in U.S. patent application Ser. No. 11/376,835, entitled "Ethylene/α-Olefin Block Interpolymers", filed on Mar. 15, 2006, in the name of Colin L. P. Shan, Lonnie Hazlitt, et. al. and assigned to Dow Global Technologies Inc., the disclosure of which is incorporated by reference herein in its entirety.
[2]$Zn/C_2$ * 1000 = (Zn feed flow * Zn concentration/1000000/Mw of Zn)/(Total Ethylene feed flow * (1 − fractional ethylene conversion rate)/Mw of Ethylene) * 1000. Please note that "Zn" in "$Zn/C_2$ * 1000" refers to the amount of zinc in diethyl zinc ("DEZ") used in the polymerization process, and "C2" refers to the amount of ethylene used in the polymerization process.

Measurement of Weight Percent of Hard and Soft Segments

As discussed above, the block interpolymers comprise hard segments and soft segments. The soft segments can be present in a block interpolymer from about 1 weight percent to about 99 weight percent of the total weight of the block interpolymer, preferably from about 5 weight percent to about 95 weight percent, from about 10 weight percent to about 90 weight percent, from about 15 weight percent to about 85 weight percent, from about 20 weight percent to about 80 weight percent, from about 25 weight percent to about 75 weight percent, from about 30 weight percent to about 70 weight percent, from about 35 weight percent to about 65 weight percent, from about 40 weight percent to about 60 weight percent, or from about 45 weight percent to about 55 weight percent. Conversely, the hard segments can be present in a similar range as above. The soft segment weight percentage (and thus the hard segment weight percentage) can be measured by DSC or NMR.

Hard Segment Weight Fraction Measured by DSC

For a block polymer having hard segments and soft segments, the density of the overall block polymer, $\rho_{overall}$, satisfies the following relationship:

$$\frac{1}{\rho_{overall}} = \frac{x_{hard}}{\rho_{hard}} + \frac{x_{soft}}{\rho_{soft}}$$

where $\rho_{hard}$ and $\rho_{soft}$ are the theoretical density of the hard segments and soft segments, respectively. $x_{hard}$ and $x_{soft}$ are the weight fraction of the hard segments and soft segments, respectively and they add up to one. Assuming $\rho_{hard}$ is equal to the density of ethylene homopolymer, i.e., 0.96 g/cc, and transposing the above equation, one obtains the following equation for the weight fraction of hard segments:

$$x_{hard} = \frac{\frac{1}{\rho_{overall}} - \frac{1}{\rho_{soft}}}{-\frac{1}{\rho_{overall}} + \frac{1}{0.96 \text{ g/cc}}}$$

In the above equation, $\rho_{overall}$ can be measured from the block polymer. Therefore, if $\rho_{soft}$ is known, the hard segment weight fraction can be calculated accordingly. Generally, the soft segment density has a linear relationship with the soft segment melting temperature, which can be measured by DSC over a certain range:

$$\rho_{soft} = A*T_m + B$$

where A and B are constants, and $T_m$ is the soft segment melting temperature in degrees Celsius. A and B can be determined by running DSC on various copolymers with a known density to obtain a calibration curve. It is preferable to create a soft segment calibration curve that span the range of composition (both comonomer type and content) present in the block copolymer. In some embodiments, the calibration curve satisfies the following relationship:

$$\rho_{soft} = 0.00049*T_m + 0.84990$$

Therefore, the above equation can be used to calculate the soft segment density if $T_m$ in degrees Celsius is known.

For some block copolymers, there is an identifiable peak in DSC that is associated with the melting of the soft segments. In this case, it is relatively straightforward to determine $T_m$ for the soft segments. Once $T_m$ in degrees Celsius is determined from DSC, the soft segment density can be calculated and thus the hard segment weight fraction.

Figure 10:
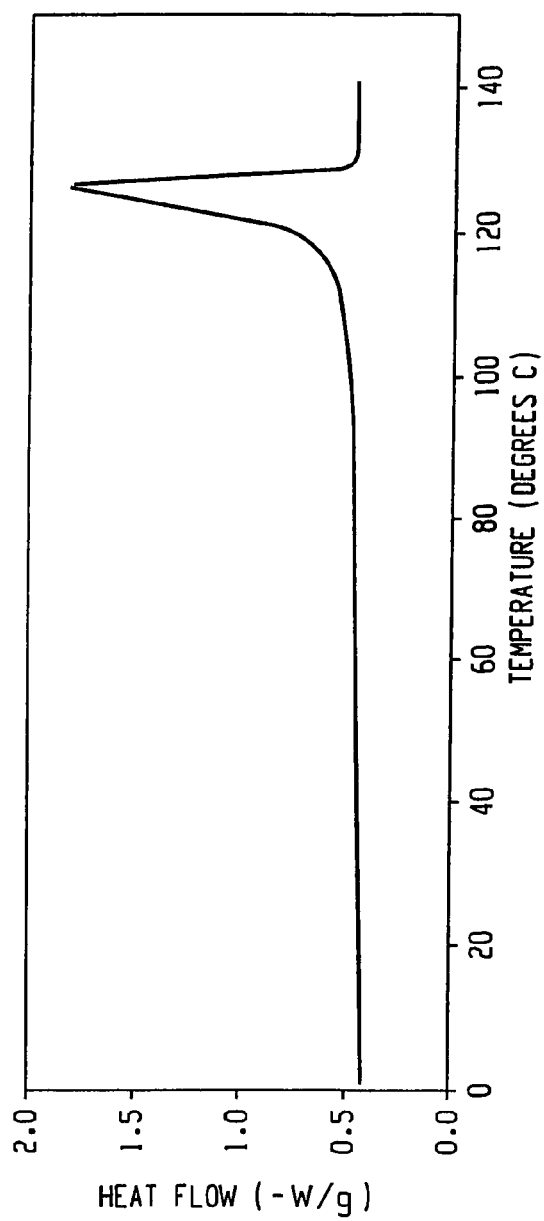
FIG. 10 is a representation of a normal DSC profile for an inventive polymer.
Figure 11:
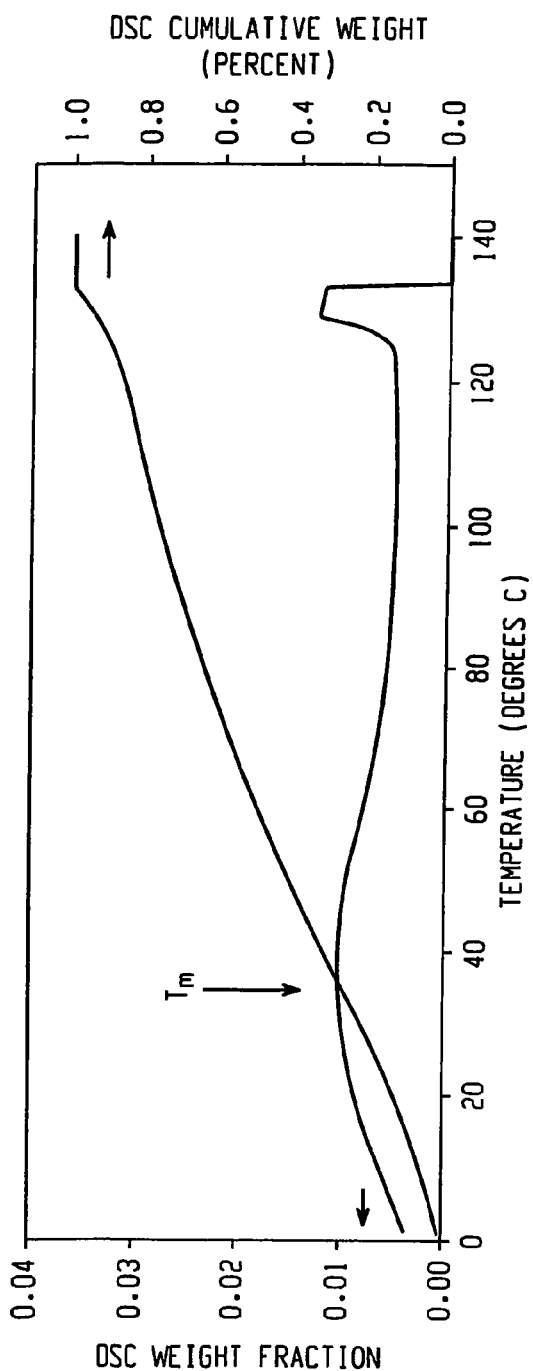
FIG. 11 is a weighted DSC profile obtained by converting FIG. 14.

For other block copolymers, the peak associated with the melting of the soft segments is either a small hump (or bump) over the baseline or sometimes not visible as illustrated in FIG. 10. This difficulty can be overcome by converting a normal DSC profile into a weighted DSC profile as shown in FIG. 11. The following method is used to convert a normal DSC profile to a weighted DSC profile.

In DSC, the heat flow depends on the amount of the material melting at a certain temperature as well as on the temperature-dependent specific heat capacity. The temperature-dependence of the specific heat capacity in the melting regime of linear low density polyethylene leads to an increase in the heat of fusion with decreasing comonomer content. That is, the heat of fusion values get progressively lower as the crystallinity is reduced with increasing comonomer content. See Wild, L. Chang, S.; Shankemarayanan, M J. "Improved method for compositional analysis of polyolefins by DSC." Polym. Prep 1990; 31: 270-1, which is incorporated by reference herein in its entirety.

For a given point in the DSC curve (defined by its heat flow in watts per gram and temperature in degrees Celsius), by taking the ratio of the heat of fusion expected for a linear copolymer to the temperature-dependent heat of fusion (ΔH (T)), the DSC curve can be converted into a weight-dependent distribution curve.

The temperature-dependent heat of fusion curve can be calculated from the summation of the integrated heat flow between two consecutive data points and then represented overall by the cumulative enthalpy curve.

The expected relationship between the heat of fusion for linear ethylene/octene copolymers at a given temperature is shown by the heat of fusion versus melting temperature curve. Using random ethylene/octene copolymers, one can obtain the following relationship:

Melt Enthalpy(J/g)=$0.0072*T_m^2$(° C.)+ $0.3138*T_m$(° C.)+8.9767

For each integrated data point, at a given temperature, by taking a ratio of the enthalpy from the cumulative enthalpy curve to the expected heat of fusion for linear copolymers at that temperature, fractional weights can be assigned to each point of the DSC curve.

It should be noted that, in the above method, the weighted DSC is calculated in the range from 0° C. until the end of melting. The method is applicable to ethylene/octene copolymers but can be adapted to other polymers.

Applying the above methodology to various polymers, the weight percentage of the hard segments and soft segments were calculated, which are listed in Table 10. It should be noted that sometimes it is desirable to assign 0.94 g/cc to the theoretical hard segment density, instead of using the density for homopolyethylene, due to the fact that the hard segments may include a small amount of comonomers.

TABLE 10

Calculated Weight Percentage of Hard and Soft Segments for Various Polymers

| Polymer Example No. | Overall Density | Soft Segment $T_m$ (° C.) from weighted DSC | Calculated Soft Segment Density | Calculated wt % Hard Segment | Calculated wt % Soft Segment |
|---|---|---|---|---|---|
| F* | 0.8895 | 20.3 | 0.860 | 32% | 68% |
| 5 | 0.8786 | 13.8 | 0.857 | 23% | 77% |
| 6 | 0.8785 | 13.5 | 0.857 | 23% | 77% |
| 7 | 0.8825 | 16.5 | 0.858 | 26% | 74% |
| 8 | 0.8828 | 17.3 | 0.858 | 26% | 74% |
| 9 | 0.8836 | 17.0 | 0.858 | 27% | 73% |
| 10 | 0.878 | 15.0 | 0.857 | 22% | 78% |
| 11 | 0.882 | 16.5 | 0.858 | 25% | 75% |
| 12 | 0.870 | 19.5 | 0.859 | 12% | 88% |
| 13 | 0.872 | 23.0 | 0.861 | 12% | 88% |
| 14 | 0.912 | 21.8 | 0.861 | 54% | 46% |
| 15 | 0.8719 | 0.5 | 0.850 | 22% | 78% |
| 16 | 0.8758 | 0.3 | 0.850 | 26% | 74% |
| 18 | 0.9192 | — | — | — | — |
| 19 | 0.9344 | 38.0 | 0.869 | 74% | 26% |
| 17 | 0.8757 | 2.8 | 0.851 | 25% | 75% |
| 19A | 0.8777 | 11.5 | 0.856 | 23% | 77% |
| 19B | 0.8772 | 14.3 | 0.857 | 22% | 78% |
| 19J | 0.8995 | 4.8 | 0.852 | 47% | 53% |

Hard Segment Weight Percentage Measured by NMR $^{13}$C NMR spectroscopy is one of a number of techniques known in the art for measuring comonomer incorporation into a polymer. An example of this technique is described for the determination of comonomer content for ethylene/α-olefin copolymers in Randall (Journal of Macromolecular Science, Reviews in Macromolecular Chemistry and Physics, C29(2 & 3), 201-317 (1989)), which is incorporated by reference herein in its entirety. The basic procedure for determining the comonomer content of an ethylene/olefin interpolymer involves obtaining a $^{13}$C NMR spectrum under conditions where the intensity of the peaks corresponding to the different carbons in a sample is directly proportional to the total number of contributing nuclei in the sample. Methods for ensuring this proportionality are known in the art and involve allowance for sufficient time for relaxation after a pulse, the use of gated-decoupling techniques, relaxation agents, and the like. The relative intensity of a peak or group of peaks is obtained in practice from its computer-generated integral. After obtaining the spectrum and integrating the peaks, those peaks associated with the comonomer are assigned. This assignment can be made by reference to known spectra or literature, or by synthesis and analysis of model compounds, or by the use of isotopically labeled comonomers. The mole % comonomer can be determined by the ratio of the integrals corresponding to the number of moles of comonomer to the integrals corresponding to the number of moles of all of the monomers in the interpolymer, as described in the aforementioned Randall reference.

Since the hard segment generally has less than about 2.0 wt % comonomer, its major contribution to the spectrum is only for the integral at about 30 ppm. The hard segment contribution to the peaks not at 30 ppm is assumed negligible at the start of the analysis. So for the starting point, the integrals of the peaks not at 30 ppm are assumed to come from the soft segment only. These integrals are fit to a first order Markovian statistical model for copolymers using a linear least squares minimization, thus generating fitting parameters (i.e., probability of octene insertion after octene, $P_{oo}$, and probability of octene insertion after ethylene, $P_{eo}$) that are used to compute the soft segment contribution to the 30 ppm peak. The difference between the total measured 30 ppm peak integral and the computed soft segment integral contribution to the 30 ppm peak is the contribution from the hard segment. Therefore, the experimental spectrum has now been deconvoluted into two integral lists describing the soft segment and hard segment, respectively. The calculation of weight percentage of the hard segment is straight forward and calculated by the ratio of the sum of integrals for the hard segment spectrum to the sum of integrals for the overall spectrum.

From the deconvoluted soft segment integral list, the comonomer composition can be calculated according to the method of Randall, for example. From the comonomer composition of the overall spectrum and the comonomer composition of the soft segment, one can use mass balance to compute the comonomer composition of the hard segment. From the comonomer composition of the hard segment, Bernoullian statistics is used to calculate the contribution of the hard segment to the integrals of non 30 ppm peaks. There is usually so little octene, typically from about 0 to about 1 mol %, in the hard segment that Bernoullian statistics is a valid and robust approximation. These contributions are then subtracted out from the experimental integrals of the non 30 ppm peaks. The resulting non 30 ppm peak integrals are then fitted to a first order Markovian statistics model for copolymers as described in the above paragraph. The iterative process is performed in the following manner: fit total non 30 ppm peaks then compute soft segment contribution to 30 ppm peak; then compute soft/hard segment split and then compute hard segment contribution to non 30 ppm peaks; then correct for hard segment contribution to non 30 ppm peaks and fit resulting non 30 ppm peaks. This is repeated until the values for soft/hard segment split converge to a minimum error function. The final comonomer compositions for each segment are reported.

Validation of the measurement is accomplished through the analysis of several in situ polymer blends. By design of the polymerization and catalyst concentrations the expected split is compared to the measured NMR split values. The soft/hard catalyst concentration is prescribed to be 74%/26%. The measured value of the soft/hard segment split is 78%/22%. Table 11 shows the chemical shift assignments for ethylene octene polymers.

TABLE 11

Chemical Shift Assignments for Ethylene/Octene Copolymers.

| | |
|---|---|
| 41-40.6 ppm | OOOE/EOOO αα CH2 |
| 40.5-40.0 ppm | EOOE αα CH2 |
| 38.9-37.9 ppm | EOE CH |
| 36.2-35.7 ppm | OOE center CH |
| 35.6-34.7 ppm | OEO αγ, OOO center 6B, OOEE αδ+, OOE center 6B CH2 |
| 34.7-34.1 ppm | EOE αγ+, EOE 6B CH2 |
| 33.9-33.5 ppm | OOO center CH |
| 32.5-32.1 ppm | 3B CH2 |
| 31.5-30.8 ppm | OEEO γγ CH2 |
| 30.8-30.3 ppm | OB γδ+ CH2 |
| 30.3-29.0 ppm | 4B, EEE δ+δ+ CH2 |
| 28.0-26.5 ppm | OE βδ+ 5B |
| 25.1-23.9 ppm | OEO ββ |
| 23.0-22.6 ppm | 2B |
| 14.5-14.0 ppm | 1B |

The following experimental procedures are used. A sample is prepared by adding 0.25 g in a 10 mm NMR tube with 2.5 mL of stock solvent. The stock solvent is made by dissolving 1 g perdeuterated 1,4-dichlorobenzene in 30 mL orthodichlorobenzene with 0.025 M chromium acetylacetonate (relaxation agent). The headspace of the tube is purged of oxygen by displacement with pure nitrogen. The sample tube is then heated in a heating block set at 150° C. The sample tube is repeatedly vortexed and heated until the solution flows consistently from top of the solution column to the bottom. The sample tube is then left in the heat block for at least 24 hours to achieve optimum sample homogeneity.

The $^{13}$C NMR data is collected using a Varian Inova Unity 400 MHz system with probe temperature set at 125° C. The center of the excitation bandwidth is set at 32.5 ppm with spectrum width set at 250 ppm. Acquisition parameters are optimized for quantitation including 90° pulse, inverse gated $^1$H decoupling, 1.3 second acquisition time, 6 seconds delay time, and 8192 scans for data averaging. The magnetic field is carefully shimmed to generate a line shape of less than 1 Hz at full width half maximum for the solvent peaks prior to data acquisition. The raw data file is processed using NUTS processing software (available from Acorn NMR, Inc. in Livermore, Calif.) and a list of integrals is generated.

Figure 12:
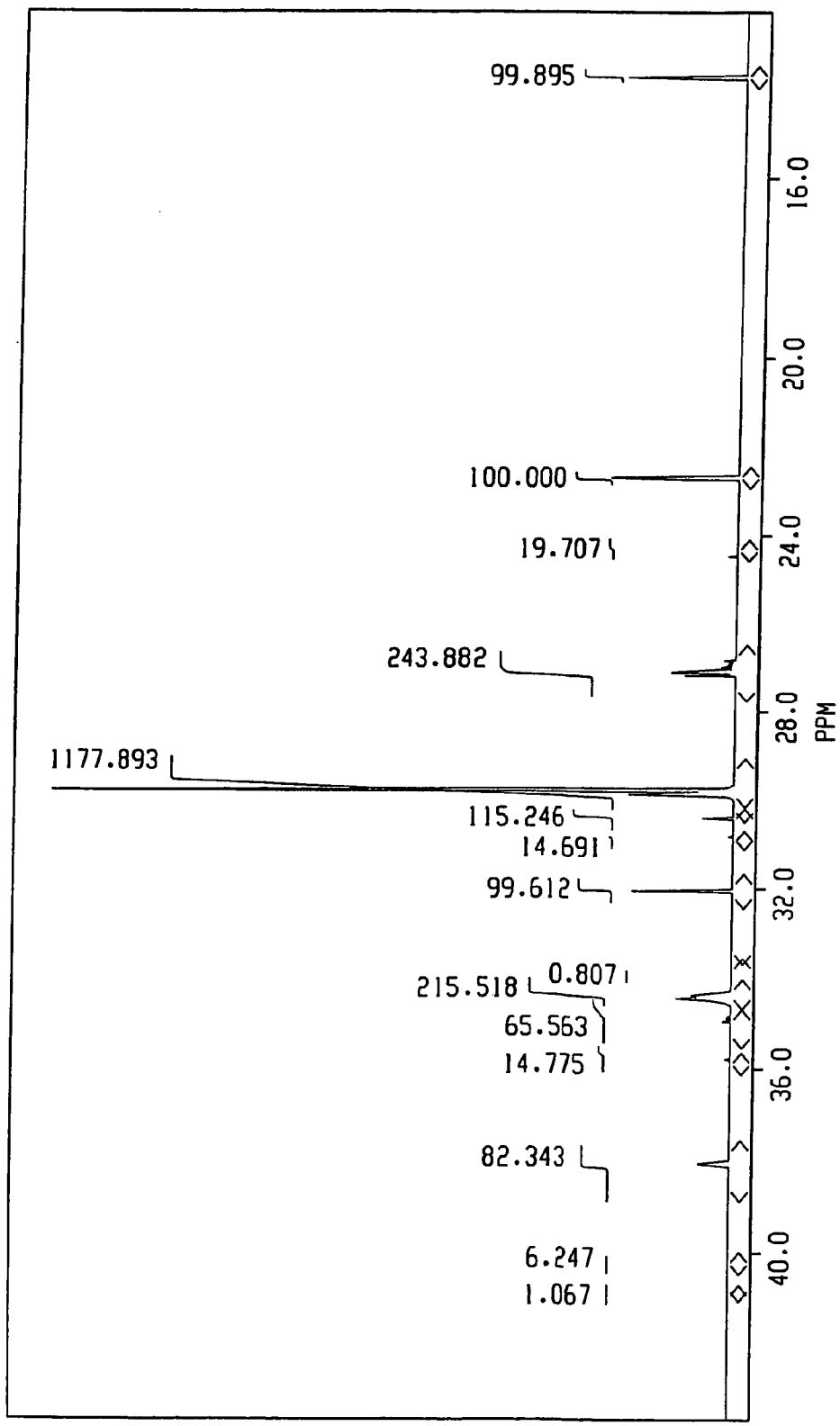
FIG. 12 is a $^{13}$C NMR spectrum of Polymer 19A.

Inventive Polymer 19A is analyzed for the soft/hard segment split and soft/hard comonomer composition. The following is the list of integrals for this polymer. The NMR spectrum for Polymer 19A is shown in FIG. 12.

| Integral limit | Integral value |
|---|---|
| 41.0-40.6 ppm | 1.067 |
| 40.5-40.0 ppm | 6.247 |
| 38.9-37.9 ppm | 82.343 |
| 36.2-35.7 ppm | 14.775 |
| 35.6-34.7 ppm | 65.563 |
| 34.7-34.1 ppm | 215.518 |
| 33.9-33.5 ppm | 0.807 |
| 32.5-32.1 ppm | 99.612 |
| 31.5-30.8 ppm | 14.691 |
| 30.8-30.3 ppm | 115.246 |
| 30.3-29.0 ppm | 1177.893 |

-continued

| Integral limit | Integral value |
|---|---|
| 28.0-26.5 ppm | 258.294 |
| 25.1-23.9 ppm | 19.707 |
| 23.0-22.6 ppm | 100 |
| 14.5-14.0 ppm | 99.895 |

Using Randall's triad method, the total octene weight percentage in this sample is determined to be 34.6%. Using all the above integrals excluding the 30.3-29.0 ppm integral to fit a first order Markovian statistical model, the values for Poo and Peo are determined to be 0.08389 and 0.2051, respectively. Using these two parameters, the calculated integral contribution from the soft segment to the 30 ppm peak is 602.586. Subtraction of 602.586 from the observed total integral for the 30 ppm peak, 1177.893, yields the contribution of the hard segment to the 30 ppm peak of 576.307. Using 576.307 as the integral for the hard segment, the weight percentage of hard segment is determined to be 26%. Therefore the soft segment weight percentage is 100-26=74%. Using the above values for $P_{oo}$ and $P_{eo}$, the octene weight percentage of the soft segment is determined to be 47%. Using the overall octene weight percentage and the octene weight percentage of the soft segment as well as the soft segment weight percentage, the octene weight percentage in the hard segment is calculated to be negative 2 wt %. This value is within the error of the measurement. Thus there is no need to iterate back to account for hard-segment contribution to non 30 ppm peaks. Table 12 summarizes the calculation results for Polymers 19A, B, F and G.

TABLE 12

Hard and Soft Segments Data for Polymers 19A, B, F and G

| Example | wt % Soft Segment | wt % Hard Segment | wt % octene in Soft Segment |
|---|---|---|---|
| 19A | 74 | 26 | 47 |
| 19B | 74 | 26 | 48 |
| 19F | 86 | 14 | 49 |
| 19G | 84 | 16 | 49 |

Comparative Examples L-P

Comparative Example L was a f-PVC, i.e., flexible poly (vinyl chloride), (obtained from Wofoo Plastics, Hong Kong, China). Comparative Example M was a SBS copolymer, VECTOR™ 7400 (obtained from Dexco Polymers, Houston, Tex.). Comparative Example N was a partially crosslinked TPV, VYRAM™ TPV 9271-65 (obtained from Advanced Elastomer Systems, Akron, Ohio). Comparative Example O was a SEBS copolymer, KRATON® G2705 (obtained from KRATON Polymers LLC, Houston, Tex.). Comparative Example P was a SBS copolymer, KRATON® G3202 (obtained from KRATON Polymers LLC, Houston, Tex.).

Examples 20-26

Example 20 was 100% of Example 19f. Example 21 was similar to Example 20, except that 30% of Example 19f was replaced with a high density polyethylene (HDPE), DMDA-8007 (from The Dow Chemical Company, Midland, Mich.). Example 22 was similar to Example 20, except that 20% of Example 19f was replaced with DMDA-8007. Example 23 was similar to Example 20, except that 10% of Example 19f was replaced with DMDA-8007. Example 24 was similar to Example 20, except that 30% of Example 19f was replaced with a homopolymer polypropylene, H700-12 (from The Dow Chemical Company, Midland, Mich.). Example 25 was similar to Example 20, except that 20% of Example 19f was replaced with H700-12. Example 26 was similar to Example 20, except that 10% of Example 19f was replaced with H700-12.

Comparative Examples Q-X

Comparative Example Q was similar to Example 21, except that Example 19f was replaced with a polyolefin elastomer, ENGAGE® ENR 7380 (from DuPont Dow Elastomers, Wilmington, Del.). Comparative Example R was similar to Example 24, except that Example 19f was replaced with ENGAGE® ENR 7380. Comparative Example S was similar to Example 20, except that Example 19f was replaced with a polyolefin elastomer, ENGAGE® 8407 (from DuPont Dow Elastomers, Wilmington, Del.) and the sample is 30 mil (0.762 mm) thick. Comparative Example T was similar to Example 20, except that Example 19f was replaced with a polyolefin elastomer, ENGAGE® 8967 (from DuPont Dow Elastomers, Wilmington, Del.). Comparative Example U was similar to Example 24, except that Example 19f was replaced with a propylene-ethylene copolymers, VERSIFY® DE3300 (from The Dow Chemical Company, Midland, Mich.). Comparative Example V was similar to Example 24, except that Example 19f was replaced with a propylene-ethylene copolymer, VERSIFY® DE3400 (from The Dow Chemical Company, Midland, Mich.). Comparative Example W was similar to Example 22, except that Example 19f was replaced with VERSIFY® DE3300. Comparative Example X was similar to Example 322 except that Example 19f was replaced with VERSIFY® DE3400.

Examples 27-33

Example 27 was a mixture of 56% of Example 19f, 16% of H700-12, and 28% of RENOIL® 625 (an oil from Renkert Oil Elversony, Pa.). Example 28 was similar to Example 27, except that the mixture was 33% of Example 19f, 17% of H700-12, and 50% of RENOIL® 625. Example 29 was similar to Example 27, except that the mixture was 56% of Example 19f, 16% of DMDA-8007, and 28% of RENOIL® 625. Example 30 was similar to Example 27, except that the mixture was 33% of Example 19f, 17% of DMDA-8007, and 50% of RENOIL® 625. Example 31 was similar to Example 27, except that the mixture was 17% of Example 19f, 16% of H700-12, 16% of KRATON® G2705 and 50% of RENOIL® 625. Example 32 was similar to Example 20, except that 1% of AMPACET® 10090 (an Erucamide concentrate from Ampacet Corporation, Tarrytown, N.Y.), was added as the slip/anti-blocking agent. Example 33 was similar to Example 32, except that 5% of AMPACET® 10090 was added as the slip/anti-blocking agent.

Mechanical and Physical Properties Measurements

The Thermomechanical (TMA) properties, hardness, compression set properties, flexural modulus, gull wing tear strength, Vicat softening point, blocking property, scratch mar resistance, ultimate elongation, 100% modulus, 300% modulus, ultimate tensile strength, and yield strength of Comparative Examples L-X and Examples 20-33 were measured and the results are shown in Tables 13 and 14 below.

The penetration temperature by thermal mechanical analysis (TMA) technique was conducted on 30 mm diameter×3.3 mm thick, compression molded discs, formed at 180° C. and 10 MPa molding pressure for 5 minutes and then air quenched. The instrument used was a Perkin-Elmer TMA 7. In the TMA test, a probe with 1.5 mm radius tip (P/N N519-0416) was applied to the surface of the sample disc with 1N force. The temperature was raised at 5° C./minute from 25° C. The probe penetration distance was measured as a function of temperature. The experiment ended when the probe had penetrated 0.1 mm and 1 mm respectively into the sample. The 0.1 mm and 1 mm penetration temperatures of each example are listed in Table 13 below.

The Shore D hardness of each sample was measured according to ASTM D 2240, which is incorporated herein by reference.

The compression set properties of each sample at 23° C. and 70° C. were measured according to ASTM D 4703, which is incorporated herein by reference.

The flexural modulus of each sample was measured according to the method described in ASTM D 790, which is incorporated herein by reference.

The gull wing tear strength of each sample was measured according to the method described in ASTM D 1004, which is incorporated herein by reference.

The Vicat softening point of each sample was measured according to the method described in ASTM D1525, which is incorporated herein by reference.

The blocking of each sample was measured by stacking six each 4"×4'×0.125" injection molded plaques, leaving the plaques at ambient conditions (73 F) for 24 hours, then un-stacking the plaques. The blocking rating is between 1 and 5 with 5 being excellent (all the plaques easily un-stacked) to 1 being unacceptable (where the 6 plaques had adhered to each other so much that none of the plaques could be separated by hand).

The scratch mar resistance of each sample was measured by manually scribing an X on a 4×4×0.125 inch plaque from corner to corner with a rounded plastic stylus. The scratch mar resistance rating is between 1 and 5 with 5 is excellent (where no evidence of the X is visible) and 1 is unacceptable (where the X is highly visible and can not be rubbed off).

The 100% modulus, 300% modulus, ultimate tensile strength, ultimate elongation, and yield strength of each sample were measured according to ASTM D 412, which is incorporated herein by reference.

TABLE 13

| Sample | 0.1 mm TMA (° C.) | 1.0 mm TMA (° C.) | Shore D | Compression Set at 70° C. | Compression Set at 23° C. | Flexural Modulus (psi) | Tear Strength (lbs/in) | Vicat Softening Point (° C.) | Blocking | Scratch Mar Resistance |
|---|---|---|---|---|---|---|---|---|---|---|
| Comp. Ex. L | 49 | 129 | 53 | 67 | 49 | 26654 | 391 | 69 | 5 | 4 |
| Comp. Ex. M | 25 | 78 | 10 | 91 | 17 | 1525 | / | 58 | 5 | 4 |
| Comp. Ex. N | 60 | 146 | 15 | 51 | 30 | 4613 | 149 | 65 | 4 | 4 |
| Comp. Ex. O | 71 | 137 | / | 40 | 21 | 2781 | 169 | / | 3 | 1 |

TABLE 13-continued

| Sample | 0.1 mm TMA (° C.) | 1.0 mm TMA (° C.) | Shore D | Compression Set at 70° C. | Compression Set at 23° C. | Flexural Modulus (psi) | Tear Strength (lbs/in) | Vicat Softening Point (° C.) | Blocking | Scratch Mar Resistance |
|---|---|---|---|---|---|---|---|---|---|---|
| Comp. Ex. P | 53 | 71 | / | 106 | 15 | 2043 | 149 | / | 1 | 1 |
| Example 20 | 67 | 99 | 17 | 57 | 21 | 4256 | 206 | 44 | 1 | 1 |
| Example 21 | 94 | 111 | 34 | 55 | 43 | 22071 | 441 | 66 | 1 | 1 |
| Example 22 | 98 | 113 | 33 | 56 | 31 | 14261 | 323 | 59 | 1 | 1 |
| Example 23 | 74 | 103 | 25 | 52 | 28 | 6943 | 254 | 50 | 1 | 1 |
| Example 24 | 99 | 111 | 36 | 66 | 37 | 24667 | 421 | 67 | 1 | 1 |
| Example 25 | 84 | 104 | 30 | 61 | 29 | 12325 | 331 | 55 | 1 | 1 |
| Example 26 | 81 | 104 | 24 | 61 | 23 | / | 257 | 47 | 1 | 1 |
| Comp. Ex. Q | 101 | 119 | 41 | 63 | 10 | 21358 | 426 | 59 | 1 | 1 |
| Comp. Ex. R | 101 | 146 | 41 | 97 | 27 | 20267 | / | 58 | 3 | 3 |
| Comp. Ex. S | 35 | 52 | 16 | 112 | 35 | 2116 | 186 | / | 1 | 1 |
| Comp. Ex. T | 48 | 95 | 22 | 83 | 37 | 6475 | 234 | / | 2 | 1 |
| Comp. Ex. U | 116 | 142 | 40 | / | / | / | / | / | 3 | 4 |
| Comp. Ex. V | 53 | 113 | 33 | / | / | 21348 | / | / | 1 | 3 |
| Comp. Ex. W | 68 | 95 | 33 | 76 | 44 | 11497 | 328 | / | 2 | 3 |
| Comp. Ex. X | 40 | 64 | 25 | 87 | 40 | 11384 | 281 | / | 1 | 1 |
| Example 27 | 76 | 105 | 18 | 48 | 28 | / | 252 | / | 2 | 1 |
| Example 28 | 49 | 95 | 13 | 57 | 27 | / | 177 | / | 2 | 2 |
| Example 29 | 63 | 106 | 18 | 42 | 30 | / | 215 | 47 | 2 | 1 |
| Example 30 | 54 | 99 | 10 | / | / | / | / | 48 | 2 | 2 |
| Example 31 | 48 | 99 | 12 | 55 | 41 | / | / | 57 | 3 | 2 |
| Example 32 | 69 | 99 | 20 | 54 | 21 | / | / | 44 | 5 | 4 |
| Example 33 | 74 | 99 | 19 | 52 | 19 | / | / | 44 | 5 | 5 |

TABLE 14

| Sample | 100% Modulus (psi) | 300% Modulus (psi) | Ultimate Tensile Strength (psi) | Ultimate Elongation (%) | Yield Strength (psi) |
|---|---|---|---|---|---|
| Comp. Ex. L | 1934 | 0 | 2522 | 224 | 607 |
| Comp. Ex. M | 198 | 140 | 549 | 505 | 45 |
| Comp. Ex. N | 336 | 175 | 604 | 459 | 122 |
| Comp. Ex. O | 213 | 118 | 1038 | 656 | 82 |
| Comp. Ex. P | 613 | 0 | 563 | 97 | 253 |
| Example 20 | 333 | 130 | 672 | 1039 | 162 |
| Example 21 | 795 | 258 | 1430 | 1007 | 652 |
| Example 22 | 589 | 198 | 1062 | 1026 | 443 |

Comparative Examples L, M, N, O and P are commercial flexible molded goods resins which are not olefin-based. Examples 20-26 are various embodiments of the olefin block copolymer (as a base resin or as a blend of the base resin with PP and/or HDPE) demonstrating the improved balance of low modulus and high upper service temperature. Comparative Examples Q-X are commercial flexible molded good resins that are olefin-based. Examples 20-26 demonstrate the improved balance of low modulus and high upper service temperature over Comparative Examples Q-X.

SEBS/Inventive Interpolymer Blends

Blends of ethylene/α-olefin block copolymer and hydrogenated styrenics block copolymer (OBC/SEBS) were prepared using a Haake Rheomix 300 rheometer. The temperature of the sample bowl was set at 190° C. and the rotor speed was 40 rpm. After all the components were added, the mixing was continued for about five minutes or until a stable torque has been established. Samples for further testing and evaluation were compression molded a Garver automatic press at 190° C. under 44.45 kN force for 3 minutes. The molten materials were subsequently quenched with the press equilibrated at room temperature using an electronic cooling bath.

Comparative Examples Y1-Y5

Comparative Example Y1 was 100% of KRATON® G1652, a styrene-ethylene/butylenes-styrene block copolymer available from KRATON Polymers LLC, Houston, Tex. Comparative Example Y1 was the same as Comparative Example J*. Comparative Example Y2 was a blend of 75% of KRATON® G1652 and 25% of AFFINITY® EG8100. Comparative Example Y3 was a blend of 50% of KRATON® G1652 and 50% of AFFINITY® EG8100. Comparative Example Y4 was a blend of 25% of KRATON® G1652 and 75% of AFFINITY® EG8100. Comparative Example Y5 was 100% AFFINITY® EG8100. Comparative Example Y5 was the same as Comparative Example H*.

Examples 34-45

Example 34 was a blend of 75% of KRATON® G1652 and 25% of Example or Polymer 19a. Example 35 was a blend of 50% of KRATON® G1652 and 50% of Example 19a. Example 36 was a blend of 25% of KRATON® G1652 and 75% of Example 19a. Example 37 was the same as Example 19a. Example 38 was a blend of 75% of KRATON® G1652 and 25% of Example 19b. Example 39 was a blend of 50% of KRATON® G 1652 and 50% of Example 19b. Example 40 was a blend of 25% of KRATON® G 1652 and 75% of Example 19b. Example 41 was the same as Example 19b. Example 42 was a blend of 75% of KRATON® G1652 and 25% of Polymer 19i. Polymer 19i was an interpolymer prepared substantially similarly to Examples 1-19 and Example 19a-19h. One skilled in the art would know how to manipulate process conditions, such as shuttling agent ratios, hydrogen flow, monomer concentration, etc., to make a target polymer using the process conditions already detailed in the instant application. Example 43 was a blend of 50% of KRATON® G1652 and 50% of Polymer 19i. Example 44 was a blend of 25% of KRATON® G1652 and 75% of Polymer 19i. Example 45 was 100% of Polymer 19i.

Mechanical and Physical Properties Measurement

The thermomechanical (TMA) properties, elastic recovery at 300% strain, elongation at break, tensile strength and Elmendorf tear strength of comparative examples Y1-Y5 and Examples 34-45 were measured by methods described herein and known to one of skill in the art and the results are shown in Table 15 below.

TABLE 15

Compositions and properties of SEBS blends of Examples 34-45 and Comparative Examples Y1-Y5.

| | Component B content, % | Component B[2] | TMA Temperature (° C.)[1] | Elastic Recovery @300% strain | Elongation @ Break (%) | Tensile Strength (MPa) | Elmendorf tear (g/mil) |
|---|---|---|---|---|---|---|---|
| Comparative Example Y1 | 0 | AFFINITY ® EG8100[3] | 97 | 92 | 589.8 | 21.2 | 70.2 |
| Comparative Example Y2 | 25 | AFFINITY ® EG8100 | 86 | 90 | 675.8 | 23.82 | 81.04 |
| Comparative Example Y3 | 50 | AFFINITY ® EG8100 | 71 | 82 | 664.3 | 17.08 | 47.57 |
| Comparative Example Y4 | 75 | AFFINITY ® EG8100 | 63.3 | 73 | 746.5 | 17.44 | 43.16 |
| Comparative Example Y5 | 100 | AFFINITY ® EG8100 | 60.2 | 61.7 | 777.4 | 13.52 | 55.6 |
| Example 34 | 25 | 19a[4] | 100 | 92 | 742.4 | 28.46 | 50.71 |
| Example 35 | 50 | 19a | 103 | 89 | 763.3 | 18.75 | 51.02 |
| Example 36 | 75 | 19a | 106 | 83.7 | 827.9 | 17.77 | 56.89 |
| Example 37 | 100 | 19a | 107.2 | 78.3 | 986.4 | 13.63 | 204.3 |
| Example 38 | 25 | 19b[5] | 99.5 | 92.7 | 693.6 | 24.45 | 41.27 |
| Example 39 | 50 | 19b | 101 | 90 | 770.8 | 21.1 | 36.05 |
| Example 40 | 75 | 19b | 104.9 | 86 | 813.1 | 18.18 | 34.7 |
| Example 41 | 100 | 19b | 106 | 80 | 931.5 | 13.93 | 67.76 |
| Example 42 | 25 | 19i[6] | 100 | 93.3 | 672 | 22.13 | 47.11 |
| Example 43 | 50 | 19i | 102.5 | 91 | 704.1 | 15.62 | 34.76 |
| Example 44 | 75 | 19i | 103.7 | 88 | 1059 | 18.42 | 20.85 |
| Example 45 | 100 | 19i | 108 | 80.2 | 1518 | 13.3 | 39.5 |

Notes:
[1]TMA temperature was measured at 1 mm penetration with a heating rate of 5° C./min under 1N force.
[2]The rest is Component A which is KRATON ® G1652, a SEBS available from KRATON Polymers LLC.
[3]AFFINITY ® EG8100 is a substantially linear ethylene/1-octene copolymer having $I_2$ of 1 g/10 min. (ASTM D-1238) and density of 0.870 g/cc (ASTM D-792).
[4]19a is an inventive ethylene/octene copolymer having $I_2$ of 1 g/10 min. and density of 0.878 g/cc.
[5]19b is an inventive ethylene/octene copolymer having $I_2$ of 1 g/10 min. and density of 0.875 g/cc.
[6]19i is an inventive ethylene/butene copolymer having $I_2$ of 1 g/10 min. and density of 0.876 g/cc.

Figure 13:
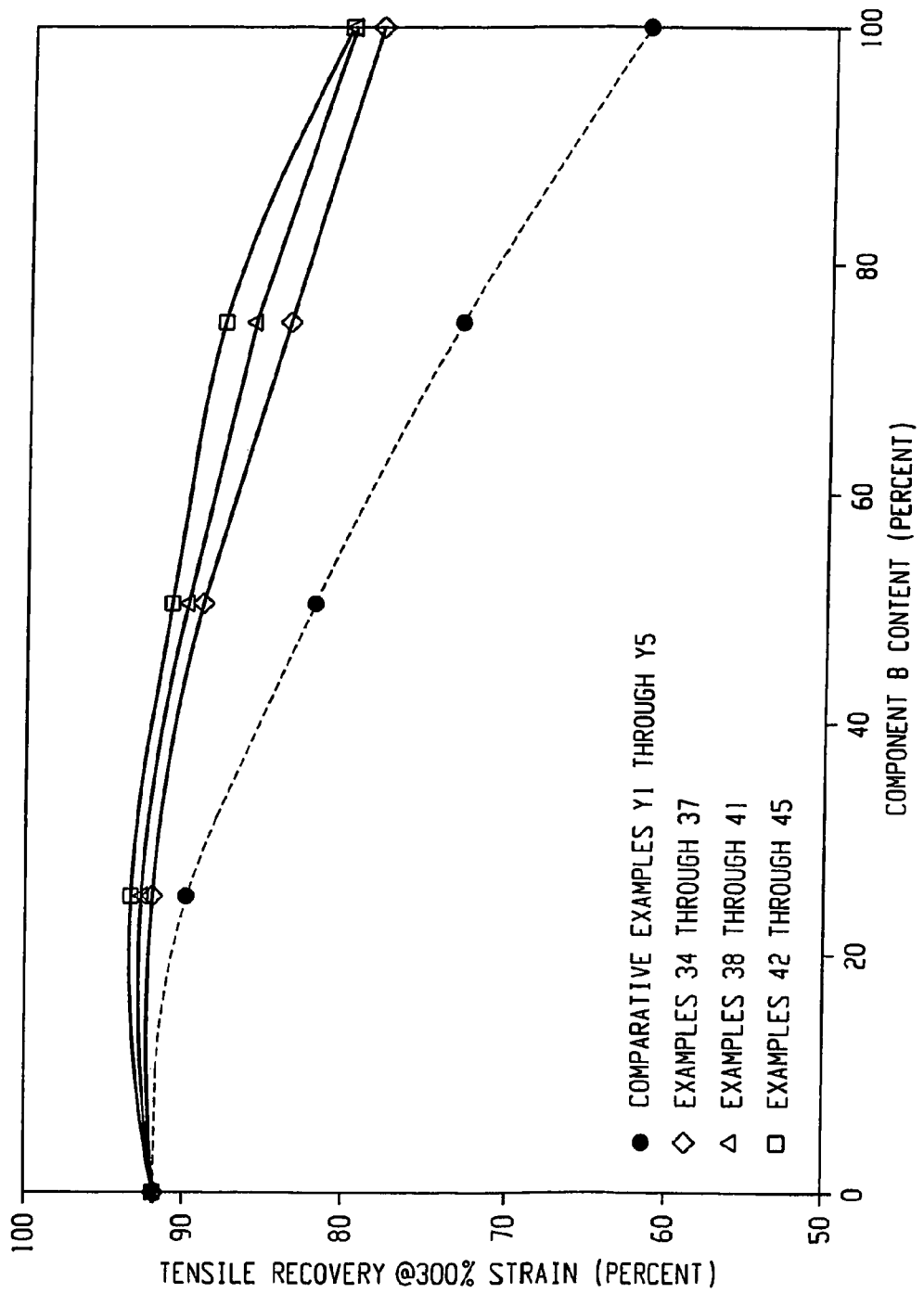
FIG. 13 shows tensile recovery of two-component blends containing Component A (i.e., KRATON® G1652, a SEBS) and Component B (i.e., AFFINITY® EG8100 or inventive Polymer 19a, 19b or 19i). The cycles represent blends containing KRATON® G1652 and AFFINITY® EG8100 (i.e., Comparative Examples Y1-Y5 having respectively 0%, 25%, 50%, 75% and 100% of AFFINITY® EG8100). The diamonds represent blends containing KRATON® G1652 and inventive Polymer 19a (i.e., Examples 34-37 having respectively 25%, 50%, 75% and 100% of Polymer 19a). The triangles represent the blends containing KRATON® G1652 and inventive Polymer 19b (i.e., Examples 38-41 having respectively 25%, 50%, 75% and 100% of Polymer 19b). The squares represent blends containing KRATON® G1652 and inventive Polymer 19i (i.e., Examples 42-45 having respectively 25%, 50%, 75% and 100% of Polymer 19i).
Figure 14:
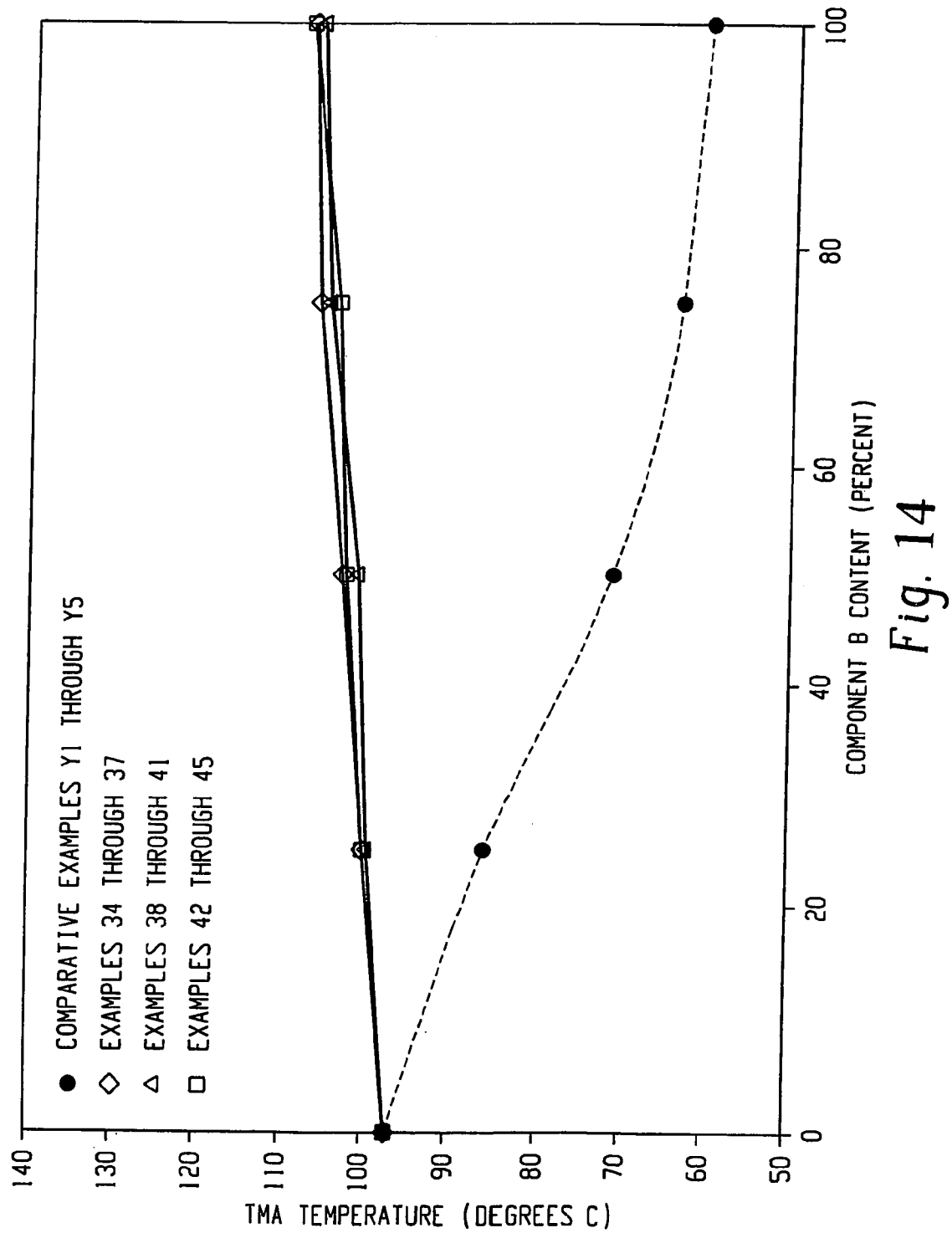
FIG. 14 shows heat resistance properties (i.e., TMA temperatures) of two-component blends containing Component A (i.e., KRATON® G1652, a SEBS) and Component B (i.e., AFFINITY® EG8100 or inventive Polymer 19a, 19b or 19i). The cycles represent blends containing KRATON® G61652 and AFFINITY® EG8100 (i.e., Comparative Examples Y1-Y5 having respectively 0%, 25%, 50%, 75% and 100% of AFFINITY®EG8100). The diamonds represent blends containing KRATON® G1652 and inventive Polymer 19a (i.e., Examples 34-37 having respectively 25%, 50%, 75% and 100% of Polymer 19a). The triangles represent the blends containing KRATON® G1652 and inventive Polymer 19b (i.e., Examples 38-41 having respectively 25%, 50%, 75% and 100% of Polymer 19b). The squares represent blends containing KRATON® G1652 and inventive Polymer 19i (i.e., Examples 42-45 having respectively 25%, 50%, 75% and 100% of Polymer 19i).

Elastic recovery properties of exemplary blends (i.e., Examples 34-45) and Comparative Examples Y1-Y5 at various amounts of SEBS (i.e., KRATON® G1652) in the blend are shown in FIG. 13. The TMA temperatures of exemplary blends and Comparative Examples Y1-Y5 at various amounts of SEBS in the blend are shown in FIG. 14. As seen in Table 15 and FIGS. 13-14, the exemplary blends (i.e., Examples 34-45) exhibit improved heat resistance and elastic recovery properties over the corresponding Comparative Examples Y1-Y5.

Additional Examples

Examples 46-49

Examples 46-49 were prepared in a similar fashion as Examples 19A-J above. Table 16 gives the polymerization conditions for the preparation of these examples, Table 17 gives physical property information for these polymers and Table 18 gives hard and soft segment data for these polymers.

TABLE 16

Polymerization Conditions

| Ex. | $C_8H_{16}$ kg/hr | Solv. kg/hr | $H_2$ sccm[1] | T ° C. | Cat Al[2] ppm | Cat Al Flow kg/hr | Cat B2[3] ppm | B2 Flow kg/hr | DEZ Conc % | DEZ Flow kg/hr | Cocat Conc. ppm | Cocat Flow kg/hr | [$C_2H_4$]/[DEZ][4] | Poly Rate[5] kg/hr | Conv 6% | Solids % | Eff.[7] |
|---|---|---|---|---|---|---|---|---|---|---|---|---|---|---|---|---|---|
| 46 | 107 | 1105 | 900 | 120 | 575 | 2.07 | 100 | 0.93 | 5 | 1.14 | 5700 | 1.88 | 730 | 234 | 88% | 17.5 | 182 |
| 47 | 81.8 | 343.9 | 2131 | 120 | 358.97 | 0.94 | 298.9 | 0.18 | 4.99 | 0.49 | 5751.6 | 0.62 | 1.96 | 84.5 | 91% | 17.6 | 214.9 |
| 48 | 105 | 1107 | 897 | 120 | 575 | 1.7 | 100 | 0.67 | 5 | 0.81 | 5700 | 1.52 | 1312 | 238 | 88% | 18 | 228 |
| 49 | 117 | 1091 | 1734 | 120 | 568 | 1.45 | 100 | 1.02 | 5 | 1.15 | 5535 | 1.46 | 1047 | 247 | 88% | 18.4 | 266 |

[1]standard cm³/min
[2][N-(2,6-di(1-methylethyl)phenyl)amido)(2-isopropylphenyl)(α-naphthalen-2-diyl(6-pyridin-2-diyl)methane)]hafnium dimethyl
[3]bis-(1-(2-methylcyclohexyl)ethyl)(2-oxoyl-3,5-di(t-butyl)phenyl)immino) zirconium dimethyl
[4]ppm in final product calculated by mass balance
[5]polymer production rate
[6]weight percent ethylene conversion in reactor
[7]efficiency, kg polymer/g M where g M = g Hf + g Z

TABLE 17

Polymer Physical Properties

| Ex. | Density (g/cm³) | $I_2$ | $I_{10}$ | $I_{10}/I_2$ | Mw (g/mol) | Mn (g/mol) | Mw/Mn | Heat of Fusion (J/g) | $T_m$ (° C.) | $T_c$ (° C.) | $T_{CRYSTAF}$ (° C.) | $T_m - T_{CRYSTAF}$ (° C.) | CRYSTAF Peak Area (percent) |
|---|---|---|---|---|---|---|---|---|---|---|---|---|---|
| 46 | 0.866 | 5.2 | 36.3 | 7 | 89500 | 45300 | 2.0 | 25 | 119 | 97 | n/a | n/a | n/a |
| 47 | 0.867 | 10.1 | 71.1 | 7 | 71200 | 32200 | 2.2 | 33 | 117 | 98 | n/a | n/a | n/a |

TABLE 17-continued

Polymer Physical Properties

| Ex. | Density (g/cm³) | $I_2$ | $I_{10}$ | $I_{10}/I_2$ | Mw (g/mol) | Mn (g/mol) | Mw/Mn | Heat of Fusion (J/g) | $T_m$ (°C.) | $T_c$ (°C.) | $T_{CRYSTAF}$ (°C.) | $T_m - T_{CRYSTAF}$ (°C.) | CRYSTAF Peak Area (percent) |
|---|---|---|---|---|---|---|---|---|---|---|---|---|---|
| 48 | 0.866 | 0.9 | 0.0 | 7.3 | 134900 | 63300 | 2.1 | 22 | 119 | 98 | n/a | n/a | n/a |
| 49 | 0.873 | 10.1 | 0.0 | 7.6 | 78000 | 39100 | 2.0 | 35.59 | 119.4 | 102.2 | n/a | n/a | n/a | n/a: denotes not available.

TABLE 18

Hard and Soft Segment Data for Polymers 46-49

| Example | wt % Soft Segment | wt % Hard Segment | wt % octene in Soft Segment |
|---|---|---|---|
| 46 | 0.855 | 15 | 85 |
| 47 | 0.855 | 15 | 85 |
| 48 | 0.855 | 15 | 85 |
| 49 | 0.853 | 30 | 70 |

TABLE 19

Styrenic Block Copolymers

| Parameter | Units | Test Method | G1657 linear SEBS triblock | G1652 linear SEBS triblock |
|---|---|---|---|---|
| Polystyrene content | weight % | BAM 919 | 12.3-14.3 | 29.0-30.8 |
| Solution viscosity [a] | cps | BAM 922 | 1,200-1,800 | 400-525 |
| Styrene/Rubber ratio | % | | 13/87 | 30/70 |
| Diblock content | % | | 30 | <1 |
| Melt index | gms/10 min | 230° C., 5 kg | 22 | 5 |
| Specific gravity | g/cm3 | | 0.89 | 0.91 |
| Shore A (10s) [b] | | | 47 | 69 |
| Tensile strength | MPa | [c] | 900 | 600 |
| Elongation | % | [c] | 13.9 | 22 |
| 2% Secant Modulus | MPa | [c] | 3.9 | 19 |
| Permanent Set | % | [d] | 22 | 16 |

[a] 20% w toluene solution at 25° C.
[b] Typical values on polymer compression molded at about 150° C. (300° F.)
[c] Tensile Test at Ambient Conditions (see description in this document)
[d] 300% Hysteresis Test at Ambient Conditions (see description in this document)

Examples 50-109

Tables 19 and 20 give physical information on the styrenic block copolymers used in Examples 50-109, which are examples of blend compositions of the present invention. Compositions and tensile properties of these blends are given in Table 21.

TABLE 20

Additional Styrenic Block Copolymers

| Parameter | Units | Test Method | VECTOR 4111 linear SIS triblock | VECTOR 4211 linear SIS triblock |
|---|---|---|---|---|
| Styrene | weight % | | 18 | 30 |
| Diblock Content | weight % | | <1.0 | <1.0 |
| MFR (1) | g/10 min | ASTMD-1238 | 12 | 13 |
| Specific Gravity | g/cm3 | ASTM D-792 | 0.93 | 0.94 |
| Tensile Strength | MPa | (2.3) | 16.0 | 22.0 |
| Elongation | % | (2.3) | 1300 | 1174 |
| 2% Secant Modulus | MPa | (2.3) | 1.6 | 4.6 |
| Permanent Set | % | (2.4) | 9 | 8 |

(1) Condition G (200° C., 5 kg)
(2) Typical values on compression molded plaques
(3) Tensile Test at Ambient Conditions (see description in this document)
(4) 300% Hysteresis Test at Ambient Conditions (see description in this document)

TABLE 21

Blends and Tensile Measurements of Inventive Compositions

| Example | Blend Component 1 | Blend Component 2 | Blend Component 1/ Blend Component 2 | 2% Sec Mod (MPa) (i) | Elongation at Break (%) (i) | Tensile Strength (MPa) (i) | Set after 300% Hysteresis (%) (ii) |
|---|---|---|---|---|---|---|---|
| 50 | A1[a] | 47 | 25/75 | 3.9 | 2100 | 5.5 | 0 |
| 51 | A1[a] | 47 | 50/50 | 3.3 | 1700 | 3.2 | 34 |
| 52 | A1[a] | 47 | 75/25 | 1.8 | 1000 | 1.8 | 35 |
| 53 | A1[a] | 46 | 25/75 | 3.3 | 2300 | 4.6 | 39 |
| 54 | A1[a] | 46 | 50/50 | 1.4 | 1700 | 2.4 | 37 |
| 55 | A1[a] | 46 | 75/25 | 1.5 | 1100 | 1.8 | 34 |

TABLE 21-continued

Blends and Tensile Measurements of Inventive Compositions

| Example | Blend Component 1 | Blend Component 2 | Blend Component 1/ Blend Component 2 | 2% Sec Mod (MPa) (i) | Elongation at Break (%) (i) | Tensile Strength (MPa) (i) | Set after 300% Hysteresis (%) (ii) |
|---|---|---|---|---|---|---|---|
| 56 | A1[a] | 48 | 25/75 | 4.7 | 1400 | 7.8 | 36 |
| 57 | A1[a] | 48 | 50/50 | 0.5 | 400 | 1.1 | 32 |
| 58 | A1[a] | 48 | 75/25 | 0.9 | 1500 | 3.8 | 30 |
| 59 | A1[a] | 49 | 25/75 | 8.1 | 2200 | 3.5 | 42 |
| 60 | A1[a] | 49 | 50/50 | 4.5 | 1200 | 2.0 | 34 |
| 61 | A1[a] | 49 | 75/25 | 1.4 | 1200 | 1.8 | 30 |
| 62 | A2[b] | 47 | 25/75 | 6.6 | 1800 | 5.0 | 34 |
| 63 | A2[b] | 47 | 50/50 | 7.6 | 1500 | 5.1 | 28 |
| 64 | A2[b] | 47 | 75/25 | 18.0 | 1400 | 5.9 | 20 |
| 65 | A2[b] | 46 | 25/75 | 7.3 | 2200 | 4.5 | 36 |
| 66 | A2[b] | 46 | 50/50 | 14.7 | 1600 | 4.2 | 26 |
| 67 | A2[b] | 46 | 75/25 | 6.6 | 1200 | 6.6 | 19 |
| 68 | A2[b] | 48 | 25/75 | 6.7 | 1400 | 7.8 | 33 |
| 69 | A2[b] | 48 | 50/50 | 8.5 | 1000 | 4.8 | 22 |
| 70 | A2[b] | 48 | 75/25 | 9.3 | 1300 | 8.8 | 18 |
| 71 | A2[b] | 49 | 25/75 | 13.9 | 2000 | 3.4 | 39 |
| 72 | A2[b] | 49 | 50/50 | 10.1 | 1300 | 4.3 | 28 |
| 73 | A2[b] | 49 | 75/25 | 5.5 | 1500 | 10.4 | 18 |
| 74 | A3[c] | 47 | 25/75 | 12.0 | 1733 | 5.0 | 33 |
| 75 | A3[c] | 47 | 50/50 | 19.3 | 1115 | 6.0 | 24 |
| 76 | A3[c] | 47 | 75/25 | 7.6 | 1199 | 15.1 | 18 |
| 77 | A3[c] | 46 | 25/75 | 9.5 | 1922 | 4.2 | 34 |
| 78 | A3[c] | 46 | 50/50 | 10.1 | 1084 | 5.5 | 26 |
| 79 | A3[c] | 46 | 75/25 | 8.3 | 1212 | 12.4 | 21 |
| 80 | A3[c] | 48 | 25/75 | 10.6 | 1229 | 7.7 | 35 |
| 81 | A3[c] | 48 | 50/50 | 9.5 | 1128 | 8.4 | 25 |
| 82 | A3[c] | 48 | 75/25 | 7.3 | 1229 | 15.6 | 19 |
| 83 | A3[c] | 49 | 25/75 | 12.8 | 2108 | 3.3 | 48 |
| 84 | A3[c] | 49 | 50/50 | 18.4 | 996 | 3.1 | 33 |
| 85 | A3[c] | 49 | 75/25 | 7.9 | 1158 | 13.0 | 21 |
| 86 | A4[d] | 47 | 25/75 | 8.5 | 1800 | 4.7 | 29 |
| 87 | A4[d] | 47 | 50/50 | 5.4 | 1100 | 8.0 | 26 |
| 88 | A4[d] | 47 | 75/25 | 4.3 | 1000 | 9.9 | 21 |
| 89 | A4[d] | 46 | 25/75 | 7.0 | 1900 | 3.2 | 29 |
| 90 | A4[d] | 46 | 50/50 | 5.6 | 1100 | 8.4 | 24 |
| 91 | A4[d] | 46 | 75/25 | 4.3 | 1000 | 10.0 | 22 |
| 92 | A4[d] | 48 | 25/75 | 6.1 | 1400 | 8.2 | 27 |
| 93 | A4[d] | 48 | 50/50 | 6.3 | 1200 | 11.1 | 25 |
| 94 | A4[d] | 48 | 75/25 | 3.8 | 900 | 8.4 | 22 |
| 95 | A4[d] | 49 | 25/75 | 10.2 | 1000 | 2.8 | 36 |
| 96 | A4[d] | 49 | 50/50 | 8.0 | 1000 | 8.4 | 27 |
| 97 | A4[d] | 49 | 75/25 | 5.0 | 1000 | 9.7 | 24 |
| 98 | A5[e] | 47 | 25/75 | 9.9 | 1000 | 6.9 | 32 |
| 99 | A5[e] | 47 | 50/50 | 11.9 | 700 | 10.2 | 27 |
| 100 | A5[e] | 47 | 75/25 | 10.9 | 700 | 17.3 | 17 |
| 101 | A5[e] | 46 | 25/75 | 7.8 | 1100 | 6.0 | 32 |
| 102 | A5[e] | 46 | 50/50 | 18.3 | 700 | 11.8 | 26 |
| 103 | A5[e] | 46 | 75/25 | 45.3 | 700 | 20.6 | 25 |
| 104 | A5[e] | 48 | 25/75 | 11.3 | 900 | 9.3 | 29 |
| 105 | A5[e] | 48 | 50/50 | 9.6 | 800 | 14.5 | 19 |
| 106 | A5[e] | 48 | 75/25 | 17.3 | 600 | 16.6 | 20 |
| 107 | A5[e] | 49 | 25/75 | 9.1 | 900 | 6.3 | 45 |
| 108 | A5[e] | 49 | 50/50 | 29.4 | 600 | 9.6 | 28 |
| 109 | A5[e] | 49 | 75/25 | 22.0 | 600 | 15.9 | 23 |

Notes:
[a] Vector 4111 from Dexco Polymers LP
[b] Vector 4211 from Dexco Polymers LP
[c] Vector 8508 from Dexco Polymers LP
[d] KRATON G1657 from KRATON Polymers LLC
[e] KRATON G1652 from KRATON Polymers LLC
(i) Tensile Test at Ambient Conditions (see description in this document)
(ii) 300% Hysteresis Test at Ambient Conditions (see description in this document)

Table 22 shows composition and tensile measurements for ternary blends of an olefin block copolymer, a linear SIS triblock polymer, Vector 4111, a linear SEBS triblock polymer, KRATON G1657 and a linear SBS triblock polymer, Vector 8508.

TABLE 22

Ternary Blends

| Example | Blend Component 1 Resin | Blend Component 2 Resin | Blend Component 3 Resin | Blend Component 1 (%) | Blend Component 2 (%) | Blend Component 3 (%) | Elongation at Break % (i) | Tensile Strength (MPa) (i) | 2% Secant Modulus (MPa) (i) | Immediate Set after 300% Strain (%) (ii) |
|---|---|---|---|---|---|---|---|---|---|---|
| 110 | 46 | A4$^c$ | A1$^a$ | 45 | 10 | 45 | 1300 | 4.1 | 2.9 | 27 |
| 111 | 46 | A4$^c$ | A3$^b$ | 45 | 10 | 45 | 1000 | 5.6 | 8.2 | 29 |
| 112 | 48 | A4$^c$ | A1$^a$ | 45 | 10 | 45 | 1100 | 4.4 | 3.4 | 25 |
| 113 | 48 | A4$^c$ | A3$^b$ | 45 | 10 | 45 | 1200 | 10.8 | 8.5 | 25 |

Notes:
$^a$Vector 4111 from Dexco Polymers LP
$^b$Vector 8508 from Dexco Polymers LP
$^c$KRATON G1657 from KRATON Polymers LLC
(i) Tensile Test at Ambient Conditions (see description in this document)
(ii) 300% Hysteresis Test at Ambient Conditions (see description in this document)

FIG. 14 shows the elastic recovery inventive and comparative examples which comprise SEBS (see table 15). At similar SEBS level, the inventive compositions exhibit greater recovery compared to the comparative examples. Higher recovery is generally recognized as advantaged behavior in the form of greater elasticity.

Figure 15:
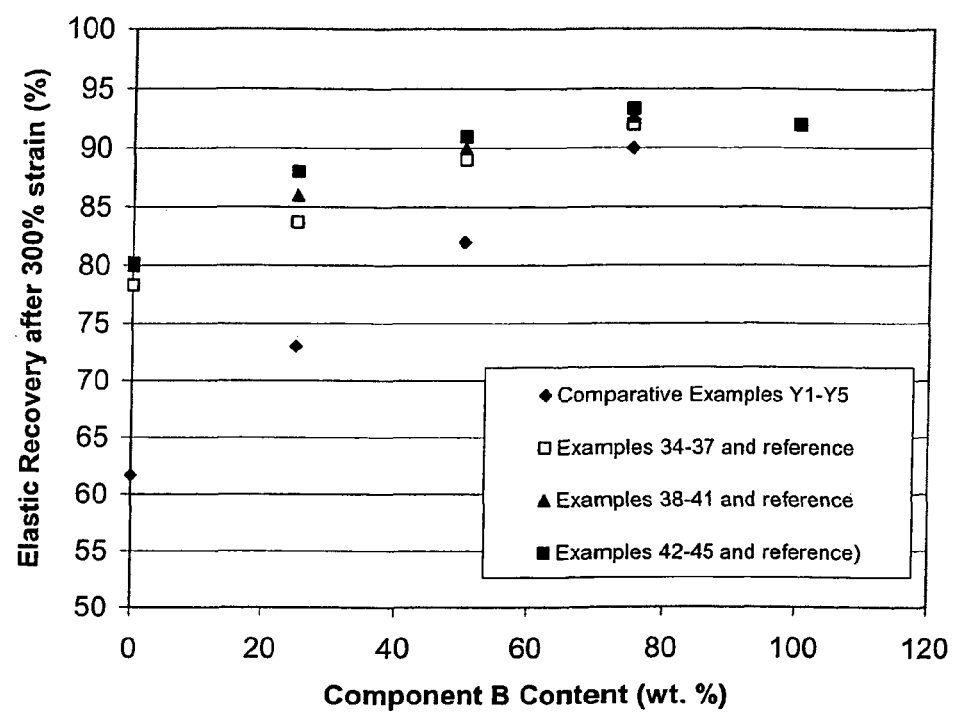
FIG. 15 shows the effect of composition on permanent set after 300% deformation using the 300% hysteresis test.
Figure 16:
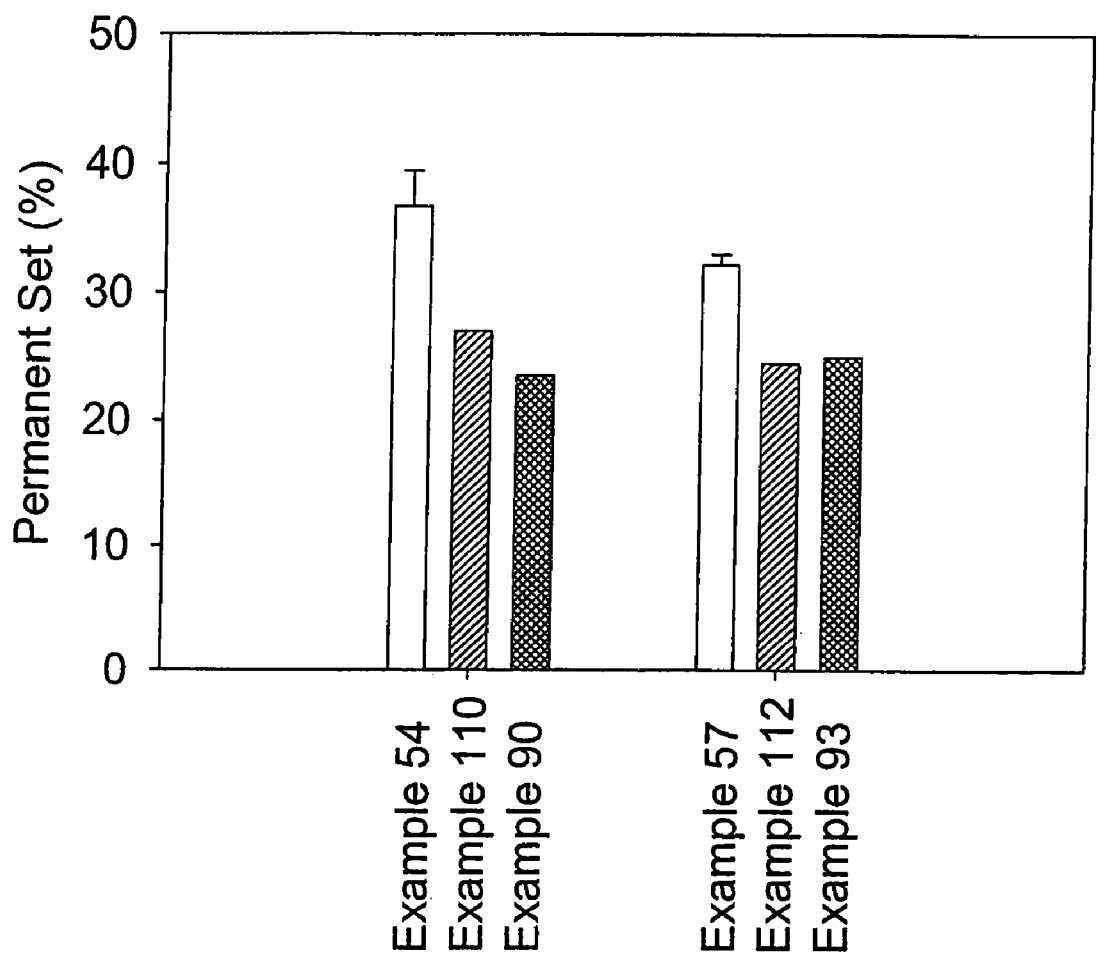
FIG. 16 shows the effect of composition on permanent set after 300% deformation using the 300% hysteresis test.

FIG. 15 compares the elasticity as measured by permanent set of examples comprising ethylene α-olefin and SIS. Examples 54 and 57 exhibit 37 and 32% permanent set, respectively. Examples 110 and 112 have the same proportion of ethylene α-olefin to SIS but with 10% SEBS in the overall composition. These examples exhibit similar permanent set compared to examples 90 and 93 which comprise ethylene α-olefin and SEBS and no SIS. This result shows the utility of ternary blends. Though not intended to be limited by theory, it is thought that compatibility is enhanced in a ternary blend.

While the invention has been described with respect to a limited number of embodiments, the specific features of one embodiment should not be attributed to other embodiments of the invention. No single embodiment is representative of all aspects of the invention. In some embodiments, the compositions or methods may include numerous compounds or steps not mentioned herein. In other embodiments, the compositions or methods do not include, or are substantially free of, any compounds or steps not enumerated herein. Variations and modifications from the described embodiments exist. Finally, any number disclosed herein should be construed to mean approximate, regardless of whether the word "about" or "approximately" is used in describing the number. The appended claims intend to cover all those modifications and variations as falling within the scope of the invention.

We claim:

1. An elastic breathable film comprising:
at least one ethylene/α-olefin interpolymer elastomer, wherein the ethylene/α-olefin interpolymer elastomer
    (a) has a Mw/Mn from about 1.7 to about 3.5, at least one melting point, Tm, in degrees Celsius, and a density, d, in grams/cubic centimeter, wherein the numerical values of Tm and d correspond to the relationship:

$Tm > -2002.9 + 4538.5(d) - 2422.2(d)^2$; or (b) has a Mw/Mn from about 1.7 to about 3.5, and is characterized by a heat of fusion, ΔH in J/g, and a delta quantity, ΔT, in degrees Celsius defined as the temperature difference between the tallest DSC peak and the tallest CRYSTAF peak, wherein the numerical values of ΔT and ΔH have the following relationships:

$\Delta T > -0.1299(\Delta H) + 62.81$ for ΔH greater than zero and up to 130 J/g, $\Delta T \geq 48°$ C. for ΔH greater than 130 J/g, wherein the CRYSTAF peak is determined using at least 5 percent of the cumulative polymer, and if less than 5 percent of the polymer has an identifiable CRYSTAF peak, then the CRYSTAF temperature is 30° C.; or
    (c) is characterized by an elastic recovery, Re, in percent at 300 percent strain and 1 cycle measured with a compression-molded film of the ethylene/α-olefin interpolymer, and has a density, d, in grams/cubic centimeter, wherein the numerical values of Re and d satisfy the following relationship when ethylene/α-olefin interpolymer is substantially free of a cross-linked phase:

Re > 1481 − 1629(d); or (d) has a molecular fraction which elutes between 40° C. and 130° C. when fractionated using TREF, characterized in that the fraction has a molar comonomer content of at least 5 percent higher than that of a comparable random ethylene interpolymer fraction eluting between the same temperatures, wherein said comparable random ethylene interpolymer has the same comonomer(s) and has a melt index, density, and molar comonomer content (based on the whole polymer) within 10 percent of that of the ethylene/α-olefin interpolymer;
    (e) has a storage modulus at 25° C., G' (25° C.), and a storage modulus at 100° C., G'(100° C.), wherein the ratio of G' (25° C.) to G' (100° C.) is in the range of about 1:1 to about 9:1; or
    (f) has a molecular fraction which elutes between 40° C. and 130° C. when fractionated using TREF, characterized in that the fraction has a block index of at least 0.5 and up to about 1 and a molecular weight distribution, Mw/Mn, greater than about 1.3; or
    (g) has an average block index greater than zero and up to about 1.0 and a molecular weight distribution, Mw/Mn, greater than about 1.3; and optionally, a styrenic block copolymer, or a combination thereof wherein the ethylene/α-olefin interpolymer has a density of from about 0.85 to about 0.885 g/cc
wherein the film has microvoids.

2. The film of claim 1 wherein the elastomer comprises at least one polymer selected from the group consisting of styrene-isoprene-styrene polymers, styrene-ethylene-butadiene-styrene polymers, styrene-butadiene-styrene polymers, styrene-ethylenepropylene-styrene, styrene-ethylenepropylene-styrene-ethylenepropylene, hydrogenated polybutadiene polymers and hydrogenated poly isoprene/butadiene polymers.

3. The film of claim 1 wherein the film has a breathability greater than 100 $g/m^2/24$ hours.

4. A fabricated article comprising the film of claim 1 wherein said fabricated article is selected from the group consisting of adult incontinence articles, feminine hygiene articles, infant care articles, surgical gowns, medical drapes, household cleaning articles, expandable food covers, protective clothing, bandages and personal care articles.

5. The film of claim 1 further comprising a filler and a higher crystalline linear polymer.

6. The film of claim 5, wherein the film comprises between about 25 and 70 weight percent filler, between about 5 and 30 weight percent higher crystalline linear polymer, and between about 15 and 60 weight percent elastomer.

7. The film of claim 5 wherein the filler is selected from the group consisting of calcium carbonate, clay, silica, alumina, barium sulfate, sodium carbonate, talc, magnesium sulfate, titanium dioxide, zeolites, aluminum sulfate, cellulose-type powders, diatomaceous earth, gypsum, magnesium sulfate, magnesium carbonate, barium carbonate, kaolin, mica, carbon, calcium oxide, magnesium oxide, aluminum hydroxide, pulp powder, wood powder, cellulose derivatives, polymeric particles, chitin and chitin derivatives and combinations thereof.

8. The film of claim 5 wherein the elastomer comprises at least one polymer selected from the group consisting of styrene-isoprene-styrene polymers, styrene-ethylene-butadiene-styrene polymers, styrene-butadiene-styrene polymers, styrene-ethylenepropylene-styrene, styrene-ethylenepropylene-styrene-ethylenepropylene, hydrogenated polybutadiene polymers and hydrogenated poly isoprene/butadiene polymers.

9. The film of claim 5 wherein the film has a breathability greater than 100 $g/m^2/24$ hours.

10. A fabricated article comprising the film of claim 5 wherein said fabricated article is selected from the group consisting of adult incontinence articles, feminine hygiene articles, infant care articles, surgical gowns, medical drapes, household cleaning articles, expandable food covers, protective clothing, bandages and personal care articles.

* * * * *